United States Patent
Goldberg et al.

(10) Patent No.: US 11,773,371 B2
(45) Date of Patent: Oct. 3, 2023

(54) SKIN TISSUE

(71) Applicant: THE UNIVERSITY OF DURHAM, Durham (GB)

(72) Inventors: Martin Goldberg, Durham (GB); Iakowos Karakesisoglou, Durham (GB); James Carthew, Victoria (AU)

(73) Assignee: THE UNIVERSITY OF DURHAM, Durham (GB)

( * ) Notice: Subject to any disclaimer, the term of this patent is extended or adjusted under 35 U.S.C. 154(b) by 881 days.

(21) Appl. No.: 16/481,771

(22) PCT Filed: Jan. 17, 2018

(86) PCT No.: PCT/GB2018/050120
§ 371 (c)(1),
(2) Date: Jul. 29, 2019

(87) PCT Pub. No.: WO2018/138478
PCT Pub. Date: Aug. 2, 2018

(65) Prior Publication Data
US 2019/0352605 A1 Nov. 21, 2019

(30) Foreign Application Priority Data

Jan. 30, 2017 (GB) ...................................... 1701438

(51) Int. Cl.
*C12N 5/071* (2010.01)
*G01N 33/50* (2006.01)

(52) U.S. Cl.
CPC ....... *C12N 5/0629* (2013.01); *G01N 33/5082* (2013.01); *C12N 2503/06* (2013.01); *C12N 2513/00* (2013.01)

(58) Field of Classification Search
None
See application file for complete search history.

(56) References Cited

U.S. PATENT DOCUMENTS

2009/0258006 A1* 10/2009 Weiss ...................... A61P 43/00
424/130.1
2014/0161917 A1* 6/2014 Lyga ...................... A61Q 19/08
435/6.13

FOREIGN PATENT DOCUMENTS

WO 00/24371 A1 5/2000

OTHER PUBLICATIONS

Xu, Yan-Feng et al. Percutaneous penetration of ketoprofen and ketoprofen isopropyl ester through a tissue engineering skin reconstructed with HaCaT cells. Sep;40(9):782-6. (Year: 2005).*
Xu, YF et al. Percutaneous penetration of ketoprofen and ketoprofen isopropyl ester through a tissue engineering skin reconstructed with HaCaT cells. PubMed—NCBI. (Year: 2005).*
Rashmi, R.N. et al. The nuclear envelope protein Nesprin-2 has roles in cell proliferation and differentiation during wound healing. Nucleus 3:2. pp. 172-186. (Year: 2012).*
Lu, Wenshu et al. Nesprin interchain associations control nuclear size. Cell. Mol. Life Sci. 69:3493-3509 (Year: 2012).*
Lonza. Amaxa Cell Line Nucleofector Kit V. (Year: 2009).*
YF, Xu et al., "[Percutaneous penetration of ketoprofen and ketoprofen isopropyl ester through a tissue engineering skin reconstructed with HaCaT cells].—PubMed—NCBI", Sep. 1, 2005 (Sep. 1, 2005), XP055456013, Retrieved from the Internet: URL:https://www.ncbi.nlm.nih.gov/pubmed/16342676 [retrieve on Mar. 2, 2018] abstract.
Lu, Wenshu et al., "Nesprin interchain associations control nuclear size", CMLS Cellular and Molecular Life Sicences, Birkhauser-Verlag, BA, vol. 69, No. 20, Jun. 1, 2012 (Jun. 1, 2012), pp. 3493-3509.
Hieda, Miki "Implications for Diverse Functions of the LINC Complexes Based on the Structure", Cells, vol. 6, No. 4, Jan. 26, 2017 (2017-0-26), p. 3.
International Search Report and Written Opinion dated Mar. 22, 2018, International Application No. PCT/GB2018/050120, 16 pages.

* cited by examiner

*Primary Examiner* — Nghi V Nguyen
(74) *Attorney, Agent, or Firm* — Kilpatrick Townsend & Stockton LLP

(57) ABSTRACT

A method of creating skin tissue is described, particularly, an in vitro or ex vivo method for creating skin tissue. The invention extends to the use of agents that disrupt the LINC complex in a skin cell to create the skin tissue, and to using the created tissue in an assay to identify or screen anti-ageing compounds. The invention further extends to model skin tissues per se, uses thereof and to kits for creating such model skin tissues.

11 Claims, 19 Drawing Sheets
Specification includes a Sequence Listing.

A

B

Figure 8A and 8B
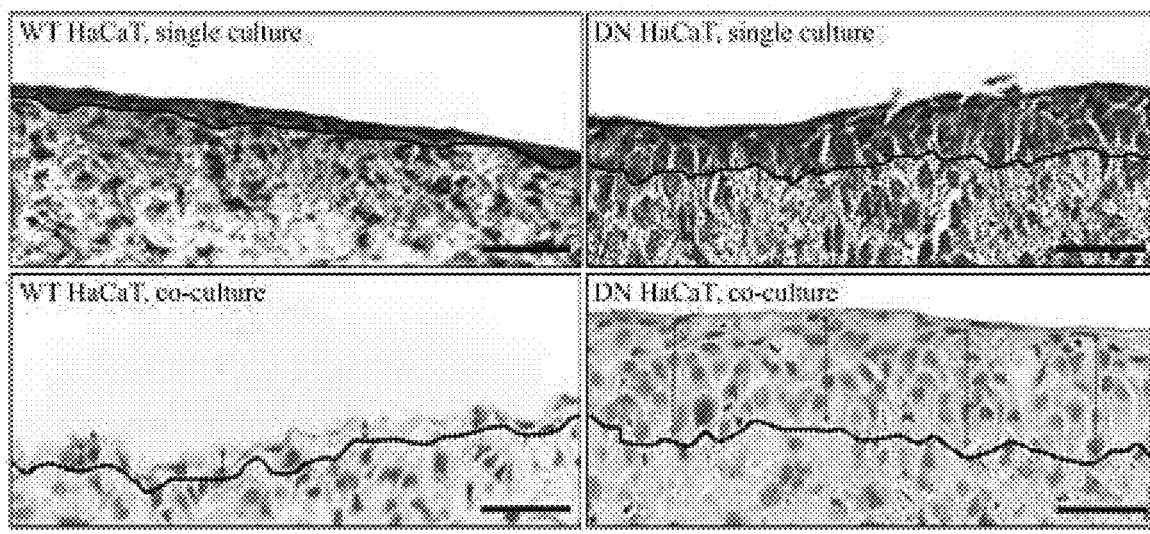
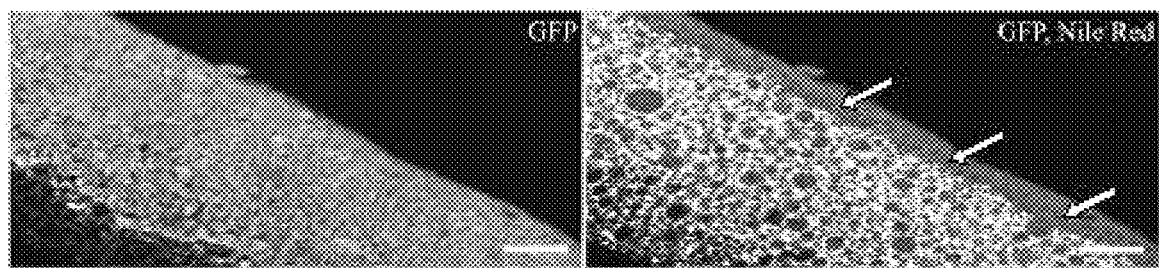
Figure 8C
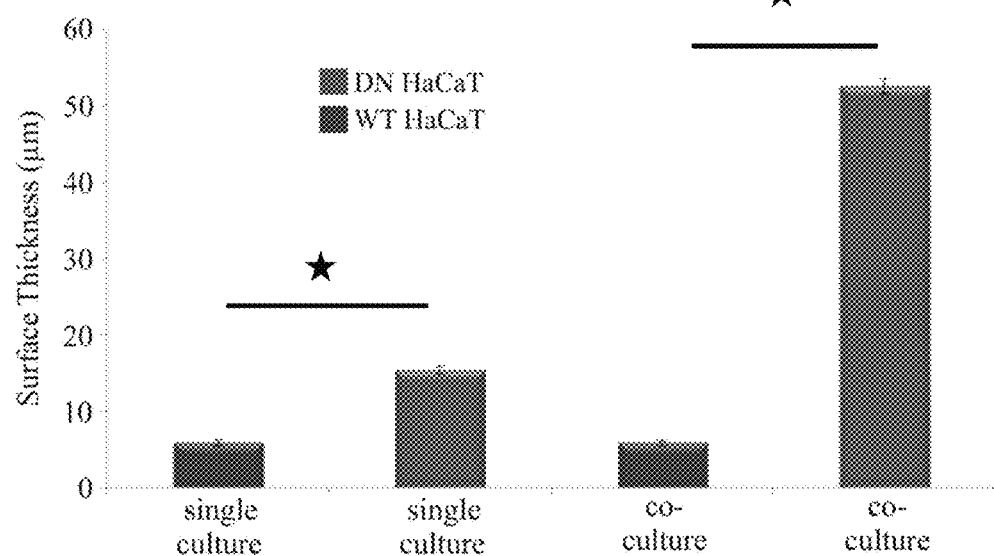

B

SKIN TISSUE

TECHNICAL FIELD

The present invention relates to a method of creating skin tissue, and particularly, although not exclusively, to an in vitro or ex vivo method for creating skin tissue. The invention extends to the use of agents that disrupt the LINC complex in a skin cell to create the skin tissue, and to using the created tissue in an assay to identify or screen anti-ageing compounds. The invention further extends to model skin tissues per se, uses thereof and to kits for creating such model skin tissues.

BACKGROUND

The foundation of tissue engineering is the generation of biomechanically, biochemically, structurally and topologically defined synthetic 3D biomaterials that mimic the native extracellular microenvironment of cells. Progress has been made in the development of organotypic equivalents. However, generating proper biomimetic scaffolds presents significant technical challenges. Tissue engineering is time consuming, involves high costs and there are major issues regarding biofunctionality, compatibility and variability, which severely impair their biomedical usage. A major limitation is that native microenvironments are highly variable and complex and their biochemical, biomechanical and structural compositions are difficult to replicate in the laboratory. Epidermal keratinocytes, for example, rest on a stiff (MPa) collagen IV/VII and laminin-rich 2D extracellular matrix (ECM) termed the basement membrane (BM), while dermal fibroblasts reside on considerably softer (0.1-10 kPa) collagen III/I and fibrillin/elastin-based 3D matrixes. ECM properties, including composition, porosity, stiffness, structure and importantly the immediate cellular surrounding, control cell properties, e.g. identity, proliferation, longevity, signalling, behaviour and architecture. Therefore, designing universal scaffolds that determine the correct properties of different cell/tissue types is not feasible because, for instance, epidermal keratinocytes will naturally exist in a very different physical environment to a dermal fibroblast.

There is therefore a need for an improved means of inducing in vitro or ex vivo cells, such as keratinocytes, in such a way so as to accurately model the structural, biomechanical and biochemical properties of corresponding cells that are found in the in vivo skin tissue.

BRIEF SUMMARY OF THE DISCLOSURE

The inventors have found that although in vivo cellular microenvironments vary in different tissues, the mechanisms by which cells sense and react to their environment are the same. Extracellular cues from the ECM and other factors are sensed by plasma membrane receptors that translate these signals into intracellular biochemical messengers and biomechanical forces that modulate chromatin organization and gene expression. The LINC (Linker of the Nucleoskeleton and Cytoskeleton) complex is a central switch of this molecular and structural circuit. Instead of engineering an appropriate extracellular environment for keratinocytes in vitro, that will ignite proper LINC complex signalling, the inventors modulated directly the LINC complex in keratinocytes using a dominant negative protein-based approach. In other words, instead of using signals from outside the cell to determine cellular properties, the inventors operated the "LINC switch" directly. By doing so, they were surprisingly able to affect cellular signalling (e.g. TGF-beta, wnt etc.), cell-cell adhesion, cell-ECM interactions, cellular biomechanics, cell architecture and importantly cellular organization.

DETAILED DESCRIPTION

Thus, according to a first aspect of the invention, there is provided a method of preparing skin tissue, the method comprising:
  (i) contacting a skin cell with an agent that disrupts the LINC complex of the cell;
  (ii) culturing the cell on a substrate comprising culture media to induce proliferation of the cell into a plurality of cells; and
  (iii) removing a portion of culture media from the substrate such that the plurality of cells are disposed in an interface between culture media remaining on the substrate and air, to thereby induce differentiation of the cells into skin tissue.

Advantageously, the method according to the first aspect can be used to create skin in vitro or ex vivo without the use of a biomimetic scaffold, i.e. a scaffold that mimics the extracellular microenvironment of cells found in normal skin tissue. Thus, the above-mentioned problems associated with the use of such a scaffold are avoided.

Furthermore, the method of the invention can be used to create tissue comprising cells that exhibit biochemical, biomechanical and structural properties similar or even identical to that of corresponding cells in tissue, in vivo. Moreover, the inventors have found that disrupting the LINC complex in cells, such as keratinocytes, makes the cells significantly softer compared to their wild type counterparts. In addition, disrupting the LINC complex in cells causes the cells to organize themselves into compact colonies when grown in 2D. Importantly, when cells that have a disrupted LINC complex are grown in 3D, they form multi-layered and properly organized epidermal structures much faster than normal epithelial cells.

As shown in the method of the first aspect above, culturing cells, in which the LINC complex has been disrupted, under suitable conditions causes them to proliferate and differentiate into skin cells without the use of a biomimetic scaffold. In one embodiment, the method is an in vitro and/or ex vivo method.

The LINC complex is an intracellular network of multiple proteins found in eukaryotic cells. It spans the nuclear membrane and connects genetic material (and other nuclear components) to plasma membrane receptors via cytoskeletal structures (see FIGS. 1 and 2). Consequently, the LINC complex influences multiple cellular processes, including nuclear positioning, force transduction and cell signalling pathways. The core proteins of the LINC complex are Nesprins, SUN proteins and lamins (see FIGS. 1 and 2).

Nesprins (Nuclear envelope spectrin repeat proteins) are a family of spectrin proteins primarily situated in the outer nuclear membrane of cells. They function as adaptors that connect the nucleus of a cell to the cytoskeleton, microtubule associated motor proteins (e.g. dynein and kinesin-1) and the centrosome. The Nesprin family comprises four subtypes of nesprin (i.e. Nesprin-1, Nesprin-2, Nesprin-3 and Nesprin-4), each of which has multiple isoforms. The largest isoforms of Nesprin-1 and Nesprin-2 are over 800 kDa in weight, and referred to as giant Nesprin proteins. Giant Nesprin-1 and giant Nesprin-2 comprise an N-terminal F-actin binding domain (ABD), a long spectrin repeat containing region and a C-terminal transmembrane domain followed by a short region that projects into the nuclear envelope and connects to the SUN domain of SUN proteins (i.e. the KASH domain). All giant nesprins isoforms contain an ABD. Most, but not all isoforms of Nesprin contain a KASH domain.

Four genes, which are referred to as SYNE1, SYNE2, SYNE3 and SYNE4, encode Nesprin subtypes Nesprin-1, Nesprin-2, Nesprin-3 and Nesprin-4, respectively. Each subtype of Nesprin has multiple isoforms due to alternative transcriptional initiation, termination and splicing of the gene by which they are encoded.

The first gene, SYNE1, encodes the Nesprin-1 subtype. The nucleotide sequence that encodes one embodiment of SYNE1 can be found under genomic identifier ENSG00000131018.

The KASH domain of the Nesprin-1 subtype is encoded by a single exon, which also encodes a stop codon at the 3' end of the SYNE1 gene. In one embodiment, the nucleotide sequence of the exon that encodes the KASH domain of the Nesprin-1 subtype is referred to herein as SEQ ID No. 1 (previously referred to as SEQ ID No. 2 in patent application GB1701438.2), as follows:

[SEQ ID No. 1]
GTCCACAAAAGGTGGCTCCGATTCCTCCCTTTCTGAGCCAGGGCCAGGTC

GGTCCGGCCGCGGCTTCCTGTTCAGAGTCCTCCGAGCAGCTCTTCCCCTT

CAGCTTCTCCTGCTCCTCCTCATCGGGCTTGCCTGCCTTGTACCAATGTC

AGAGGAAGACTACAGCTGTGCCCTCTCCAACAACTTTGCCCGGTCATTCC

ACCCCATGCTCAGATACACGAATGGCCCTCCTCCACTCTGA

In one embodiment, the amino acid sequence that encodes the KASH domain of the Nesprin-1 subtype is referred to herein as SEQ ID No. 2 (previously referred to as SEQ ID No. 3 in patent application GB1701438.2), as follows:

[SEQ ID No. 2]
AALPLQLLLLLLIGLACLVPMSEEDYSCALSNNFARSFHPMLRYTNGPP

PL

The second gene, SYNE2, encodes the Nesprin-2 subtype. The nucleotide sequence that encodes one embodiment of SYNE2 can be found under genomic identifier ENSG00000054654.

The KASH domain of the Nesprin-2 subtype is encoded by a single exon, which also encodes a stop codon at the 3' end of the SYNE2 gene. In one embodiment, the nucleotide sequence of the exon that encodes the KASH domain of the Nesprin-2 subtype is referred to herein as SEQ ID No. 3 (previously referred to as SEQ ID No. 5 in patent application GB1701438.2), as follows:

[SEQ ID No. 3]
GGTCCCCGGCAGCACACGGCCACAGCGCTCCTTCCTCTCAAGGGTGGTCC

GGGCAGCCCTACCCCTGCAGCTGCTCCTCCTGCTGCTGCTGCTCCTGGCC

TGCCTGCTGCCCTCCTCCGAAGAAGACTACAGCTGCACTCAGGCCAACAA

CTTTGCCCGGTCCTTTTACCCCATGCTGAGGTACACCAATGGGCCACCCC

CCACATAG

In one embodiment, the amino acid sequence that encodes the KASH domain of the Nesprin-2 subtype is referred to herein as SEQ ID No. 4 (previously referred to as SEQ ID No. 6 in patent application GB1701438.2), as follows:

[SEQ ID No. 4]
AALPLQLLLLLLLLLACLLPSSEEDYSCTQANNFARSFYPMLRYTNGPP

PT

The third gene, SYNE3 encodes the Nesprin-3 subtype. The nucleotide sequence that encodes one embodiment of SYNE3 can be found under genomic identifier ENSG00000176438.

ENSG00000176438 encodes five different mRNA transcripts (i.e. SYNE3-001, -002, -003, -004 and -005). Only transcripts SYNE3-001, -003, -004, and -005 encode a Nesprin protein. Transcript SYNE3-005 encodes a Nesprin-3 protein, which is equivalent to the murine Nesprin-3a isoform. Nesprins encoded by SYNE3-001,-003, -004 and -005 comprise a KASH domain.

The KASH domain of the Nesprin-3 subtype is encoded by a single exon, which also encodes a stop codon at the 3' end of the SYNE3 gene. In one embodiment, the nucleotide sequence of the exon that encodes the KASH domain of the Nesprin-3 subtype is referred to herein as SEQ ID No. 5 (previously referred to as SEQ ID No. 8 in patent application GB1701438.2), as follows:

[SEQ ID No. 5]
ACTCGGCGGTGGCGAGGACTGGGCTCCCTCTTCCGGAGGGCGTGCTGTGT

GGCGCTCCCACTGCAGCTGCTTCTGCTGCTGTTCCTCCTCCTGCTGTTCC

TGCTCCCAATCAGGGAAGAGGACCGCAGCTGCACCCTGGCCAACAACTTC

GCCCGCTCCTTCACGCTCATGCTGCGCTACAATGGCCCACCACCCACCTA

A

In one embodiment, the amino acid sequence that encodes the KASH domain of Nesprin-3 is referred to herein as SEQ ID No. 6 (previously referred to as SEQ ID No. 9 in patent application GB1701438.2), as follows:

[SEQ ID No. 6]
VALPLQLLLLLFLLLLFLLPIREEDRSCTLANNFARSFTLMLRYNGPPPT

The fourth gene, SYNE 4 encodes Nesprin-4. The nucleotide sequence that encodes one embodiment of Nesprin-4 can be found under genomic identifier ENSG00000181392.

SYNE4 encodes seven different mRNA transcripts (i.e. SYNE4-001, -002, -003, -004, -005, -006, and -007). Only transcripts SYNE4-001, -003, -004, -005 and -006 encode proteins. Transcript SYNE4-001 encodes Nesprin-4 protein. Transcripts SYNE4-001 and -004 encode isoforms comprising a KASH domain.

The KASH domain of the Nesprin-4 subtype is encoded by a single exon, which also encodes a stop codon at the 3' end of the SYNE4 gene. In one embodiment, the nucleotide sequence of the exon that encodes the KASH domain of the Nesprin-4 subtype is referred to herein as SEQ ID No. 7 (previously referred to as SEQ ID No. 11 in patent application GB1701438.2), as follows:

[SEQ ID No. 7]
GGCCCCCGATCCTGCATCCAGGCAGCCTCTGACCTTCCTCCTTATCCTCT

TCCTCCTCTTCCTCCTCCTGGTGGGTGCCATGTTTCTCCTGCCCGCGTCA

-continued

```
GGAGGCCCTGCTGCTCTCATGCCCGAATACCCAGGACACCCTACCTGGT

GCTCAGCTATGTCAATGGTCTTCCCCCAGTCTGA
```

In one embodiment, the amino acid sequence that encodes the KASH domain of Nesprin-4 is referred to herein as SEQ ID No. 8 (previously referred to as SEQ ID No. 12 in patent application GB1701438.2), as follows:

[SEQ ID No. 8]
```
FLLILFLLFLLLVGAMFLLPASGGPCCSHARIPRTPYLVLSYVNGLPPV
```

Thus, in one embodiment of the invention, the LINC complex that is disrupted in step (i) of the method of the invention may comprise a Nesprin protein. The Nesprin protein may be selected from Nesprin-1, Nesprin-2, Nesprin-3 and Nesprin-4. Preferably, the Nesprin protein is Nesprin-1, Nesprin-2 or Nesprin-4. Most preferably, the Nesprin protein comprises a KASH domain.

The LINC complex that is disrupted in step (i) of the method may comprise a protein encoded by SYNE1, SYNE2, SYNE3 and/or SYNE4, or a variant or fragment thereof. Preferably, the Nesprin protein is encoded by SYNE1, SYNE2 and/or SYNE4.

The LINC complex that is disrupted in step (i) of the method may comprise a Nesprin protein encoded by a nucleotide sequence substantially as set out in any one or more of the nucleotide sequences found under genomic identifiers ENSG00000131018, ENSG00000054654, ENSG00000176438 and/or ENSG00000181392, or a variant or fragment thereof. Preferably, the Nesprin protein is encoded by a nucleotide sequence substantially as the nucleotide sequences found under genomic identifiers ENSG00000131018, ENSG0000054654, ENSG00000176438 and/or ENSG00000181392, or a variant or fragment thereof.

The LINC complex that is disrupted in step (i) of the method may comprise a KASH domain. The KASH domain may be encoded by a nucleotide sequence substantially as set out in SEQ ID No. 1, 3, 5 and/or 7, or a variant or fragment thereof. Most preferably, the Nesprin protein comprises a KASH domain encoded by a nucleotide sequence substantially as set out in SEQ ID No. 1, 3, 5 and/or 7, or a variant or fragment thereof. The KASH domain may comprise an amino acid sequence substantially as set out in SEQ ID No. 2, 4, 6 and/or 8, or a variant or fragment thereof. Most preferably, the KASH domain comprises an amino acid sequence substantially as set out in SEQ ID No. 2, 4, 6 and/or 8, or a variant or fragment thereof.

SUN (Sad1 and UNC-84 homology) proteins are a family of proteins primarily located in the perinuclear space (i.e. between the outer and inner nuclear membrane) and nucleoplasm of cells (see FIG. 2). Consequently, the KASH domains and C-terminal domains of SUNs "bridge" the inner and outer nuclear membranes. However, SUN proteins also link the inner nuclear membranes (INM) to the underlying nuclear lamina and chromatin (see FIG. 2).

SUN proteins comprise an N-terminal domain, a transmembrane domain, a coiled-coil domain, and a conserved C-terminal domain (the SUN domain), which binds to the KASH domain of Nesprins, see, for example, FIGS. 2 and 3. The C-terminal domain and the coiled-coil domain are located in the perinuclear space, whereas the N-terminal domain is located in the nucleoplasm.

Five subtypes of SUN proteins are found in vertebrates, SUN1, SUN2, SUN3, SUN4 (sperm associated antigen 4, SPAG4) and SUN5 (SPAG4 like, SPAGL, Astrin).

In mice, there are at least seven different isoforms of the SUN1 subtype, all of which contain identical C-terminal SUN domain sequences but vary in their nucleoplasmic N-terminal sequences. Like the full-length SUN2 protein, the majority of SUN isoforms are widely expressed.

The nucleotide sequence of one embodiment of SUN1 can be found under genomic identifier ENSG00000164828. There are 35 splice variants of SUN1, which are referred to herein as SUN1-001, SUN1-002 . . . to SUN1-035, respectively.

The nucleotide sequence that encodes one embodiment of the SUN1 SUN-domain is referred to herein as SEQ ID No. 9 (previously referred to as SEQ ID No. 14 in patent application GB1701438.2), as follows:

[SEQ ID No. 9]
```
GTGGCAGCATCTTGAGTACTCGCTGTTCTGAAACTTACGAAACCAAAACG

GCGCTGATGAGTCTGTTTGGGATCCCGCTGTGGTACTTCTCGCAGTCCCC

GCGCGTGGTCATCCAGCCTGACATTTACCCCGGTAACTGCTGGGCATTTA

AAGGCTCCCAGGGGTACCTGGTGGTGAGGCTCTCCATGATGATCCACCCA

GCCGCCTTCACTCTGGAGCACATCCCTAAGACGCTGTCGCCAACAGGCAA

CATCAGCAGCGCCCCCAAGGACTTCGCCGTCTATGGATTAGAAAATGAGT

ATCAGGAAGAAGGGCAGCTTCTGGGACAGTTCACGTATGATCAGGATGGG

GAGTCGCTCCAGATGTTCCAGGCCCTGAAAAGACCCGACGACACAGCTTT

CCAAATAGTGGAACTTCGGATTTTTTCTAACTGGGGCCATCCTGAGTATA

CCTGTCTGTATCGGTTCAGAGTTCATGGCGAACCTGTCAAGTGA
```

The amino acid sequence that encodes one embodiment of the SUN1 SUN-domain is referred to herein as SEQ ID No. 10, as follows:

[SEQ ID No. 10]
```
GSILSTRCSETYETKTALMSLFGIPLWYFSQSPRVVIQPDIYPGNCWAFK

GSQGYLVVRLSMMIHPAAFTLEHIPKTLSPTGNISSAPKDFAVYGLENEY

QEEGQLLGQFTYDQDGESLQMFQALKRPDDTAFQIVELRIFSNWGHPEYT

CLYRFRVHGEPVK
```

The nucleotide sequence that encodes one embodiment of SUN2 can be found under genomic identifier ENSG00000100242. There are 18 splice variants of SUN2, which are referred to herein as SUN2-001, SUN2-002 . . . to SUN2-018, respectively.

The nucleotide sequence that encodes one embodiment of the SUN2 SUN-domain is referred to herein as SEQ ID No. 11 (previously referred to as SEQ ID No. 17 in patent application GB1701438.2), as follows:

[SEQ ID No. 11]
```
GGGCCAGCGTCATCAGCACCCGATGTTCTGAGACCTACGAGACCAAGACG

GCCCTCCTCAGCCTCTTCGGCATCCCCCTGTGGTACCACTCCCAGTCACC

CCGAGTCATCCTCCAGCCAGATGTGCACCCAGGCAACTGCTGGGCCTTCC

AGGGGCCACAAGGCTTCGCCGTGGTCCGCCTCTCTGCCCGCATCCGCCCC
```

```
ACAGCCGTTACCTTAGAGCATGTGCCCAAGGCCTTGTCACCCAACAGCAC

TATCTCCAGTGCCCCCAAGGACTTCGCCATCTTTGGGTTTGACGAAGACC

TGCAGCAGGAGGGGACACTCCTTGGCAAGTTCACTTACGATCAGGACGGC

GAGCCTATTCAGACGTTTCACTTTCAGGCCCCTACGATGGCCACGTACCA

GGTGGTGGAGCTGCGGATCCTGACTAACTGGGGCCACCCCGAGTACACCT

GCATCTACCGCTTCAGAGTGCATGGGGAGCCCGCCCACTAG
```

The amino acid sequence that encodes one embodiment of the SUN2 SUN-domain is referred to herein as SEQ ID No. 12 (previously referred to as SEQ ID No. 18 in patent application GB1701438.2), as follows:

```
                                        [SEQ ID No. 12]
ASVISTRCSETYETKTALLSLFGIPLWYHSQSPRVILQPDVHPGNCWAFQ

GPQGFAVVRLSARIRPTAVTLEHVPKALSPNSTISSAPKDFAIFGFDEDL

QQEGTLLGKFTYDQDGEPIQTFHFQAPTMATYQVVELRILTNWGHPEYTC

IYRFRVHGEPAH
```

The nucleotide sequence that encodes one embodiment of SUN3 can be found under genomic identifier ENSG00000164744. There are 10 splice variants of SUN3, which are referred to herein as SUN3-001, SUN3-002 . . . to SUN1-010, respectively.

The nucleotide sequence that encodes one embodiment of the SUN3 SUN-domain is referred to herein as SEQ ID No. 13 (previously referred to as SEQ ID No. 20 in patent application GB1701438.2), as follows:

```
                                        [SEQ ID No. 13]
GAGCCTCCATCATTGAAGCTGGGACCTCAGAAAGTTATAAAAATAATAAA

GCAAAATTGTACTGGCATGGGATAGGTTTCCTAAATCATGAAATGCCTCC

AGATATTATTCTTCAGCCGGATGTCTACCCTGGAAAGTGCTGGCTTTTC

CAGGTTCCCAGGGTCATACCCTAATCAAGCTTGCTACAAAGATCATACCA

ACTGCTGTTACCATGGAGCACATCTCAGAGAAGGTGTCTCCGTCAGGAAA

CATCTCCAGTGCACCCAAGGAATTTTCTGTCTATGGCATCACAAAAAAAT

GTGAAGGAGAAGAAATTTTCCTAGGTCAGTTTATATATAACAAAACAGGA

ACCACCGTTCAAACATTTGAACTCCAGCATGCAGTTTCTGAATATTTATT

ATGTGTGAAACTTAATATCTTTAGCAACTGGGGACACCCGAAGTATACTT

GTTTATATCGATTCAGGGTCCATGGCACACCAGGCAAGCACATCTAG
```

The amino acid sequence that encodes one embodiment of the SUN3 SUN-domain is referred to herein as SEQ ID No. 14 (previously referred to as SEQ ID No. 21 in patent application GB1701438.2), as follows:

```
                                        [SEQ ID No. 14]
ASIIEAGTSESYKNNKAKLYWHGIGFLNHEMPPDIILQPDVYPGKCWAFP

GSQGHTLIKLATKIIPTAVTMEHISEKVSPSGNISSAPKEFSVYGITKKC

EGEEIFLGQFIYNKTGTTVQTFELQHAVSEYLLCVKLNIFSNWGHPKYTC

LYRFRVHGTPGKHI
```

The nucleotide sequence of one embodiment of SUN4 (SPAG4) can be found under genomic identifier ENSG00000061656. There are 7 splice variants of SUN1, which are referred to herein as SUN4-001, SUN4-002 . . . to SUN4-007, respectively.

The nucleotide sequence that encodes one embodiment of the SUN4 SUN-domain is referred to herein as SEQ ID No. 15 (previously referred to as SEQ ID No. 23 in patent application GB1701438.2), as follows:

```
                                        [SEQ ID No. 15]
GAGCCTCCATCGACCTGCAGAAGACATCCCACGATTACGCAGACAGGAAC

ACTGCCTACTTCTGGAATCGCTTCAGCTTCTGGAACTACGCACGGCCGCC

CACGGTTATCCTGGAGCCCCACGTGTTCCCTGGGAATTGCTGGGCTTTTG

AAGGCGACCAAGGCCAGGTGGTGATCCAACTGCCGGGCCGAGTGCAGCTG

AGCGACATCACTCTGCAGCATCCACCGCCCAGCGTGGAGCACACCGGAGG

AGCCAACAGCGCCCCCCGCGATTTCGCGGTCTTTGGCCTCCAGGTTTATG

ATGAAACTGAAGTTTCCTTGGGGAAATTCACCTTCGATGTTGAGAAATCG

GAGATTCAGACTTTCCACCTGCAGAATGACCCCCCAGCTGCCTTTCCCAA

GGTGAAGATCCAGATTCTAAGCAACTGGGGCCACCCCGTTTCACGTGCT

TGTATCGAGTCCGTGCCCACGGTGTGCGAACCTCAGAGGGGGCAGAGGGC

AGTGCACAGGGGCCCCATTAA
```

The amino acid sequence that encodes one embodiment of the SUN4 SUN-domain is referred to herein as SEQ ID No. 16 (previously referred to as SEQ ID No. 24 in patent application GB1701438.2), as follows:

```
                                        [SEQ ID No. 16]
ASIDLQKTSHDYADRNTAYFWNRFSFWNYARPPTVILEPHVFPGNCWAFE

GDQGQVVIQLPGRVQLSDITLQHPPPSVEHTGGANSAPRDFAVFGLQVYD

ETEVSLGKFTFDVEKSEIQTFHLQNDPPAAFPKVKIQILSNWGHPRFTCL

YRVRAHGVRTSEGAEGSAQGPH
```

The nucleotide sequence that encodes one embodiment of SUN5 can be found under genomic identifier ENSG00000167098. There are 4 splice variants of SUN5, which are referred to herein as SUN5-001, SUN5-002, SUN5-004 and SUN5-004, respectively.

The nucleotide sequence that encodes one embodiment of the SUN5 SUN-domain is referred to herein as SEQ ID No. 17 (previously referred to as SEQ ID No. 26 in patent application GB1701438.2), as follows:

```
                                        [SEQ ID No. 17]
GGGCCAGCATTGACTTTGAGCACACGTCAGTCACCTATAACCATGAGAAG

GCCCACTCCTACTGGAACTGGATCCAGCTGTGGAACTACGCACAGCCCCC

AGACGTGATCCTTGAGCCCAACGTGACACCTGGCAATTGCTGGGCCTTTG

AGGGTGACCGCGGCCAGGTGACCATCCAATTGGCTCAGAAGGTTTACCTG

TCCAACCTCACGCTGCAGCACATCCCCAAGACCATCTCATTGTCAGGCAG

CCTGGACACCGCCCCCAAGGACTTCGTCATCTATGGCATGGAGGGCTCCC

CCAAGGAGGAGGTGTTCCTGGGGGCATTTCAGTTTCAGCCAGAAACATC

ATCCAGATGTTCCCACTCCAGAACCAGCCGGCCCGGGCTTTCAGTGCGGT

CAAGGTGAAGATCTCAAGCAACTGGGGGAACCCAGGCTTCACTTGCCTGT
```

ACCGCGTGCGAGTGCATGGCTCTGTGGCCCCGCCCAGAGAGCAGCCTCAC

CAGAACCCCTACCCTAAGAGAGATTAA

The amino acid sequence that encodes one embodiment of the SUN5 SUN-domain is referred to herein as SEQ ID No. 18 (previously referred to as SEQ ID No. 27 in patent application GB1701438.2) as follows:

[SEQ ID No. 18]
ASIDFEHTSVTYNHEKAHSYWNWIQLWNYAQPPDVILEPNVTPGNCWAFE

GDRGQVTIQLAQKVYLSNLTLQHIPKTISLSGSLDTAPKDFVIYGMEGSP

KEEVFLGAFQFQPENIIQMFPLQNQPARAFSAVKVKISSNWGNPGFTCLY

RVRVHGSVAPPREQPHQNPYPKRD

Thus, in one embodiment of the invention, the LINC complex that is disrupted in step (i) of the method of the invention may comprise a SUN protein. The SUN protein may be selected from SUN1, SUN2, SUN3, SUN4 and SUN5. Preferably, the SUN protein is SUN1 or SUN2. Most preferably, the SUN protein comprises a SUN domain. The SUN protein may be encoded by a nucleotide sequence substantially as set out in the nucleotide sequences found under genomic identifiers ENSG00000164828, ENSG00000100242, ENSG00000164744, ENSG00000061656 or ENSG00000167098, or a variant or fragment thereof. Preferably, the SUN protein is encoded by a nucleotide sequence substantially as set out in the nucleotide sequences found under genomic identifiers ENSG00000164828 or ENSG00000100242, or a variant or fragment thereof. The LINC complex which is disrupted in step (i) of the method of the invention may comprise a SUN domain. The SUN domain may be encoded by a nucleotide sequence substantially as set out in SEQ ID No. 9, 11, 13, 15 and/or 17, or a variant or fragment thereof. Most preferably, the SUN protein comprises a SUN domain encoded by a nucleotide sequence substantially as set out in SEQ ID No. 9 or SEQ ID No. 11, or a variant or fragment thereof. The SUN domain comprises an amino acid nucleotide sequence substantially as set out in SEQ ID No.10, 12, 14, 16 and/or 18, or a variant or fragment thereof. Most preferably, the SUN domain comprises an amino acid sequence substantially as set out in SEQ ID No. 10 or SEQ ID No. 12, or a variant or fragment thereof.

Lamins are a family of proteins primarily located in the nuclear lamina (i.e. on the inner face of the inner nuclear membrane). They attach to SUN proteins and act as an anchor. It is believed that this attachment enables force exerted by the components of the cytoskeleton to be transmitted directly to the nucleus. Lamins comprise A-type Lamins and B-type Lamins.

A-type Lamins are encoded by a single gene, LMNA, which undergoes alternative splicing to generate Lamins A and C. The nucleotide sequence of LMNA can be found under genomic identifier ENSG00000160789

The nucleotide sequence that encodes of one embodiment of Lamin A (ENST00000368300) is referred to herein as SEQ ID No. 19 (previously referred to as SEQ ID No. 29 in patent application GB1701438.2), as follows:

[SEQ ID No. 19]
ATGGAGACCCCGTCCCAGCGGCGCGCCACCCGCAGCGGGGCGCAGGCCAG

CTCCACTCCGCTGTCGCCCACCCGCATCACCCGGCTGCAGGAGAAGGAGG

ACCTGCAGGAGCTCAATGATCGCTTGGCGGTCTACATCGACCGTGTGCGC

TCGCTGGAAACGGAGAACGCAGGGCTGCGCCTTCGCATCACCGAGTCTGA

AGAGGTGGTCAGCCGCGAGGTGTCCGGCATCAAGGCCGCCTACGAGGCCG

AGCTCGGGGATGCCCGCAAGACCCTTGACTCAGTAGCCAAGGAGCGCGCC

CGCCTGCAGCTGGAGCTGAGCAAAGTGCGTGAGGAGTTTAAGGAGCTGAA

AGCGCGCAATACCAAGAAGGAGGGTGACCTGATAGCTGCTCAGGCTCGGC

TGAAGGACCTGGAGGCTCTGCTGAACTCCAAGGAGGCCGCACTGAGCACT

GCTCTCAGTGAGAAGCGCACGCTGGAGGGCGAGCTGCATGATCTGCGGGG

CCAGGTGGCCAAGCTTGAGGCAGCCCTAGGTGAGGCCAAGAAGCAACTTC

AGGATGAGATGCTGCGGCGGGTGGATGCTGAGAACAGGCTGCAGACCATG

AAGGAGGAACTGGACTTCCAGAAGAACATCTACAGTGAGGAGCTGCGTGA

GACCAAGCGCCGTCATGAGACCCGACTGGTGGAGATTGACAATGGGAAGC

AGCGTGAGTTTGAGAGCCGGCTGGCGGATGCGCTGCAGGAACTGCGGGCC

CAGCATGAGGACCAGGTGGAGCAGTATAAGAAGGAGCTGGAGAAGACTTA

TTCTGCCAAGCTGGACAATGCCAGGCAGTCTGCTGAGAGGAACAGCAACC

TGGTGGGGGCTGCCCACGAGGAGCTGCAGCAGTCGCGCATCCGCATCGAC

AGCCTCTCTGCCCAGCTCAGCCAGCTCCAGAAGCAGCTGGCAGCCAAGGA

GGCGAAGCTTCGAGACCTGGAGGACTCACTGGCCCGTGAGCGGGACACCA

GCCGGCGGCTGCTGGCGGAAAAGGAGCGGGAGATGGCCGAGATGCGGGCA

AGGATGCAGCAGCAGCTGGACGAGTACCAGGAGCTTCTGGACATCAAGCT

GGCCCTGGACATGGAGATCCACGCCTACCGCAAGCTCTTGGAGGGCGAGG

AGGAGAGGCTACGCCTGTCCCCCAGCCCTACCTCGCAGCGCAGCCGTGGC

CGTGCTTCCTCTCACTCATCCCAGACACAGGGTGGGGCAGCGTCACCAA

AAAGCGCAAACTGGAGTCCACTGAGAGCCGCAGCAGCTTCTCACAGCACG

CACGCACTAGCGGGCGCGTGGCCGTGGAGGAGGTGGATGAGGAGGGCAAG

TTTGTCCGGCTGCGCAACAAGTCCAATGAGGACCAGTCCATGGGCAATTG

GCAGATCAAGCGCCAGAATGGAGATGATCCCTTGCTGACTTACCGGTTCC

CACCAAAGTTCACCCTGAAGGCTGGGCAGGTGGTGACGATCTGGGCTGCA

GGAGCTGGGGCCACCCACAGCCCCCCTACCGACCTGGTGTGGAAGGCACA

GAACACCTGGGGCTGCGGGAACAGCCTGCGTACGGCTCTCATCAACTCCA

CTGGGGAAGAAGTGGCCATGCGCAAGCTGGTGCGCTCAGTGACTGTGGTT

GAGGACGACGAGGATGAGGATGGAGATGACCTGCTCCATCACCACCACGG

CTCCCACTGCAGCAGCTCGGGGACCCCGCTGAGTACAACCTGCGCTCGC

GCACCGTGCTGTGCGGGACCTGCGGGCAGCCTGCCGACAAGGCATCTGCC

AGCGGCTCAGGAGCCCAGGTGGGCGGACCCATCTCCTCTGGCTCTTCTGC

CTCCAGTGTCACGGTCACTCGCAGCTACCGCAGTGTGGGGGCAGTGGGG

GTGGCAGCTTCGGGGACAATCTGGTCACCCGCTCCTACCTCCTGGGCAAC

TCCAGCCCCCGAACCCAGAGCCCCAGAACTGCAGCATCATGTAA

The amino acid sequence that encodes one embodiment of Lamin A (ENSP00000357283) is referred to herein as SEQ ID No. 20 (previously referred to as SEQ ID No. 30 in patent application GB1701438.2), as follows:

[SEQ ID No. 20]
METPSQRRATRSGAQASSTPLSPTRITRLQEKEDLQELNDRLAVYIDRVR
SLETENAGLRLRITESEEVVSREVSGIKAAYEAELGDARKTLDSVAKERA
RLQLELSKVREEFKELKARNTKKEGDLIAAQARLKDLEALLNSKEAALST
ALSEKRTLEGELHDLRGQVAKLEAALGEAKKQLQDEMLRRVDAENRLQTM
KEELDFQKNIYSEELRETKRRHETRLVEIDNGKQREFESRLADALQELRA
QHEDQVEQYKKELEKTYSAKLDNARQSAERNSNLVGAAHEELQQSRIRID
SLSAQLSQLQKQLAAKEAKLRDLEDSLARERDTSRRLLAEKEREMAEMRA
RMQQQLDEYQELLDIKLALDMEIHAYRKLLEGEEERLRLSPSPTSQRSRG
RASSHSSQTQGGGSVTKKRKLESTESRSSFSQHARTSGRVAVEEVDEEGK
FVRLRNKSNEDQSMGNWQIKRQNGDDPLLTYRFPPKFTLKAGQVVTIWAA
GAGATHSPPTDLVWKAQNTWGCGNSLRTALINSTGEEVAMRKLVRSVTVV
EDDEDEDGDDLLHHHHGSHCSSSGDPAEYNLRSRTVLCGTCGQPADKASA
SGSGAQVGGPISSGSSASSVTVTRSYRSVGGSGGGSFGDNLVTRSYLLGN
SSPRTQSPQNCSIM

The nucleotide sequence that encodes one embodiment of Lamin C (ENST00000368301) is referred to herein as SEQ ID No. 21 (previously referred to as SEQ ID No. 31 in patent application GB1701438.2), as follows:

[SEQ ID No. 21]
ATGGAGACCCCGTCCCAGCGGCGCGCCACCCGCAGCGGGGCGCAGGCCAG
CTCCACTCCGCTGTCGCCCACCCGCATCACCCGGCTGCAGGAGAAGGAGG
ACCTGCAGGAGCTCAATGATCGCTTGGCGGTCTACATCGACCGTGTGCGC
TCGCTGGAAACGGAGAACGCAGGGCTGCGCCTTCGCATCACCGAGTCTGA
AGAGGTGGTCAGCCGCGAGGTGTCCGGCATCAAGGCCGCCTACGAGGCCG
AGCTCGGGGATGCCCGCAAGACCCTTGACTCAGTAGCCAAGGAGCGCGCC
CGCCTGCAGCTGGAGCTGAGCAAAGTGCGTGAGGAGTTTAAGGAGCTGAA
AGCGCGCAATACCAAGAAGGAGGGTGACCTGATAGCTGCTCAGGCTCGGC
TGAAGGACCTGGAGGCTCTGCTGAACTCCAAGGAGGCCGCACTGAGCACT
GCTCTCAGTGAGAAGCGCACGCTGGAGGGCGAGCTGCATGATCTGCGGGG
CCAGGTGGCCAAGCTTGAGGCAGCCCTAGGTGAGGCCAAGAAGCAACTTC
AGGATGAGATGCTGCGCGGGTGGATGCTGAGAACAGGCTGCAGACCATG
AAGGAGGAACTGGACTTCCAGAAGAACATCTACAGTGAGGAGCTGCGTGA
GACCAAGCGCCGTCATGAGACCCGACTGGTGGAGATTGACAATGGGAAGC
AGCGTGAGTTTGAGAGCCGGCTGGCGGATGCGCTGCAGGAACTGCGGGCC
CAGCATGAGGACCAGGTGGAGCAGTATAAGAAGGAGCTGGAGAAGACTTA
TTCTGCCAAGCTGGACAATGCCAGGCAGTCTGCTGAGAGGAACAGCAACC
TGGTGGGGGCTGCCCACGAGGAGCTGCAGCAGTCGCGCATCCGCATCGAC
AGCCTCTCTGCCCAGCTCAGCCAGCTCCAGAAGCAGCTGGCAGCCAAGGA
GGCGAAGCTTCGAGACCTGGAGGACTCACTGGCCCGTGAGCGGGACACCA
GCCGGCGGCTGCTGGCGGAAAAGGAGCGGGAGATGGCCGAGATGCGGGCA
AGGATGCAGCAGCAGCTGGACGAGTACCAGGAGCTTCTGGACATCAAGCT
GGCCCTGGACATGGAGATCCACGCCTACCGCAAGCTCTTGGAGGGCGAGG
AGGAGAGGCTACGCCTGTCCCCCAGCCCTACCTCGCAGCGCAGCCGTGGC
CGTGCTTCCTCTCACTCATCCCAGACACAGGGTGGGGGCAGCGTCACCAA
AAAGCGCAAACTGGAGTCCACTGAGAGCCGCAGCAGCTTCTCACAGCACG
CACGCACTAGCGGGCGCGTGGCCGTGGAGGAGGTGGATGAGGAGGGCAAG
TTTGTCCGGCTGCGCAACAAGTCCAATGAGGACCAGTCCATGGGCAATTG
GCAGATCAAGCGCCAGAATGGAGATGATCCCTTGCTGACTTACCGGTTCC
CACCAAAGTTCACCCTGAAGGCTGGGCAGGTGGTGACGATCTGGGCTGCA
GGAGCTGGGGCCACCCACAGCCCCCCTACCGACCTGGTGTGGAAGGCACA
GAACACCTGGGGCTGCGGGAACAGCCTGCGTACGGCTCTCATCAACTCCA
CTGGGGAAGAAGTGGCCATGCGCAAGCTGGTGCGCTCAGTGACTGTGGTT
GAGGACGACGAGGATGAGGATGGAGATGACCTGCTCCATCACCACCACGT
GAGTGGTAGCCGCCGCTGA

The amino acid sequence that encodes one embodiment of Lamin C (ENSP00000357284) is referred to herein as SEQ ID No. 22 (previously referred to as SEQ ID No. 32 in patent application GB1701438.2), as follows:

[SEQ ID No. 22]
METPSQRRATRSGAQASSTPLSPTRITRLQEKEDLQELNDRLAVYIDRVR
SLETENAGLRLRITESEEVVSREVSGIKAAYEAELGDARKTLDSVAKERA
RLQLELSKVREEFKELKARNTKKEGDLIAAQARLKDLEALLNSKEAALST
ALSEKRTLEGELHDLRGQVAKLEAALGEAKKQLQDEMLRRVDAENRLQTM
KEELDFQKNIYSEELRETKRRHETRLVEIDNGKQREFESRLADALQELRA
QHEDQVEQYKKELEKTYSAKLDNARQSAERNSNLVGAAHEELQQSRIRID
SLSAQLSQLQKQLAAKEAKLRDLEDSLARERDTSRRLLAEKEREMAEMRA
RMQQQLDEYQELLDIKLALDMEIHAYRKLLEGEEERLRLSPSPTSQRSRG
RASSHSSQTQGGGSVTKKRKLESTESRSSFSQHARTSGRVAVEEVDEEGK
FVRLRNKSNEDQSMGNWQIKRQNGDDPLLTYRFPPKFTLKAGQVVTIWAA
GAGATHSPPTDLVWKAQNTWGCGNSLRTALINSTGEEVAMRKLVRSVTVV
EDDEDEDGDDLLHHHHVSGSRR

B-type Lamins are categorised as Lamin B1 or Lamin B2. Lamin B1 is encoded by LMNB1 and Lamin B2 is encoded by LMNB2.

The nucleotide sequence that encodes one embodiment of LMNB1 can be found under genomic identifier ENSG00000113368.

The nucleotide sequence that encodes another embodiment of LMNB1 can be found under genomic identifier ENST00000261366, and is referred to herein as SEQ ID No. 23 (previously referred to as SEQ ID No. 34 in patent application GB1701438.2), as follows:

[SEQ ID No. 23]
ATGGCGACTGCGACCCCCGTGCCGCCGCGGATGGGCAGCCGCGCTGGCGG

CCCCACCACGCCGCTGAGCCCCACGCGCCTGTCGCGGCTCCAGGAGAAGG

AGGAGCTGCGCGAGCTCAATGACCGGCTGGCGGTGTACATCGACAAGGTG

CGCAGCCTGGAGACGGAGAACAGCGCGCTGCAGCTGCAGGTGACGGAGCG

CGAGGAGGTGCGCGGCCGTGAGCTCACCGGCCTCAAGGCGCTCTACGAGA

CCGAGCTGGCCGACGCGCGACGCGCGCTCGACGACACGGCCCGCGAGCGC

GCCAAGCTGCAGATCGAGCTGGGCAAGTGCAAGGCGGAACACGACCAGCT

GCTCCTCAACTATGCTAAGAAGGAATCTGATCTTAATGGCGCCCAGATCA

AGCTTCGAGAATATGAAGCAGCACTGAATTCGAAAGATGCAGCTCTTGCT

ACTGCACTTGGTGACAAAAAAAGTTTAGAGGGAGATTTGGAGGATCTGAA

GGATCAGATTGCCCAGTTGGAAGCCTCCTTAGCTGCAGCCAAAAAACAGT

TAGCAGATGAAACTTTACTTAAAGTAGATTTGGAGAATCGTTGTCAGAGC

CTTACTGAGGACTTGGAGTTTCGCAAAAGCATGTATGAAGAGGAGATTAA

CGAGACCAGAAGGAAGCATGAAACGCGCTTGGTAGAGGTGGATTCTGGGC

GTCAAATTGAGTATGAGTACAAGCTGGCGCAAGCCCTTCATGAGATGAGA

GAGCAACATGATGCCCAAGTGAGGCTGTATAAGGAGGAGCTGGAGCAGAC

TTACCATGCCAAACTTGAGAATGCCAGACTGTCATCAGAGATGAATACTT

CTACTGTCAACAGTGCCAGGGAAGAACTGATGGAAAGCCGCATGAGAATT

GAGAGCCTTTCATCCCAGCTTTCTAATCTACAGAAAGAGTCTAGAGCATG

TTTGGAAAGGATTCAAGAATTAGAGGACTTGCTTGCTAAAGAAAAAGACA

ACTCTCGTCGCATGCTGACAGACAAAGAGAGAGATGGCGGAAATAAGG

GATCAAATGCAGCAACAGCTGAATGACTATGAACAGCTTCTTGATGTAAA

GTTAGCCCTGGACATGGAAATCAGTGCTTACAGGAAACTCTTAGAAGGCG

AAGAAGAGAGGTTGAAGCTGTCTCCAAGCCCTTCTTCCCGTGTGACAGTA

TCCCGAGCATCCTCAAGTCGTAGTGTACGTACAACTAGAGGAAAGCGGAA

GAGGGTTGATGTGGAAGAATCAGAGGCGAGTAGTAGTGTTAGCATCTCTC

ATTCCGCCTCAGCCACTGGAAATGTTTGCATCGAAGAAATTGATGTTGAT

GGGAAATTTATCCGCTTGAAGAACACTTCTGAACAGGATCAACCAATGGG

AGGCTGGGAGATGATCAGAAAAATTGGAGACACATCAGTCAGTTATAAAT

ATACCTCAAGATATGTGCTGAAGGCAGGCCAGACTGTTACAATTTGGGCT

GCAAACGCTGGTGTCACAGCCAGCCCCCCAACTGACCTCATCTGGAAGAA

CCAGAACTCGTGGGGCACTGGCGAAGATGTGAAGGTTATATTGAAAAATT

CTCAGGGAGAGGAGGTTGCTCAAAGAAGTACAGTCTTTAAAACAACCATA

CCTGAAGAAGAGGAGGAGGAGGAAGAAGCAGCTGGAGTGGTTGTTGAGGA

AGAACTTTTCCACCAGCAGGGAACCCCAAGAGCATCCAATAGAAGCTGTG

CAATTATGTAA

The amino acid sequence that encodes one embodiment of Lamin B1 (ENSP00000261366) is referred to herein as SEQ ID No. 24 (previously referred to as SEQ ID No. 35 in patent application GB1701438.2), as follows:

[SEQ ID No. 24]
MATATPVPPRMGSRAGGPTTPLSPTRLSRLQEKEELRELNDRLAVYIDKV

RSLETENSALQLQVTEREEVRGRELTGLKALYETELADARRALDDTARER

AKLQIELGKCKAEHDQLLLNYAKKESDLNGAQIKLREYEAALNSKDAALA

TALGDKKSLEGDLEDLKDQIAQLEASLAAAKKQLADETLLKVDLENRCQS

LTEDLEFRKSMYEEEINETRRKHETRLVEVDSGRQIEYEYKLAQALHEMR

EQHDAQVRLYKEELEQTYHAKLENARLSSEMNTSTVNSAREELMESRMRI

ESLSSQLSNLQKESRACLERIQELEDLLAKEKDNSRRMLTDKEREMAEIR

DQMQQQLNDYEQLLDVKLALDMEISAYRKLLEGEEERLKLSPSPSSRVTV

SRASSSRSVRTTRGKRKRVDVEESEASSSVSISHSASATGNVCIEEIDVD

GKFIRLKNTSEQDQPMGGWEMIRKIGDTSVSYKYTSRYVLKAGQTVTIWA

ANAGVTASPPTDLIWKNQNSWGTGEDVKVILKNSQGEEVAQRSTVFKTTI

PEEEEEEEEAAGVVVEEELFHQQGTPRASNRSCAIM

The nucleotide sequence that encodes one embodiment of LMNB2 can be found under genomic identifier ENSG00000176619.

The nucleotide sequence that encodes another embodiment of LMNB2 (ENST00000325327) is referred to herein as SEQ ID No. 25 (previously referred to as SEQ ID No. 37 in patent application GB1701438.2), as follows:

[SEQ ID No. 25]
ATGAGCCCGCCGAGCCCGGGCCGCCGTCGGGAGCAGCGCAGGCCGCGAGC

CGCCGCCACCATGGCCACGCCGCTGCCCGGCCGCGCGGGCGGGCCCGCCA

CGCCGCTGTCGCCCACGCGCCTGTCGCGGCTGCAGGAGAAGGAGGAGCTG

CGCGAGCTCAACGACCGCCTGGCGCACTACATCGACCGCGTCCGCGCGCT

GGAGCTGGAGAACGACCGGCTCCTGCTCAAGATCTCAGAGAAGGAGGAGG

TGACCACGCGCGAGGTGAGTGGCATCAAGGCGCTGTACGAGTCGGAGCTG

GCCGATGCCCGGAGAGTCCTGGATGAGACGGCTCGAGAGCGTGCCCGGCT

GCAGATAGAGATTGGGAAGCTGAGGGCAGAGTTGGACGAGGTCAACAAGA

GCGCCAAGAAGAGGGAGGGCGAGCTTACGGTGGCCCAGGGCCGTGTGAAG

GACCTGGAGTCCCTGTTCCACCGGAGCGAGGTGGAGCTGGCAGCTGCCCT

CAGCGACAAGCGCGGCCTGGAGAGTGACGTGGCTGAGCTGCGGGCCCAGC

TGGCCAAGGCCGAGGACGGTCATGCAGTGGCCAAAAAGCAGCTGGAGAAG

GAGACGCTGATGCGTGTGGACCTGGAGAACCGCTGCCAGAGCCTGCAGGA

GGAGCTGGACTTCCGGAAGAGTGTGTTCGAGGAGGAGGTGCGGGAGACGC

GGCGGCGGCACGAGCGGCGCCTGGTGGAGGTGGACAGCAGCGGCAGCAG

GAGTACGACTTCAAGATGGCACAGGCGCTGGAGGAGCTGCGGAGCCAGCA

CGACGAGCAAGTGCGGCTCTACAAGCTGGAGCTGGAGCAGACCTACCAGG

CCAAGCTGGACAGCGCCAAGCTGAGCTCTGACCAGAACGACAAGGCGGCC

AGTGCGGCTCGCGAGGAGCTGAAGGAGGCCCGCATGCGCCTGGAGTCCCT

CAGCTACCAGCTCTCCGGCCTCCAGAAGCAGGCCAGTGCCGCTGAAGATC

GCATTCGGGAGCTGGAGGAGGCCATGGCCGGGGAGCGGGACAAGTTCCGG

AAGATGCTGGACGCCAAGGAGCAGGAGATGACGGAGATGCGGGACGTGAT

-continued
GCAGCAGCAGCTGGCCGAGTACCAGGAGCTGCTGGACGTGAAGCTGGCCC

TGGACATGGAGATCAACGCCTACCGGAAGCTCCTGGAGGGCGAGGAGGAG

AGGCTGAAGCTGTCCCCCAGCCCATCCTCGCGCGTCACCGTCTCACGAGC

CACCTCGAGCAGCAGCGGCAGCTTGTCCGCCACCGGGCGCCTGGGCCGCA

GTAAGCGGAAGCGGCTGGAGGTGGAGGAGCCCTTGGGCAGCGGCCCAAGC

GTCCTGGGCACGGGCACGGGTGGCAGCGGTGGCTTCCACCTGGCCCAGCA

GGCCTCGGCCTCGGGTAGCGTCAGCATCGAGGAGATCGACCTGGAGGGCA

AGTTTGTGCAGCTCAAGAACAACTCGGACAAGGATCAGTCTCTGGGGAAC

TGGAGAATCAAGAGGCAGGTCTTGGAGGGGAGGAGATCGCCTACAAGTT

CACGCCCAAGTACATCCTGCGCGCCGGCCAGATGGTCACGGTGTGGGCAG

CTGGTGCGGGGTGGCCCACAGCCCCCCCTCGACGCTGGTGTGGAAGGGC

CAGAGCAGCTGGGGCACGGGCGAGAGCTTCCGCACCGTCCTGGTTAACGC

GGATGGCGAGGAAGTGGCCATGAGGACTGTGAAGAAGTCCTCGGTGATGC

GTGAGAATGAGAATGGGGAGGAAGAGGAGGAGGAAGCCGAGTTTGGCGAG

GAGGATCTTTTCCACCAACAGGGGGACCCGAGGACCACCTCAAGAGGCTG

CTACGTGATGTGA

The amino acid sequence that encodes one embodiment of Lamin B2 (ENSP00000327054) is referred to herein as SEQ ID No. 26 (previously referred to as SEQ ID No. 38 in patent application GB1701438.2), as follows:

[SEQ ID No. 26]
MSPPSPGRRREQRRPRAAATMATPLPGRAGGPATPLSPTRLSRLQEKEEL

RELNDRLAHYIDRVRALELENDRLLLKISEKEEVTTREVSGIKALYESEL

ADARRVLDETARERARLQIEIGKLRAELDEVNKSAKKREGELTVAQGRVK

DLESLFHRSEVELAAALSDKRGLESDVAELRAQLAKAEDGHAVAKKQLEK

ETLMRVDLENRCQSLQEELDFRKSVFEEEVRETRRRHERRLVEVDSSRQQ

EYDFKMAQALEELRSQHDEQVRLYKLELEQTYQAKLDSAKLSSDQNDKAA

SAAREELKEARMRLESLSYQLSGLQKQASAAEDRIRELEEAMAGERDKFR

KMLDAKEQEMTEMRDVMQQQLAEYQELLDVKLALDMEINAYRKLLEGEEE

RLKLSPSPSSRVTVSRATSSSSGSLSATGRLGRSKRKRLEVEEPLGSGPS

VLGTGTGGSGGFHLAQQASASGSVSIEEIDLEGKFVQLKNNSDKDQSLGN

WRIKRQVLEGEEIAYKFTPKYILRAGQMVTVWAAGAGVAHSPPSTLVWKG

QSSWGTGESFRTVLVNADGEEVAMRTVKKSSVMRENENGEEEEEEAEFGE

EDLFHQQGDPRTTSRGCYVM

Thus, in one embodiment of the invention, the LINC complex that is disrupted in step (i) of the method of the invention may comprise a Lamin protein. The Lamin protein may be an A-type Lamin and/or a B-type Lamin. The B-type Lamin may be Lamin B1 or Lamin B2. Preferably, the Lamin protein is a Lamin A, Lamin C and/or Lamin B1. The Lamin protein may be encoded by a nucleotide sequence substantially as set out under genomic identifiers ENSG00000160789, ENSG00000113368, ENSG00000176619 and/or in SEQ ID Nos. 19, 21, 23 and/or 25, or a variant or fragment thereof. Preferably, the Lamin protein is encoded by a nucleotide sequence substantially as set out under genomic identifiers ENSG00000160789, ENSG00000113368, ENSG00000176619 and/or in SEQ ID No.19, 21, 23 and/or 25 or a variant or fragment thereof. The Lamin protein comprises an amino acid sequence substantially as set out in SEQ ID Nos. 20, 22, 24 and/or 26, or a variant or fragment thereof. Preferably, the Lamin protein comprises an amino acid sequence substantially as set out in SEQ ID No. 20, 22, 24 and/or 26, or a variant or fragment thereof. The Lamin protein may be encoded by LMNA, LMNB1 and/or LMNB2, or a variant or fragment thereof. Preferably, the Lamin protein is encoded by LMNA and/or LMNB1, or a variant or fragment thereof.

Thus, step (i) of the method may comprise disrupting the translation or function of one or more of the above LINC proteins, or the transcription or function of one or more of the above nucleotides that encode a LINC complex protein, such as a SUN protein, a Nesprin protein or a Lamin protein.

Although a single protein complex (i.e. the LINC complex) acts as an intracellular cellular "switch" that physically links cellular nuclei to their extracellular environment, the constituents of the LINC complex may vary in different tissue or cell types. For example, in keratinocytes, giant Nesprin-2 is the dominant isoform of nesprin. Giant Nesprin-2 commonly binds to SUN1 and SUN2. Preferably, therefore, the LINC complex that is disrupted in step (i) comprises giant Nesprin-2 and SUN1 and/or SUN2.

The complexity of the LINC complex may also be increased by virtue of the fact that LINC complex proteins may bind to each other with a 3:3 stoichiometry. Preferably, the LINC complex that is disrupted in step (i) comprises a Nesprin and a SUN protein. Preferably the Nesprin protein comprises a KASH domain and the SUN protein comprises a SUN domain. Even more preferably, the Nesprins and SUN proteins are bound to each other with a 3:3 stoichiometry to form a hexameric complex. Most preferably, the Nesprins comprise a KASH domain and the SUN proteins comprise a SUN domain. Therefore, the LINC complex that is disrupted in step (i) may be a hexameric complex of three SUN proteins and three Nesprin proteins. Nesprin paralogues bind promiscuously to SUN-domains, which are essential for Nesprin recruitment to the outer nuclear membrane. SUN1 and SUN2 proteins play partially redundant roles and interact with each other via their luminal coiled-coil segments, forming heteromeric stable complexes. Therefore, it is believed that LINC hexamers may comprise mixed Nesprin and SUN-domain paralogue combinations. Thus, in one embodiment, the hexameric complex that is disrupted in step (i) of the method may be heteromeric (i.e. comprise two or three different subtypes of a SUN protein and/or two or three different subtypes of Nesprin protein).

In another embodiment, the hexameric LINC complex that is disrupted in step (i) of the method may be a homomeric complex of SUN proteins (i.e. comprise three identical subtypes of SUN) or a homomeric complex of Nesprin proteins (i.e. comprise three identical subtypes of Nesprin). Preferably, the LINC complex is a heteromeric or homomeric complex of Nesprins that each comprise a Nesprin with a KASH domain, and/or SUN proteins that each comprise a SUN domain.

The presence of multiple subtypes and isoforms of proteins that comprise a SUN-domain or a KASH-domain suggests that the LINC complex may be a diverse and multi-functional complex. Given that several core constituents of the LINC complex exhibit cell-type and tissue specificity, distinct LINC complexes can be assumed to form that may perform specific tasks to accommodate the physiology requirements of the respective cell and tissue.

Preferably, however, the LINC complex that is disrupted in step (i) of the method comprises (1) a Nesprin protein, which, via its KASH domain, is bound to the SUN domain of a SUN protein; and/or (2) a SUN protein, which is bound to a lamin protein.

Most preferably, the LINC complex comprises a Nesprin protein, which, via its KASH domain, is bound to the SUN domain of a SUN protein.

Accordingly, therefore, the agent that disrupts the LINC complex may be an agent that:
(i) reduces or is configured to reduce the concentration of a LINC complex protein compared to the concentration of the LINC complex protein in the absence of the agent (for example, by inhibiting the transcription of a nucleotide encoding a LINC complex protein and/or inhibiting translation of an RNA molecule encoding a LINC complex protein);
(ii) inhibits or is configured to inhibit the binding of one LINC complex protein to another LINC complex protein; or
(iii) promotes or is configured to promote degradation of the LINC complex or one or more of the LINC complex proteins.

In one embodiment, an agent that inhibits the concentration of a LINC complex protein is a Non-steroidal anti-inflammatory drug (NSAID). The NSAID may inhibit the concentration of Nesprin proteins. Preferably, the NSAID inhibits the concentration of Nesprin-2. The NSAID may be an agent that inhibits the enzyme activity of cyclooxygenase 1 or 2 (COX1 or COX2), such as ibuprofen, naproxen, indomethacin and aspirin. Preferably, the NSAID is an agent that inhibits the enzyme activity of COX1, such as sullindac sulphide.

In one embodiment, an agent that inhibits binding of one LINC complex protein to another LINC complex protein may be a pharmacological agent, such as a small molecule, a peptide, an antibody or an intrabody. An agent that disrupts the LINC complex may be an agent that inhibits or is configured to inhibit binding of a Nesprin protein to a SUN protein, preferably by inhibiting binding of a KASH domain to a SUN domain. Preferably the agent disrupts binding of KASH domain to a SUN domain. The agent may therefore be a modified Nesprin protein that does not comprise a KASH domain, or a variant or a fragment thereof. The modified Nesprin may comprise an N-terminal F-actin binding domain (ABD), a long spectrin repeat containing region and a C-terminal transmembrane domain, or a variant or a fragment thereof. The agent may be an antibody or an intrabody that binds to the KASH domain of a Nesprin. Preferably, the modified Nesprin protein is expressed in the cytoplasm.

In one embodiment, the agent may be a modified Nesprin that consists of a KASH domain. Therefore, the modified Nesprin may not comprise an N-terminal F-actin binding domain (ABD), a long spectrin repeat containing region and/or a C-terminal transmembrane domain. Preferably, the modified Nesprin is expressed or present in the nuclear envelope.

In one embodiment, the agent may be a modified SUN protein that comprises a SUN domain or the SUN domain together with other regions located in the perinuclear space, such as the coiled-coil domain. Therefore, the modified SUN protein does not comprise any domains located in the nucleoplasm, such as the N-terminal domain. Thus, the modified SUN protein may comprise a SUN domain, or a SUN domain and coiled-coil domain, or a variant or a fragment thereof. Preferably, the modified SUN protein is expressed or present in the perinuclear envelope/space. Preferably, the agent or modified SUN protein disrupts binding of SUN proteins, which comprise a SUN domain, to the KASH domain of Nesprins. In a preferred embodiment, the modified SUN protein is referred to herein as SEQ ID No. 27 (previously referred to as SEQ ID No. 39 in patent application GB1701438.2), as follows:

[SEQ ID No. 27]
VSLWGQGNFFSLLPVLNWTAMQPTQRVDDSKGMHRPGPLPPSPPPKVDHK

ASQWPQESDMGQKVASLSAQCHNHDERLAELTVLLQKLQIRVDQVDDGRE

GLSLWVKNVVGQHLQEMGTIEPPDAKTDFMTFHHDHEVRLSNLEDVLRKL

TEKSEAIQKELEETKLKAGSRDEEQPLLDRVQHLELELNLLKSQLSDWQH

LKTSCEQAGARIQETVQLMFSEDQQGGSLEWLLEKLSSRFVSKDELQVLL

HDLELKLLQNITHHITVTGQAPTSEAIVSAVNQAGISGITEAQAHIIVNN

ALKLYSQDKTGMVDFALESGGGSILSTRCSETYETKTALLSLFGVPLWYF

SQSPRVVIQPDIYPGNCWAFKGSQGYLVVRLSMKIYPTTFTMEHIPKTLS

PTGNISSAPKDFAVYGLETEYQEEGQPLGRFTYDQEGDSLQMFHTLERPD

QAFQIVELRVLSNWGHPEYTCLYRFRVHGEPIQ

Thus, the agent may comprise an amino acid sequence substantially as set out in SEQ ID No. 26, or a variant or fragment thereof.

In one embodiment, the agent may be a modified SUN protein that consists of a SUN domain. Thus, the modified SUN protein may comprise a coiled-coil domain, a transmembrane domain and/or an N-terminal domain, or a variant or a fragment thereof. Preferably, the modified SUN protein is expressed or present in the perinuclear envelope and the nucleoplasm. Preferably, the agent or modified SUN protein disrupts binding of SUN proteins, which comprise a SUN domain, to the KASH domain of Nesprins.

In another embodiment, the agent that disrupts the LINC complex may be a gene-silencing molecule. A gene-silencing molecule is any molecule that interferes with the transcription a nucleotide (gene) encoding a protein of the LINC complex. Such molecules include, but are not limited to, RNAi molecules, including siNA, siRNA, miRNA, ribozymes and antisense molecules. Alternatively, the agent may be any molecule that interferes with the translation of an RNA encoding a protein of a LINC complex.

The skin cell used of step (i) of the method according to the invention may be a primary cell derived from skin tissue or a cell from ex vivo tissue. The skin cell of step (i) of the method according to the invention may be a mammalian cell or a human cell. The skin cell of step (i) of the method according to the invention may be an immortalised cell that has been derived from skin tissue. The skin cell of step (i) of the method according to the invention may be derived from a layer of skin. The layer of skin may be the epidermis, the dermis or the hypodermis. Preferably, the skin cell of step (i) of the method according to the invention is derived from the epidermis. The skin cell of step (i) of the method according to the invention may be a fibroblast, a keratinocyte, a melanocyte, a Merkel cell or a Langerhans cell. Most preferably, the cell is a keratinocyte.

The agent may be introduced into the cell by contacting the cell with the agent, intracellular injection, electroporation, transgenic expression or any other known suitable technique.

It will be appreciated that conditions for culturing cells in vitro or ex vivo so that they develop into a tissue will vary depending on the type of cell being cultured. The skilled person therefore would appreciate that if, for example, culturing a keratinocyte such that it develops into epidermal tissue, the keratinocytes may need to be cultured under conditions that promote proliferation and differentiation. In vitro or ex vitro culture conditions that promote proliferation of keratinocytes include 37° C., 5% $CO_2$ and culture media. In vitro or ex vitro culture conditions that promote differentiation of keratinocytes into skin tissue include culturing the keratinocytes on the surface of culture media at 37° C. and 5% $CO_2$.

Step (ii) of the method (i.e. culturing step (ii)), which is used to induce proliferation of the cell, may comprise culturing the cell at 34 to 39° C. or 35 to 38° C. Preferably, the culturing step comprises culturing the cell at about 37° C. The cell may be cultured for at least 6, 12, 18, 24, 36, 48, 96 or 168 hours. Preferably, the cell is cultured for at least 48 hours. The cell may be cultured at 35 to 38° C. for at least 6, 12, 18, 24, 36, 48, 96 or 168 hours. Most preferably, the cell is cultured at 35 to 38° C. for at least 48 hours.

Step (iii) of the method (i.e. culturing step (iii)), which is used to induce differentiation of the cells, may comprise culturing the cells at 34 to 39° C. or 35 to 38° C. Preferably, the culturing step comprises culturing the cells at about 37° C. The cells may be cultured for at least 6, 12, 18, 24, 36, 48, 96 or 168 hours. Preferably, the cells are cultured for at least 48 hours. The cells may be cultured at 35 to 38° C. for at least 6, 12, 18, 24, 36, 48, 96 or 168 hours. Most preferably, the cells are cultured at 35 to 38° C. for at least 48 hours.

Preferably, the culture media and the cell are disposed on the surface of the substrate. The substrate may be an insert or mesh that can be placed in a culture plate. The insert or mesh may be made of plastic. Preferably, the insert is a porous two-dimensional insert or a three-dimensional mesh. The advantage of using a porous insert or a three-dimensional mesh is that it enables the cell/cells to be fed with culture media disposed in the holes of the insert or mesh. Another advantage of the porous substrate or 3D mesh is that it enables the proliferating cells to form layers of cells.

Removing culture media from the cells such that they are disposed in the air-media interface, arrests proliferation and induces expression of proteins found in terminally differentiated cells. For example, keratinocytes stop expressing proteins that are responsible for attachment to the basement membrane (hemidesmosomes), they remodel their cell-to-cell junctions (desmosomes), they remodel their cytoskeleton (in particular, they stop expression keratin-5/-14 and start expressing keratin-1/-10) and they express proteins that will form a highly crosslinked protein-lipid structure (the cornified envelope). This whole process leads to the loss of cell nuclei and the formation of the stratum corneum, which is the uppermost layer of the skin. This layer of skin comprises dead cells that seal off the epidermis from the outside. The inventors have used keratin-10 as a biomarker of differentiated cells. As shown in FIG. 9, keratin-10 staining is more pronounced in the cells comprising a LINC mutant than wild type cells. Hence, ex vivo or in vitro disruption of the LINC complex encourages cellular differentiation.

According to a second aspect, there is provided a skin tissue obtained or obtainable by the method according to the first aspect.

According to a third aspect, there is provided a kit for creating a skin tissue, the kit comprising a skin cell and an agent that disrupts the LINC complex.

In a fourth aspect, there is provided use of an agent that disrupts the LINC complex in a skin cell to create a skin tissue.

In a fifth aspect, there is provided a method of testing the effects of a test compound on the properties of a skin tissue, the method comprising contacting a skin tissue according to the second aspect or a skin tissue created by the method according to the first aspect with a test compound and measuring the effects of the test compound on the properties of the skin tissue.

The properties of the skin tissue that are measured in the method according to the fifth aspect may be cell identity, cell proliferation, cell differentiation, cell longevity, cell stratification (layers formed), cell signalling, cell behaviour, cell architecture, barrier function, cell/tissue stiffness, skin corrosion, electrical resistance and/or cornified envelope formation.

The way in which the properties of the skin tissue are measured, will be determined by the properties being measured. The skilled person would appreciate that cell identity, cell proliferation, cell differentiation, cell longevity, cell stratification (layers formed), cell signalling, cell behaviour, cell architecture, barrier function, cell/tissue stiffness, skin corrosion, electrical resistance and/or cornified envelope formation will be measured using techniques known in the art.

The LINC complex plays a key role in premature ageing because (i) mutations in Lamin A are known to cause premature ageing diseases, such as Hutchison-Gilford Progeria Syndrome (HGPS), and (ii) modulating levels of SUN1 and Nesprin ameliorates progeria phenotypes both in vitro and in vivo. Thus, LINC complex biology can be harnessed to develop potent anti-ageing and regenerative medicine technologies.

Hence, in a sixth aspect, there is provided a method of identifying a skin-softening compound, the method comprising:-
1. contacting, in the presence of a test compound, a SUN domain with a KASH domain; and
2. detecting binding between the SUN domain and the KASH domain, wherein an alteration in binding as compared to a control is an indicator that the test compound is a candidate skin-softening compound that disrupts a LINC complex comprising SUN domain and a KASH domain.

The alteration may be increased binding or reduced binding. Preferably, the alteration is increased binding between the SUN domain and the KASH domain, or reduced binding between the SUN domain and the KASH domain. The increased binding may be at least a 10%, 15%, 25%, 35%, 45%, 50%, 55%, 60%, 65%, 70%, 75%, 80%, 85%, 90%, 95%, or 100% increase. The reduced binding may be at least a 10%, 15%, 25%, 35%, 45%, 50%, 55%, 60%, 65%, 70%, 75%, 80%, 85%, 90%, 95% or 100% reduction.

The skilled person would appreciate that the binding of a SUN domain to a KASH domain may be detected using a variety of techniques known in the art, which include, but are not limited to, protein complex immunoprecipitation, Bimolecular Fluorescence complementation, Affinity electrophoresis, Immunoelectrophoresis, chemical cross linking, Proximity ligation assay and FRET.

In a seventh aspect, there is provided a method of making cells softer, the method comprising contacting a skin cell with an agent that disrupts the LINC complex.

The cells are made softer by at least 10%, 15%, 25%, 35%, 45%, 50%, 55%, 60%, 65%, 70%, 75%, 80%, 85%, 90%, 95%, 100%, 150%, 200% or 300% compared to the softness of the wild-type cells.

Advantageously, softening cells improves their ability to form cellular layers.

In an eighth aspect, there is provided use of an agent that disrupts the LINC complex in an anti-ageing skin composition.

Preferably, the agent does not disrupt a LINC complex comprising Nesprin-2. Most preferably, the agent disrupts a LINC complex comprising SUN1.

The use may comprise contacting the agent with a pharmaceutical acceptable vehicle.

A "pharmaceutically acceptable vehicle" as referred to herein, is any known compound or combination of known compounds that are known to those skilled in the art to be useful in formulating pharmaceutical compositions.

In one embodiment, the pharmaceutically acceptable vehicle may be a solid, and the composition may be in the form of a powder or tablet. A solid pharmaceutically acceptable vehicle may include one or more substances which may also act as flavouring agents, lubricants, solubilisers, suspending agents, dyes, fillers, glidants, compression aids, inert binders, sweeteners, preservatives, dyes, coatings, or tablet-disintegrating agents. The vehicle may also be an encapsulating material. In powders, the vehicle is a finely divided solid that is in admixture with the finely divided active agents (i.e. the agent referred to in the first, third and fifth to seventh and eighth aspects) according to the invention. In tablets, the active compound may be mixed with a vehicle having the necessary compression properties in suitable proportions and compacted in the shape and size desired. The powders and tablets preferably contain up to 99% of the active compound. Suitable solid vehicles include, for example calcium phosphate, magnesium stearate, talc, sugars, lactose, dextrin, starch, gelatin, cellulose, polyvinylpyrrolidine, low melting waxes and ion exchange resins. In another embodiment, the pharmaceutical vehicle may be a gel and the composition may be in the form of a cream or the like.

However, the pharmaceutical vehicle may be a liquid, and the pharmaceutical composition is in the form of a solution. Liquid vehicles are used in preparing solutions, suspensions, emulsions, syrups, elixirs and pressurized compositions. The compound according to the invention may be dissolved or suspended in a pharmaceutically acceptable liquid vehicle such as water, an organic solvent, a mixture of both or pharmaceutically acceptable oils or fats. The liquid vehicle can contain other suitable pharmaceutical additives such as solubilisers, emulsifiers, buffers, preservatives, sweeteners, flavouring agents, suspending agents, thickening agents, colours, viscosity regulators, stabilizers or osmo-regulators. Suitable examples of liquid vehicles for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the vehicle can also be an oily ester such as ethyl oleate and isopropyl myristate. Sterile liquid vehicles are useful in sterile liquid form compositions for parenteral administration. The liquid vehicle for pressurized compositions can be a halogenated hydrocarbon or other pharmaceutically acceptable propellant.

Liquid pharmaceutical compositions, which are sterile solutions or suspensions, can be utilized by, for example, intramuscular, intrathecal, epidural, intraperitoneal, intravenous and particularly subcutaneous injection. The compound may be prepared as a sterile solid composition that may be dissolved or suspended at the time of administration using sterile water, saline, or other appropriate sterile injectable medium.

The compound and compositions of the invention may be administered in the form of a sterile solution or suspension containing other solutes or suspending agents (for example, enough saline or glucose to make the solution isotonic), bile salts, acacia, gelatin, sorbitan monoleate, polysorbate 80 (oleate esters of sorbitol and its anhydrides copolymerized with ethylene oxide) and the like. The compounds used according to the invention can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

The cell in the kit of the third aspect or the method of the seventh aspect may be a cell as defined in the method according to the first aspect. The agent in the kit of the third aspect or the method according to the seventh aspect may be an agent as defined according to the method of the first aspect.

It will be appreciated that the invention extends to any nucleic acid or peptide or variant, derivative or analogue thereof, which comprises substantially the amino acid or nucleic acid sequences of any of the sequences referred to herein, including variants or fragments thereof. The terms "substantially the amino acid/nucleotide/peptide sequence", "variant" and "fragment", can be a sequence that has at least 40% sequence identity with the amino acid/nucleotide/peptide sequences of any one of the sequences referred to herein, for example 40% identity with the nucleic acids or polypeptides described herein.

Amino acid/polynucleotide/polypeptide sequences with a sequence identity which is greater than 50%, more preferably greater than 65%, 70%, 75%, and still more preferably greater than 80% sequence identity to any of the sequences referred to are also envisaged. Preferably, the amino acid/polynucleotide/polypeptide sequence has at least 85% identity with any of the sequences referred to, more preferably at least 90%, 92%, 95%, 97%, 98%, and most preferably at least 99% identity with any of the sequences referred to herein.

The skilled technician will appreciate how to calculate the percentage identity between two amino acid/polynucleotide/polypeptide sequences. In order to calculate the percentage identity between two amino acid/polynucleotide/polypeptide sequences, an alignment of the two sequences must first be prepared, followed by calculation of the sequence identity value. The percentage identity for two sequences may take different values depending on:- (i) the method used to align the sequences, for example, ClustalW, BLAST, FASTA, Smith-Waterman (implemented in different programs), or structural alignment from 3D comparison; and (ii) the parameters used by the alignment method, for example, local vs global alignment, the pair-score matrix used (e.g. BLOSUM62, PAM250, Gonnet etc.), and gap-penalty, e.g. functional form and constants.

Having made the alignment, there are many different ways of calculating percentage identity between the two sequences. For example, one may divide the number of identities by: (i) the length of shortest sequence; (ii) the length of alignment; (iii) the mean length of sequence; (iv) the number of non-gap positions; or (iv) the number of equivalenced positions excluding overhangs. Furthermore, it will be appreciated that percentage identity is also strongly length dependent. Therefore, the shorter a pair of sequences is, the higher the sequence identity one may expect to occur by chance.

Hence, it will be appreciated that the accurate alignment of protein or DNA sequences is a complex process. The popular multiple alignment program ClustalW (Thompson et al., 1994, Nucleic Acids Research, 22, 4673-4680; Thompson et al., 1997, Nucleic Acids Research, 24, 4876-4882) is a preferred way for generating multiple alignments of proteins or DNA in accordance with the invention. Suitable parameters for ClustalW may be as follows: For DNA alignments: Gap Open Penalty=15.0, Gap Extension Penalty=6.66, and Matrix=Identity. For protein alignments: Gap Open Penalty=10.0, Gap Extension Penalty=0.2, and Matrix=Gonnet. For DNA and Protein alignments: END-GAP=−1, and GAPDIST=4. Those skilled in the art will be aware that it may be necessary to vary these and other parameters for optimal sequence alignment.

Preferably, calculation of percentage identities between two amino acid/polynucleotide/polypeptide sequences may then be calculated from such an alignment as (N/T)*100, where N is the number of positions at which the sequences share an identical residue, and T is the total number of positions compared including gaps but excluding overhangs. Hence, a most preferred method for calculating percentage identity between two sequences comprises (i) preparing a sequence alignment using the ClustalW program using a suitable set of parameters, for example, as set out above; and (ii) inserting the values of N and T into the following formula:- Sequence Identity=(N/T)*100.

Alternative methods for identifying similar sequences will be known to those skilled in the art. For example, a substantially similar nucleotide sequence will be encoded by a sequence which hybridizes to any sequences referred to herein or their complements under stringent conditions. By stringent conditions, we mean the nucleotide hybridises to filter-bound DNA or RNA in 3x sodium chloride/sodium citrate (SSC) at approximately 45° C. followed by at least one wash in 0.2×SSC/0.1% SDS at approximately 20-65° C. Alternatively, a substantially similar polypeptide may differ by at least 1, but less than 5, 10, 20, 50 or 100 amino acids from the polypeptide sequences described herein.

Due to the degeneracy of the genetic code, it is clear that any nucleic acid sequence described herein could be varied or changed without substantially affecting the sequence of the protein encoded thereby, to provide a variant thereof. Suitable nucleotide variants are those having a sequence altered by the substitution of different codons that encode the same amino acid within the sequence, thus producing a silent change. Other suitable variants are those having homologous nucleotide sequences but comprising all, or portions of, sequence, which are altered by the substitution of different codons that encode an amino acid with a side chain of similar biophysical properties to the amino acid it substitutes, to produce a conservative change. For example small non-polar, hydrophobic amino acids include glycine, alanine, leucine, isoleucine, valine, proline, and methionine.

Large non-polar, hydrophobic amino acids include phenylalanine, tryptophan and tyrosine. The polar neutral amino acids include serine, threonine, cysteine, asparagine and glutamine. The positively charged (basic) amino acids include lysine, arginine and histidine. The negatively charged (acidic) amino acids include aspartic acid and glutamic acid. It will therefore be appreciated which amino acids may be replaced with an amino acid having similar biophysical properties, and the skilled technician will know the nucleotide sequences encoding these amino acids.

All of the features described herein (including any accompanying claims, abstract and drawings), and/or all of the steps of any method or process so disclosed, may be combined with any of the above aspects in any combination, except combinations where at least some of such features and/or steps are mutually exclusive.

BRIEF DESCRIPTION OF THE DRAWINGS

For a better understanding of the invention, and to show how embodiments of the same may be carried into effect, reference will now be made, by way of example, to the accompanying Figures, in which:-

Figure 5A:
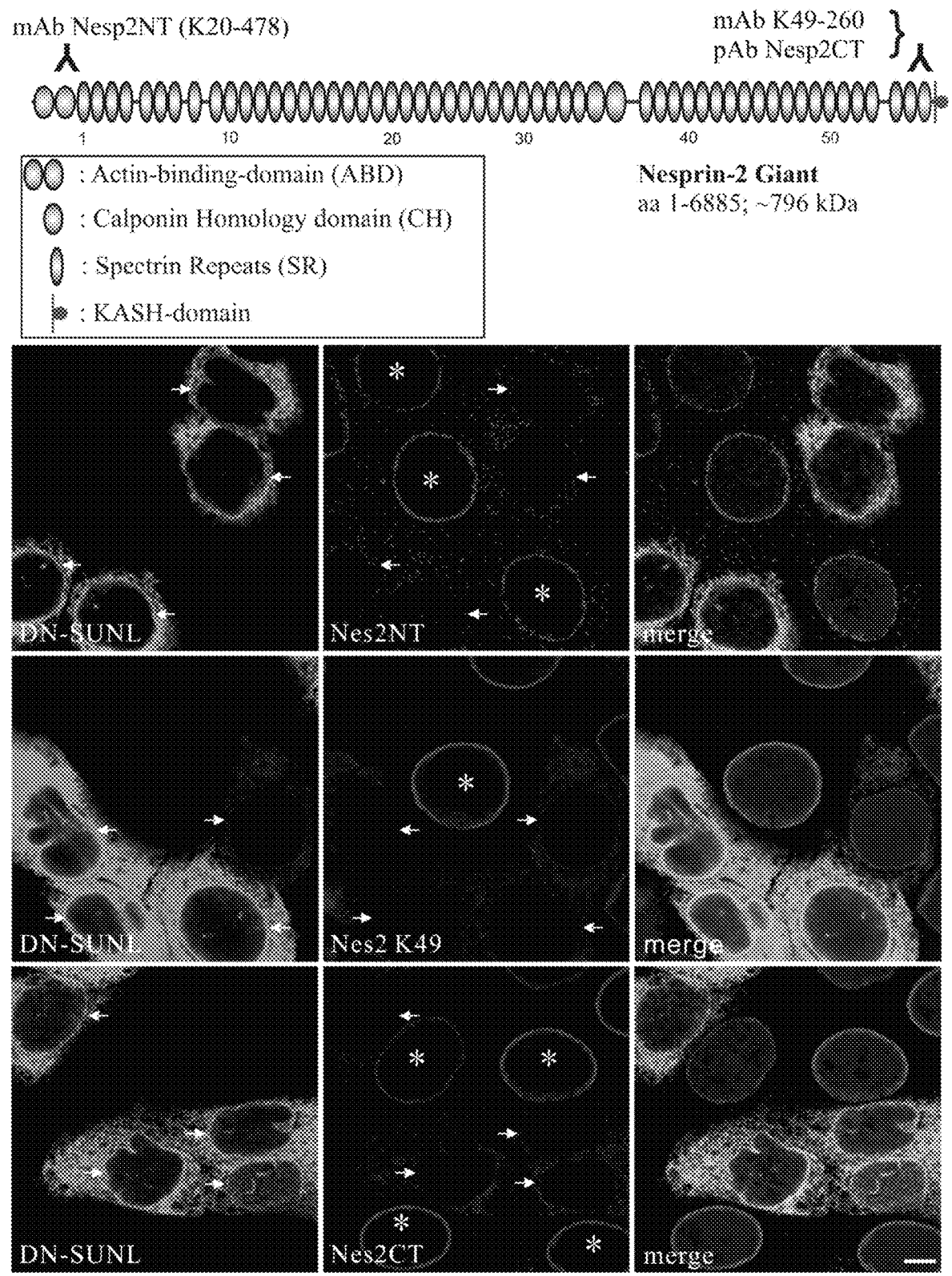
Figure 5B:
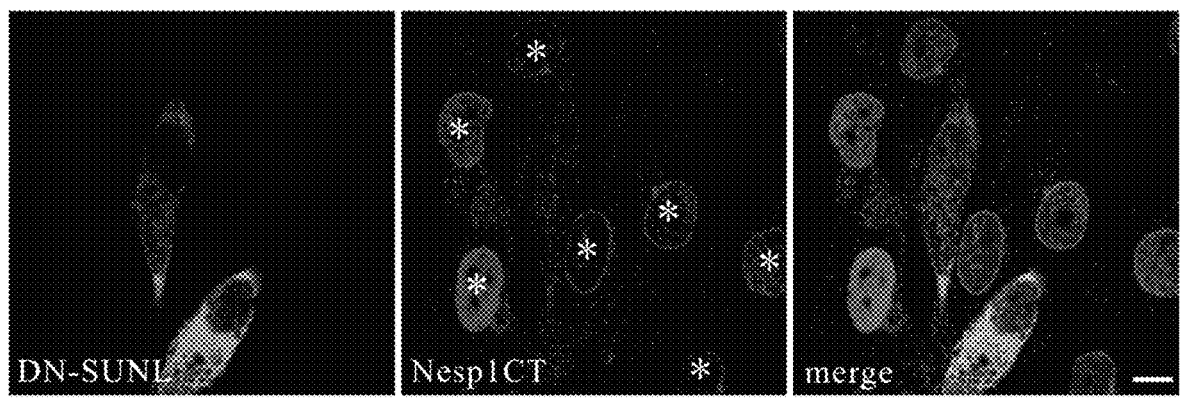
Figure 5C:
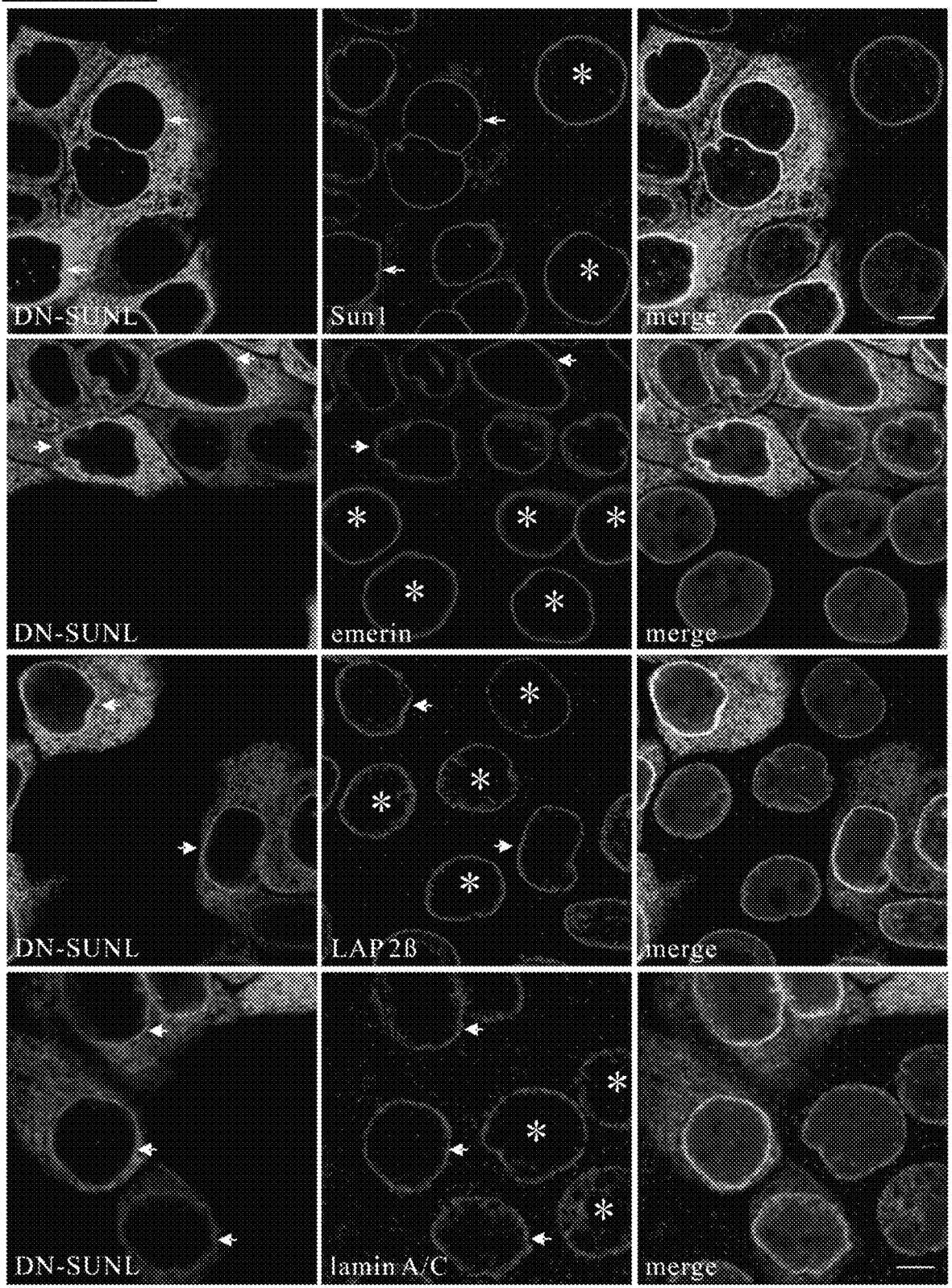
Figure 6A:
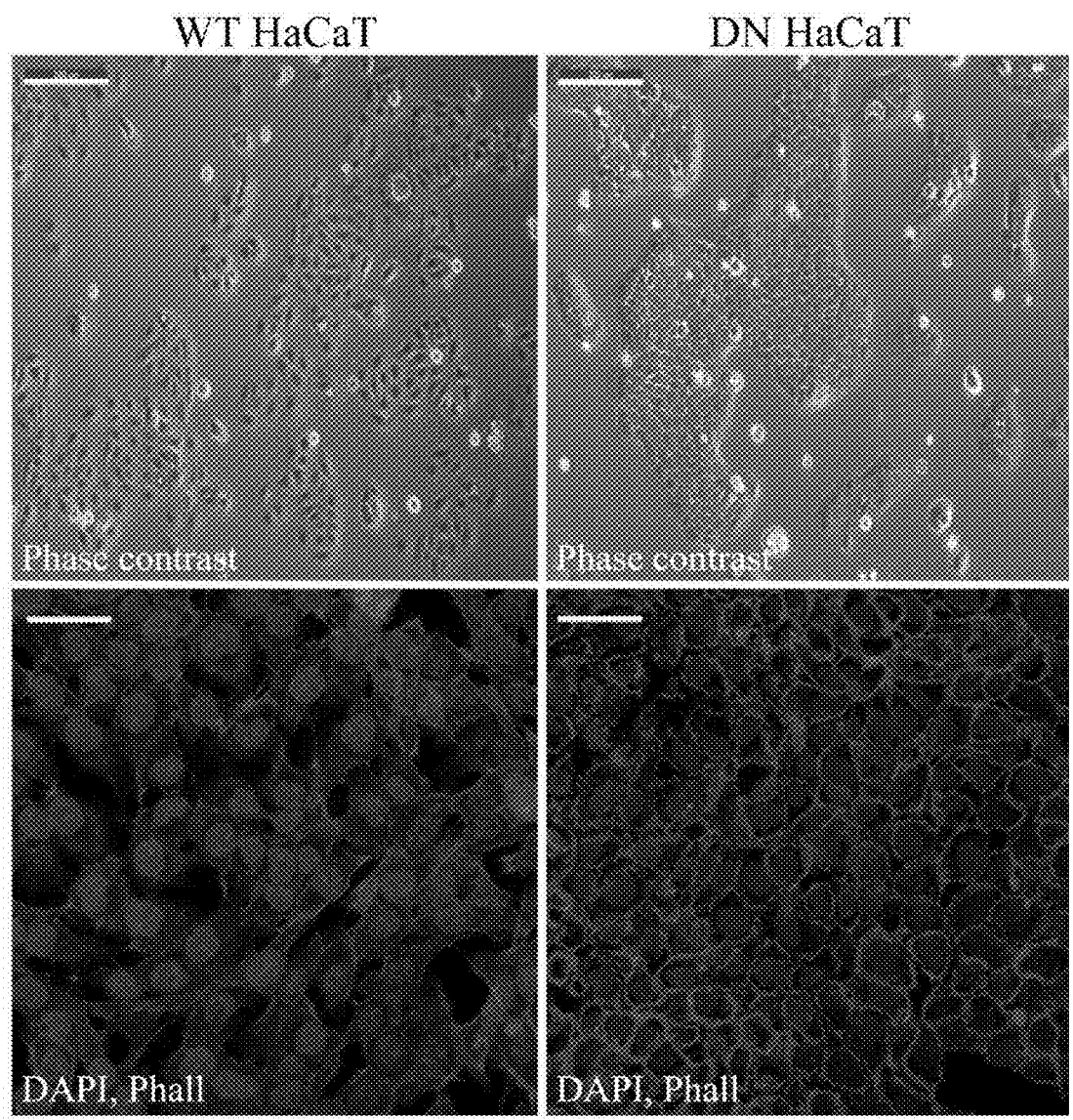
Figure 7A:
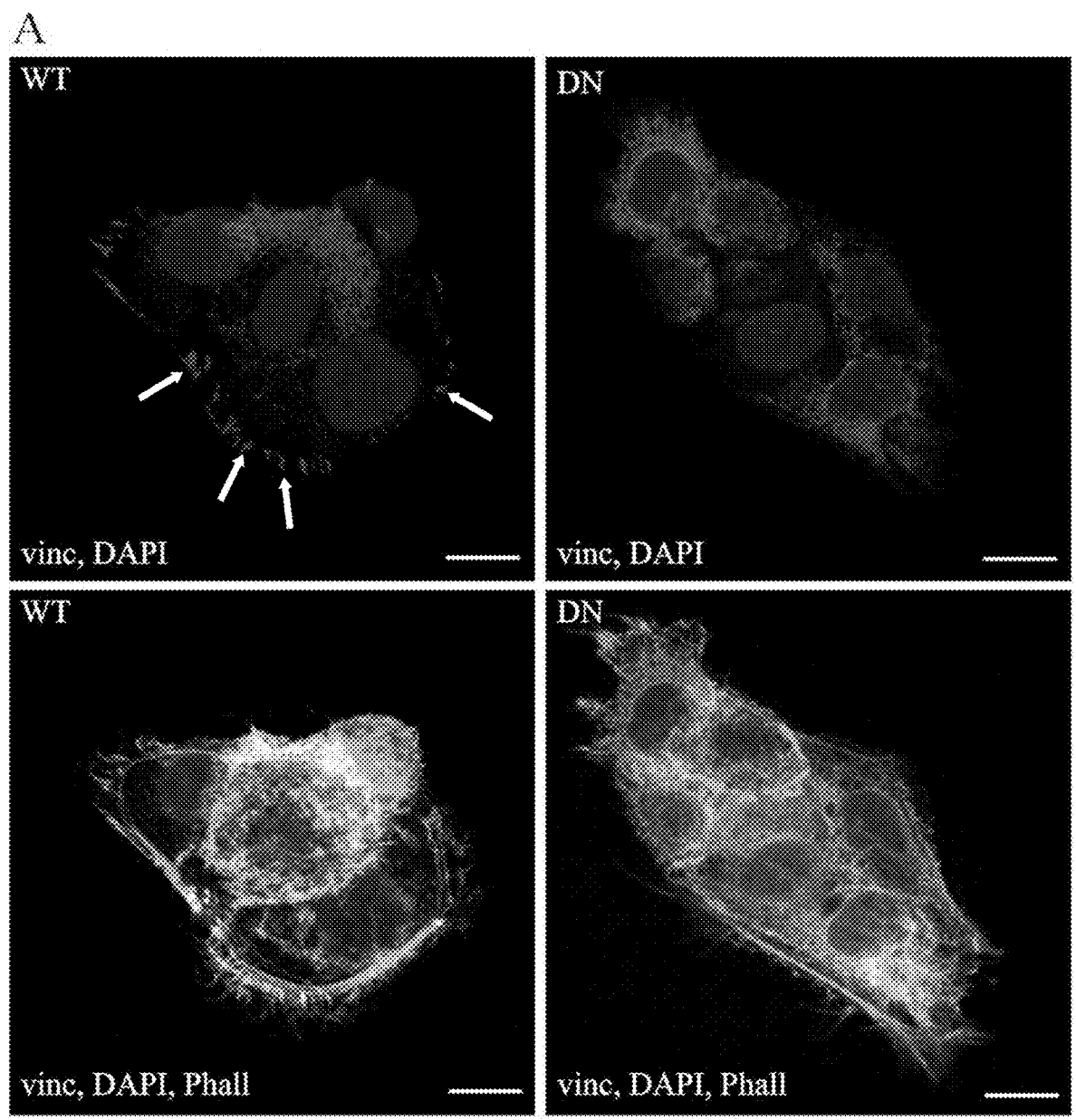
Figure 9:
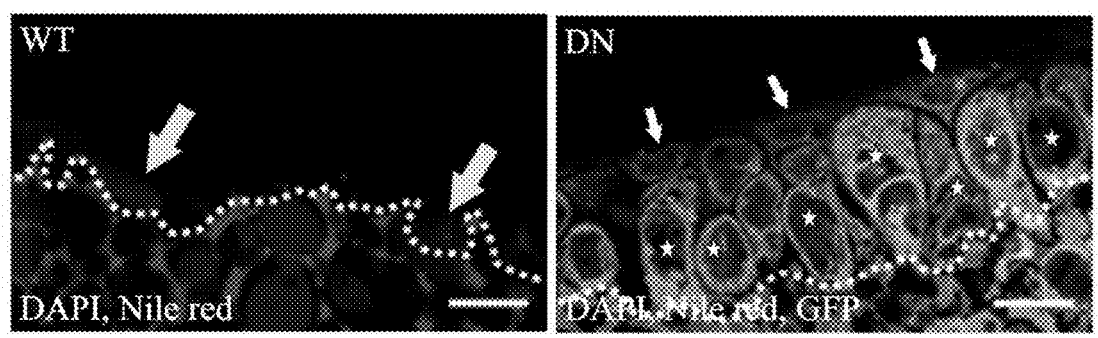
Figure 9:
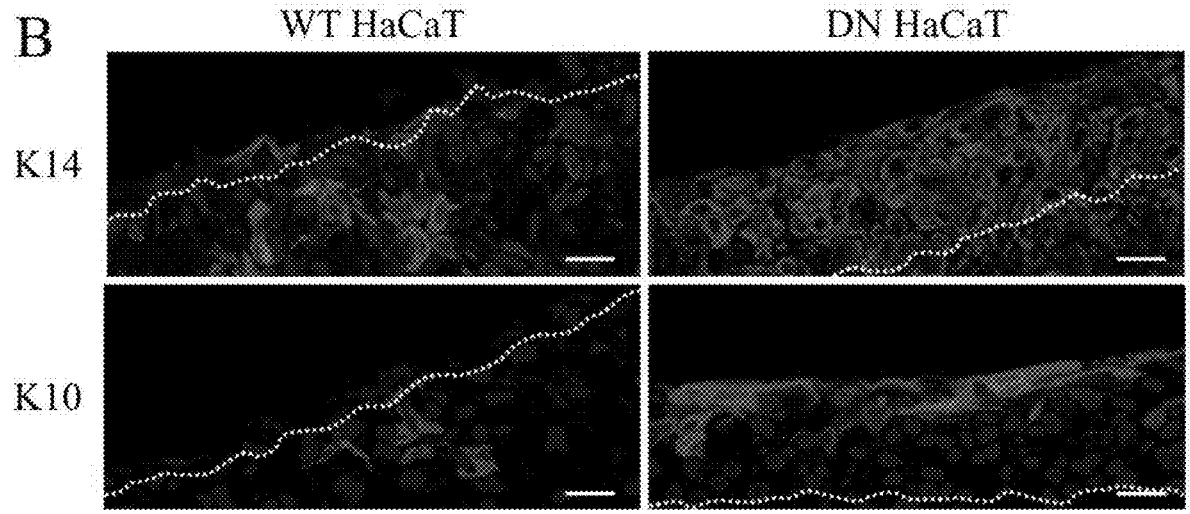
Figure 10:
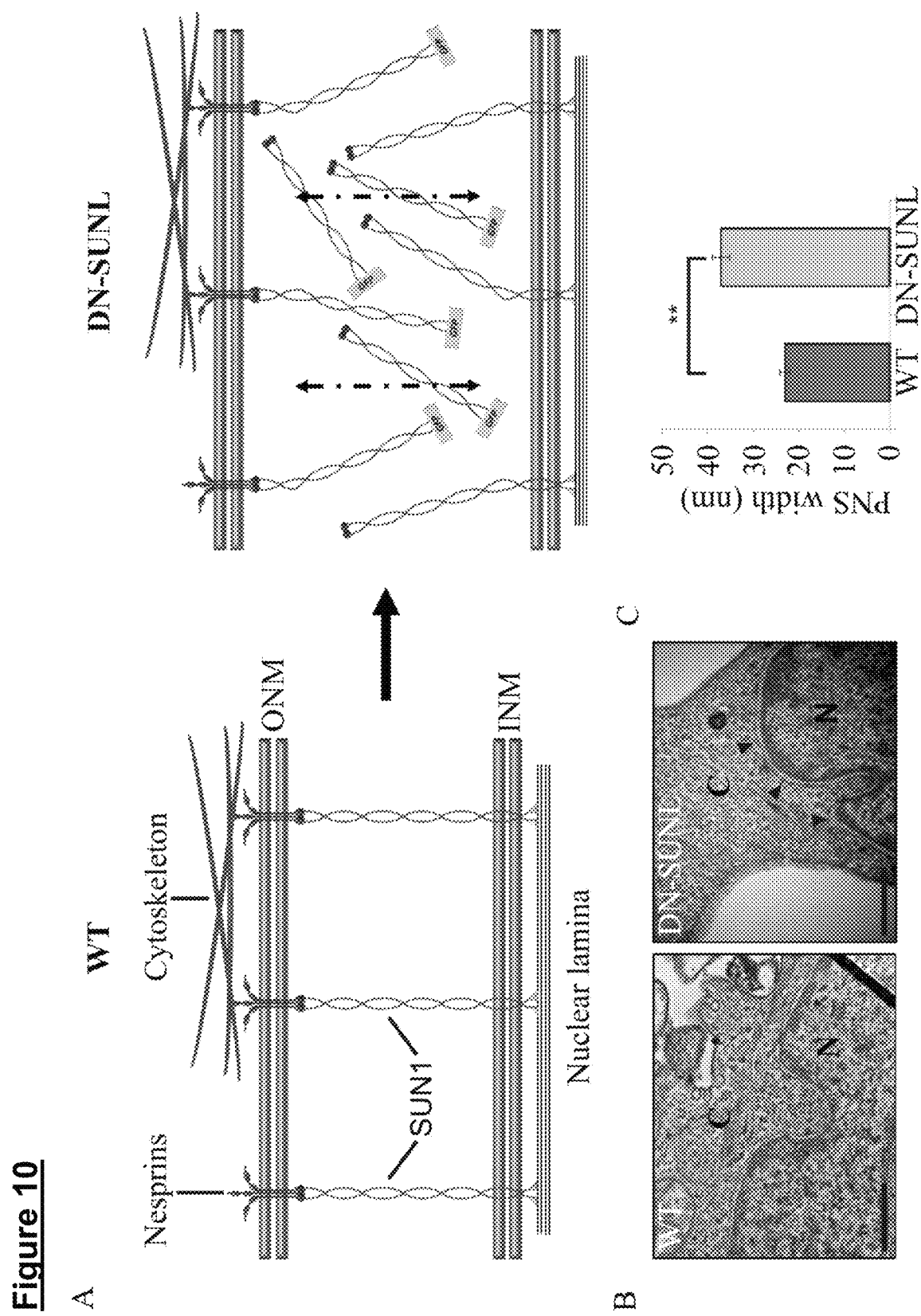
Figure 11:
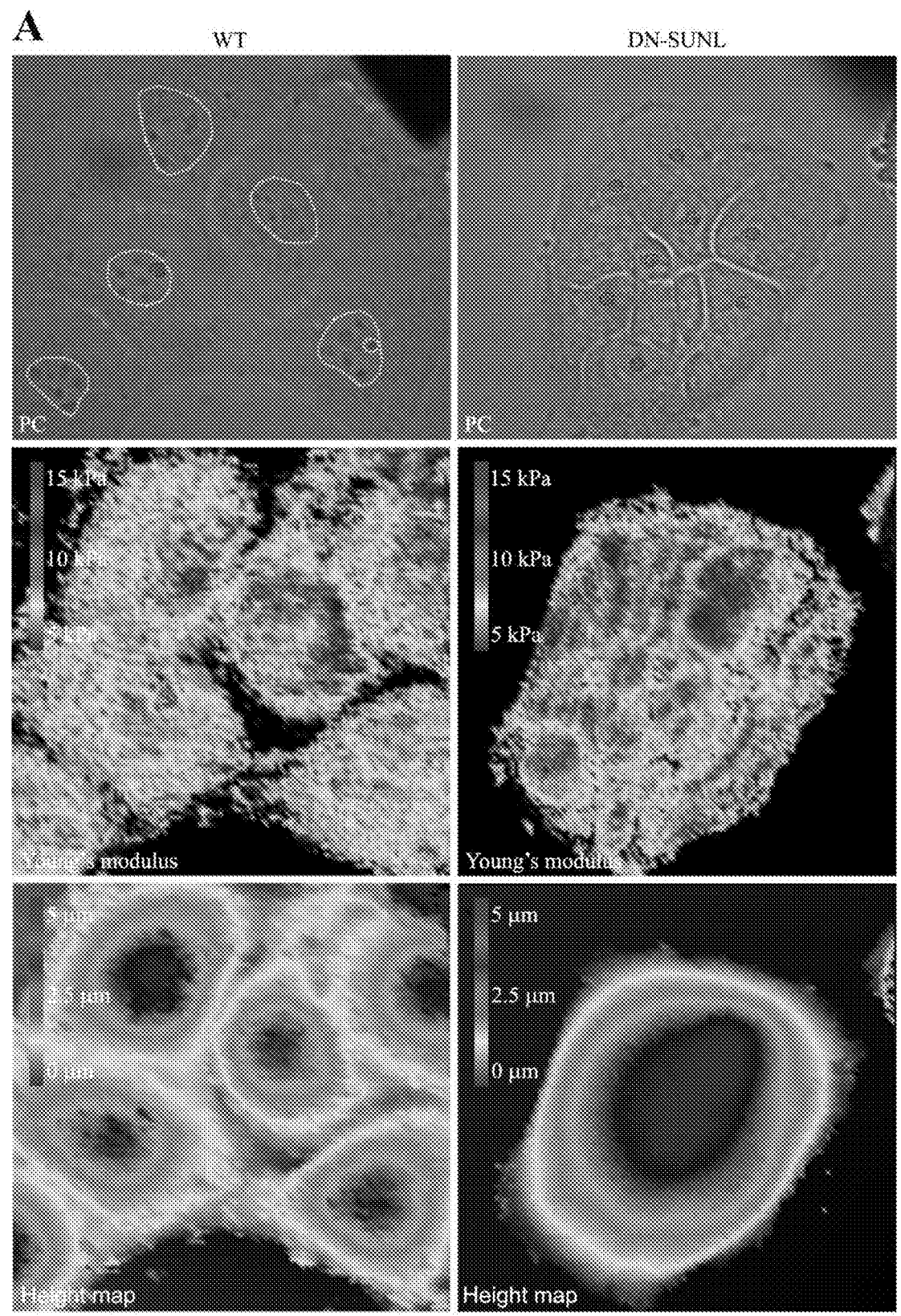
Figure 11:
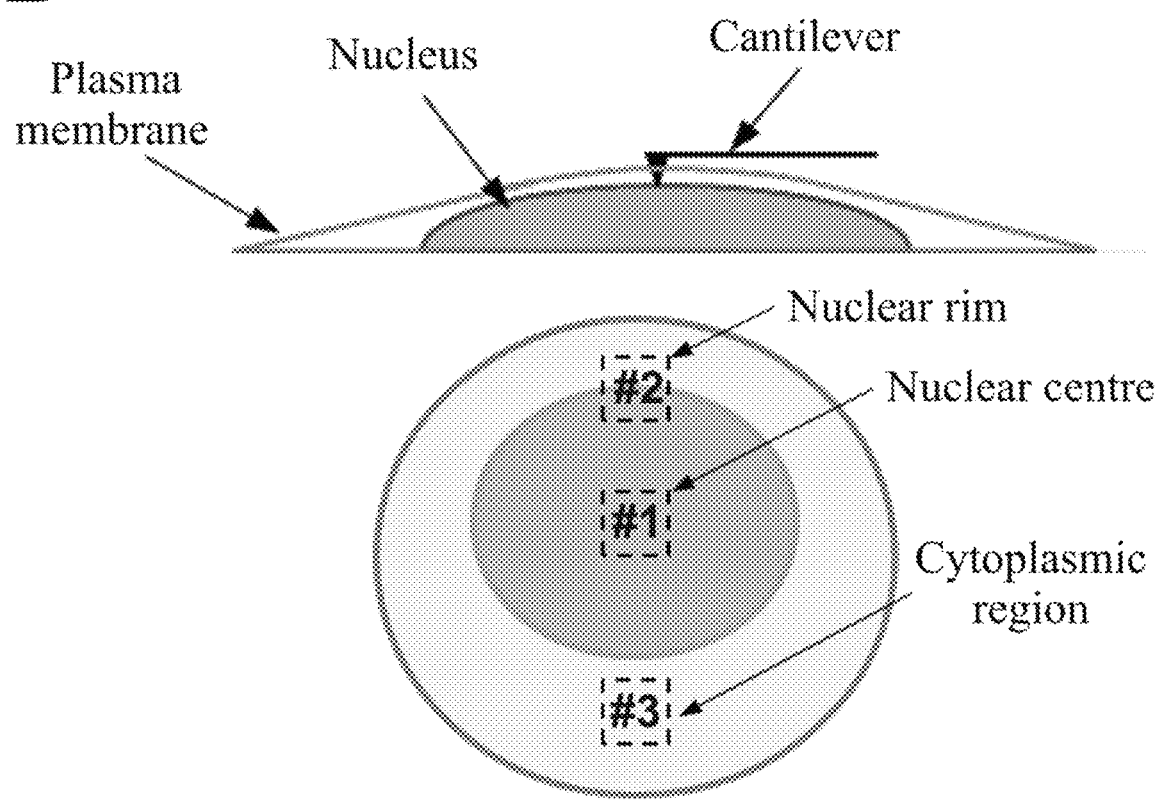
Figure 11:
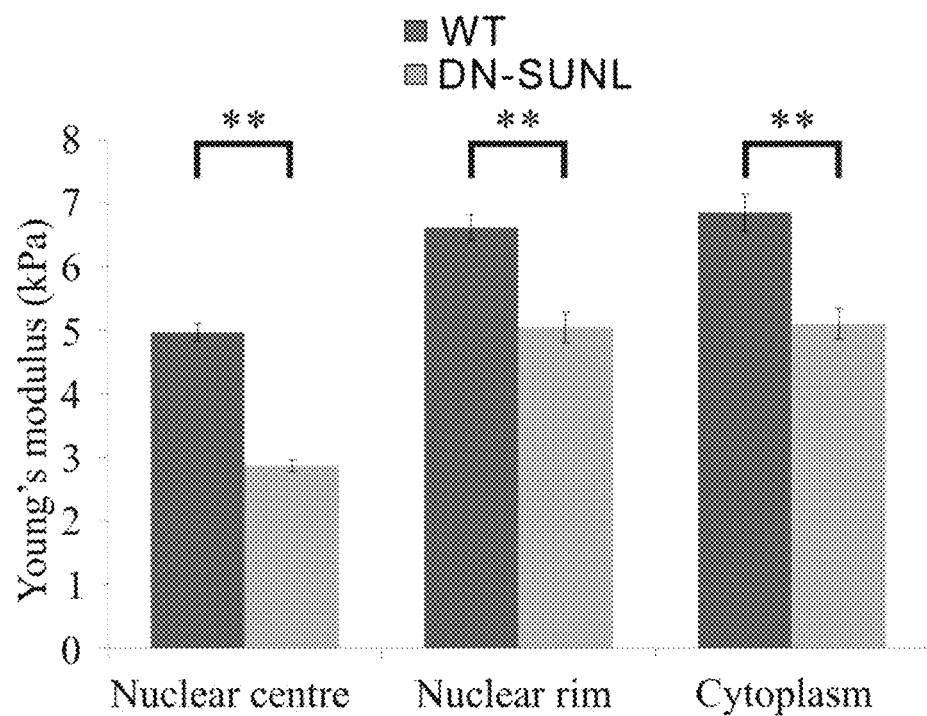
Figure 11:
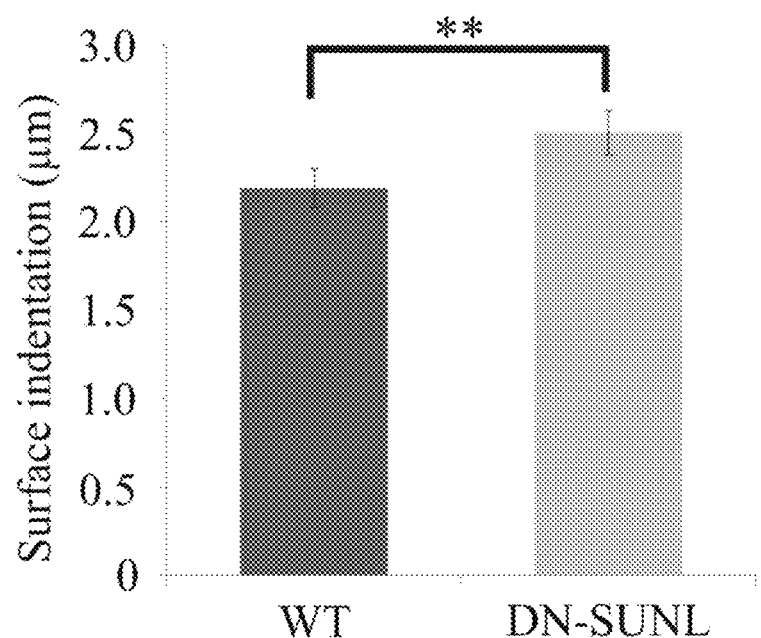
Figure 12:
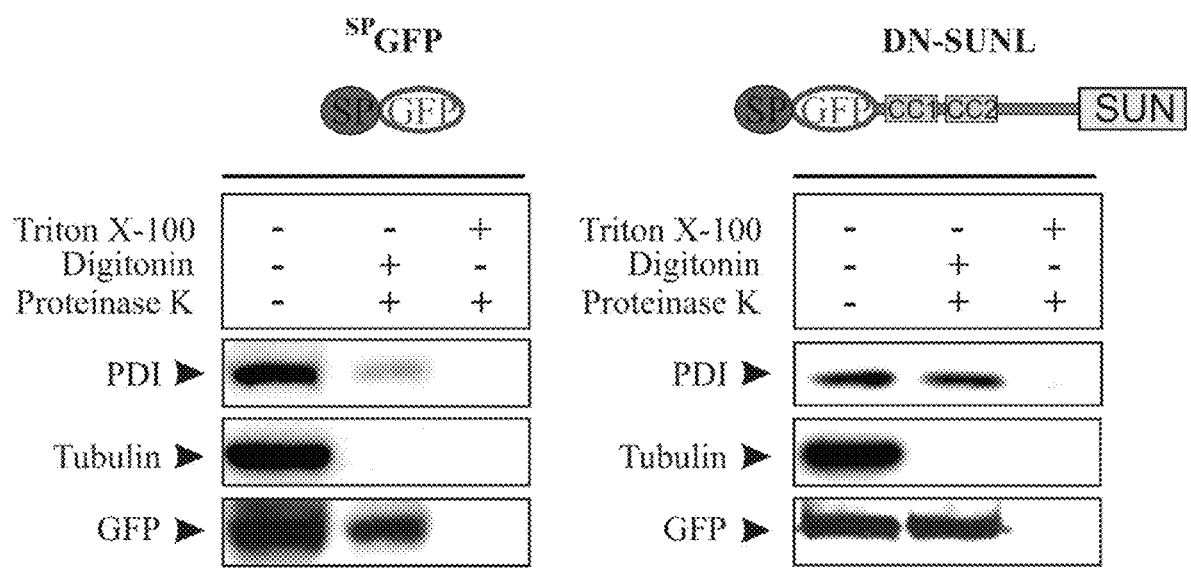
Figure 13:
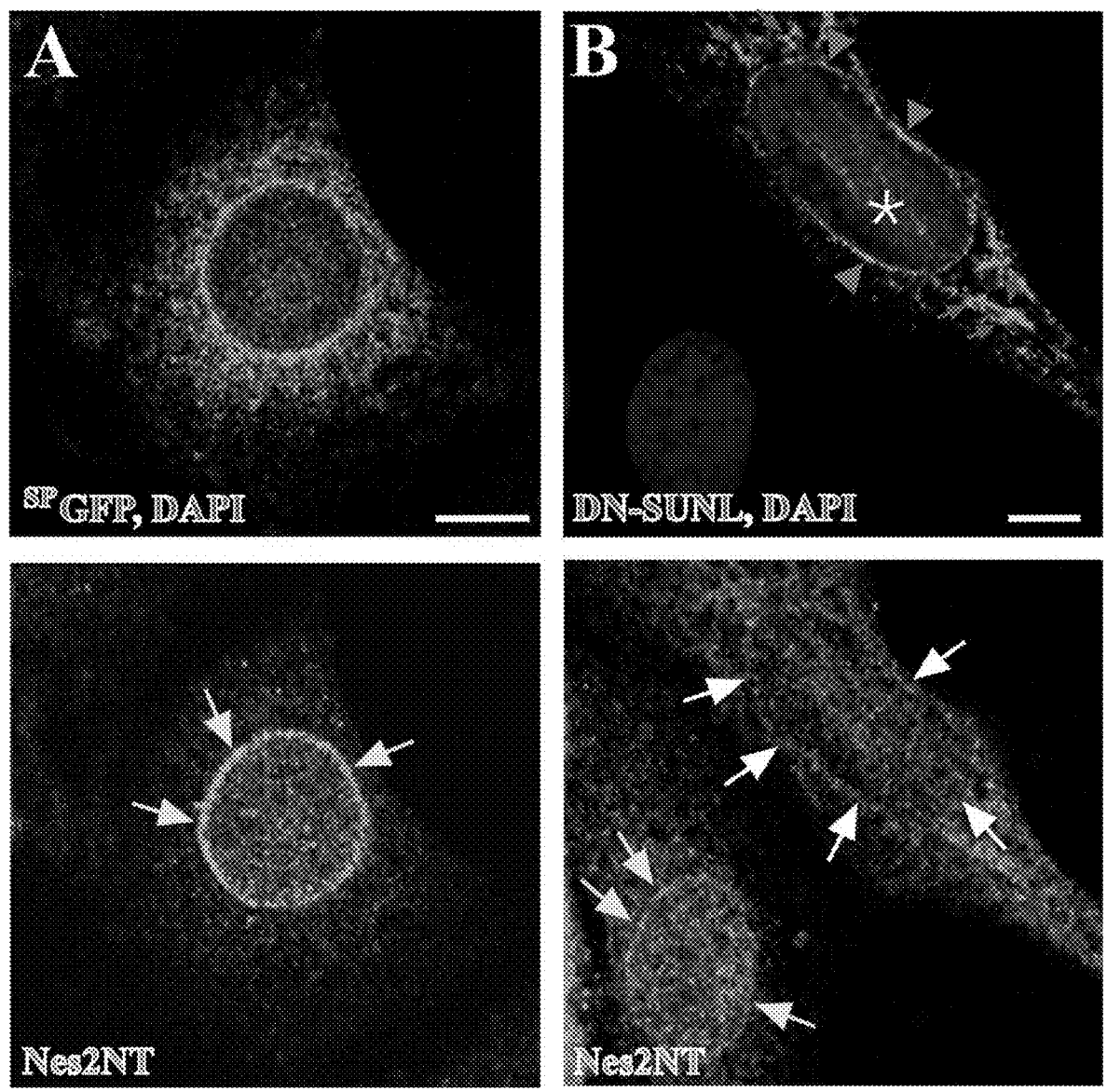

demonstrates significant changes in nuclear morphology in DN-SUNL cells. Results are mean±standard deviation;

FIG. 5 is an indirect immunofluorescence analysis of DN-DUNL (transient transfection) expressing HaCaT (A, C) and human dermal fibroblast cells (B). (A) Schematic representing the basic nesprin-2 giant domain architecture and the epitopes of three specific nesprin-2 antibodies (i.e. Nes2NT, Nes2K49 and Nes2CT). Lower panels depict an immunofluorescence analysis using nesprin-2 antibodies, which shows that DN-SUNL expression displaces all nesprin-2 isoforms from the nuclear envelope (arrows). These results highlight the dominant negative effects of the DN-SUNL construct on Nesprin-2. In contrast, control cells (asterisks) exhibit strong nesprin-2 nuclear staining. (B) DN-SUNL expression in fibroblasts shows that also endogenous nesprin-1 is efficiently displaced from the nucleus, while untransfected cells (asterisks) display pronounced nesprin-1 nuclear rim staining. (C) The expression of DN-SUNL affects specifically proteins of the KASH-domain family (i.e. nesprins) considering that the subcellular localisation of other key components of the nuclear envelope such as SUN1, emerin, LAP2β, and lamin A/C are largely unaffected. All scale bars=10 m. Nuclei are visualised by DAPI staining (blue);

FIG. 6 is a microscopic image analysis of WT (control) and stably transfected DN-SUNL HaCaT cells, which shows that LINC complex disruption affects drastically cell morphology, cell crowding and cell-cell contact protein expression on 2D surfaces. (A) Phase contrast and fluorescent staining's of nuclei (DAPI, blue) and the F-actin cytoskeleton (Phalloidin, red) of 70% confluent WT and DN HaCaT. Phalloidin denotes the cortical actin cytoskeleton in keratinocytes and therefore visualizes the cell boundaries. Scale bar=200 μm (phase contrast), and 20 μm (fluorescent panels). In contrast to DN cells, WT cells are flatter and less dense within the colonies; (B) DN HaCaT colonies contain twice as much cells compared to WT counterparts. Statistical analysis (Student's t- test; P value <0.05 is indicated by *) demonstrates a significant changes in the cell density of WT and DN-SUNL mutant colonies. Results are mean±standard deviation. (C) DN cells express higher E-cadherin levels compared to WT cells grown on 2D surfaces;

FIG. 7 is an analysis, which shows LINC complex disruption affects cell-to-substrate adhesion on 2D substrates. A) WT and DN HaCaT cells 24 h post trypsinisation were examined using immunofluorescence. Cells are stained for DAPI (blue), phalloidin (cyan) and vinculin (red). Vinculin is a mechano-sensing protein that is enriched at peripheral cell-substratum contacts (termed focal contacts). Arrows display sites of focal adhesion formation across the cell periphery. Note that in contrast to DN cells, WT cells exhibit prominent enrichment of focal contacts at the cell periphery. Vinculin is diffusely distributed in DN cells. Scale bar=10 μm. (B) Western blotting indicating that vinculin levels are not perturbed in DN cells. The localization of vinculin changes upon LINC complex disruption but not the levels of the protein. B-actin and tubulin indicates equal protein loading. Anti-GFP immunoblotting demonstrates expression of dominant negative LINC complex interfering proteins in DN cells;

FIG. 8 is an analysis, which shows that DN-SUNL HaCaT cells (DN) display enhanced stratification properties when grown in 3D scaffolds for 8 days at the air-to-liquid interface. (A) Single and co-cultured (with dermal fibroblasts) DN HaCaT cells grown in 3D form prominent multi-layered structures when grown at the air-liquid interface that favours differentiation of keratinocytes. The black lines indicate the scaffold surface. H&E stained sections are shown. (B) Fluorescence examination of single-cultured DN cells verifies that cell stacking (arrows) is indeed occurring above rather than within the scaffold. The scaffold boundaries are visualized using Nile Red, while the existence of DN cells is denoted using GFP. Scale bars=25 m. (C) Highlights that LINC disruption substantially favours the formation of epidermal-like (multi-layered cell assembly) tissue structures in vitro. Asterisks denote statistical significance (P value <0.05) using a Student's t- test;

FIG. 9 is an analysis, which shows that DN HaCaT cells display proper epidermal tissue architecture in vitro. (A) Fluorescence microscopic examination of single cultured WT and DN cells in 3D highlighting that DN HaCaT cells (GFP expressing) display shape changes similar to that found in skin. Note that WT cells grown on the surface of the scaffold (visualized with Nile Red) exhibit flattened nuclei (yellow arrows) whereas DN cells proximal to the scaffold surface (denoted by the white dotted line) display columnar shapes (asterisks). In skin, epithelial cell/nuclear flattening occurs only in differentiated cells. Therefore, DN cells at the scaffold/air interface mimic basal keratinocyte morphologies. In contrast, DN cells away from the scaffold surface exhibit pronounced cell flattening (white arrows) a feature common to terminally differentiated skin keratinocytes belonging to the spinous and granular layers of skin. (B) Immunofluorescence analysis of WT and DN cells co-cultured with human dermal fibroblast cells in 3D scaffolds for 8 days at the air-to-liquid interface. Two markers were examined; K14 (Keratin 14) is a marker for basal dividing keratinocytes, while K10 (Keratin 10) is a terminal differentiation marker, which is expressed by suprabasal keratinocytes in skin. Note that DN HaCaT's exhibit increased Kin expression, proper spatial arrangements and morphologies (namely flattening) at areas that are distal to the scaffold surface, which mimics the in vivo situation. Cells in proximity to the scaffold (dotted line) lack K10 staining. In contrast, WT cells exhibit sporadic K10 staining within the scaffold. Scale bars=25 μm;

FIG. 10 (A) is a schematic diagram showing that DN-SUNL expression saturates KASH-domain binding sites at the outer nuclear membrane (ONM) and prevents binding to full-length SUN-domain proteins. DN-SUNL expression consequently disrupts the linkage of the ONM to the inner nuclear membrane (INM) and dilates the perinuclear lumen (discontinuous double arrowed lines). (B) shows TEM micrographs of the nuclear membrane in WT (control) and DN-SUNL HaCaT cells. Arrowheads denote dilation of the nuclear envelope in DN-SUNL cells. C=cytoplasm, N=nucleus. Scale bar 500 nm. C) Histogram shows the width of the perinuclear lumen in WT and DN-SUNL expressing cells. Statistical analysis (Student's t test; P value <0.005 is indicated by **) demonstrates a significant dilation of the nuclear envelope in DN-SUNL mutants. Results are mean±standard deviation;

FIG. 11 is an analysis of the cytoplasmic and nuclear organelle biomechanical properties of interphase WT and DN-SUNL HaCaT cells examined under biological conditions, showing that LINC complex disruption (DN-SUNL cells) yields significantly softer cells. (A) Phase contrast images of WT and DN-SUNL cells (top row). The position of the nuclei (white dotted lines) and nucleoli (purple dotted circles) is indicated. The corresponding atomic force microscopy (AFM) Young's modulus (kPa) analysis of the WT and DN-SUNL mutant colonies (middle row) and AFM height scans (m; lower row) is shown. (B) Schematic diagram indicating three distinct cellular areas where AFM Young's modulus measurements were taken. (C) Histogram showing that across the three selected cellular areas that DN-SUNL are significantly softer compared to their WT counterparts (n=15 for each cell type). (D) Histogram depicting the highest cantilever surface indentation (m) measured on WT and DN-SUNL cells using a cantilever force of 150 pN, indicates that DN cells are significantly more pliable compared to WT (n=35 for each cell type). Statistical analysis (Student's t test; P value <0.005 is indicated by **);

FIG. 12 is a Western blot analysis of HaCaT cells that have been transiently transfected with either $^{SP}$GFP or DN-SUNL encoding plasmids. Three different experimental conditions were examined. Prior to Western blotting the cell homogenates were either left untreated (positive control) or treated with two different detergents: digitonin or Triton X-100 in the presence of the proteinase K enzyme. Digitonin permeabilises selectively the plasma membrane but leaves the ER and NE membranes intact. In contrast, Triton X-100 permeabilises all cellular membranes including the ER and the NE. Note that the GFP fusions and ER-lumen resident PDI (protein disulphate isomerase; control) proteins are detectable in the digitonin-treated samples but are completely absent in the Triton X-100-treated samples. Tubulin acts as a control for the cytoplasmic compartment, which is digested irrespectively of the detergents used; and FIG. 13 is an indirect immunofluorescence analysis of SP-GFP (A) or DN-DUNL (B) transiently transfected NIH-3T3 fibroblasts using anti-Nesprin-2 giant (Nes2NT) antibodies, which shows the dominant negative effects of the DN-SUNL construct on the KASH-domain containing Nesprin-2 giant isoform. Note that the DN-SUNL expressing cell (asterisk) displays a GFP signal at the ER (red arrows) and the NE (blue arrows), but lacks nuclear nesprin-2 staining (white arrows). In contrast SP-GFP expressing control cells or DN-SUNL untransfected cells exhibit strong nesprin-2 staining at the nucleus (yellow arrows). Nuclei are visualised by DAPI staining (blue). Scale bars=10 m.

EXAMPLES

Cells of specific tissues have correspondingly specific properties, including biomechanical, biochemical and structural properties. Such specific properties are determined by signals received from the physical and biochemical environment surrounding the cell. The inventors have found that crucial intracellular signalling events occurs via a central "switch" (the LINC complex) that physically links, via the cytoskeleton, genetic material of a cell to the extracellular environment. As shown in the following examples, the inventors have interrupted the formation of the LINC complex using a construct that overexpresses a dominant negative SUN1 fusion protein (DN-SUNL). In doing so, the inventors have induced specific cellular properties without having to create a complex and highly specific external environment.

Materials and Methods

Plasmid Construction

All cloned fragments were sequenced in their entirety. pcDNA3.1 (-) (Invitrogen) was used to engineer the DN-SUNL and the specific control (SPGFP) constructs (see Schneider et al., 2011, Cell. Mol. Life Sci. 68:1593-1610). The DN-SUNL comprises torsin-A signal peptide (SP) sequence, sequences encoding GFP (Green Fluorescent Protein), the coiled-coil domain and the SUN-domain of a murine SUN1 protein (the SUN1 transgene protein lacks the N-terminal domain and the transmembrane domain). The full polypeptide sequence (819 amino acids) of one embodiment of the DN-SUNL is provided herein as SEQ ID No. 28 (previously referred to as SEQ ID No. 40 in patent application GB1701438.2), as follows:

[SEQ ID No. 28]
MKLGRAVLGLLLLAPSVVQAVASVSKGEELFTGVVPILVELDGDVNGHKF

SVSGEGEGDATYGKLTLKFICTTGKLPVPWPTLVTTLTYGVQCFSRYPDH

MKQHDFFKSAMPEGYVQERTIFFKDDGNYKTRAEVKFEGDTLVNRIELKG

IDFKEDGNILGHKLEYNYNSHNVYIMADKQKNGIKVNFKIRHNIEDGSVQ

LADHYQQNTPIGDGPVLLPDNHYLSTQSALSKDPNEKRDHMVLLEFVTAA

GITLGMDELYKEFVSLWGQGNFFSLLPVLNWTAMQPTQRVDDSKGMHRPG

PLPPSPPPKVDHKASQWPQESDMGQKVASLSAQCHNHDERLAELTVLLQK

LQIRVDQVDDGREGLSLWVKNVVGQHLQEMGTIEPPDAKTDFMTFHHDHE

VRLSNLEDVLRKLTEKSEAIQKELEETKLKAGSRDEEQPLLDRVQHLELE

LNLLKSQLSDWQHLKTSCEQAGARIQETVQLMFSEDQQGGSLEWLLEKLS

SRFVSKDELQVLLHDLELKLLQNITHHITVTGQAPTSEAIVSAVNQAGIS

GITEAQAHIIVNNALKLYSQDKTGMVDFALESGGGSILSTRCSETYETKT

ALLSLFGVPLWYFSQSPRVVIQPDIYPGNCWAFKGSQGYLVVRLSMKIYP

TTFTMEHIPKTLSPTGNISSAPKDFAVYGLETEYQEEGQPLGRFTYDQEG

DSLQMFHTLERPDQAFQIVELRVLSNWGHPEYTCLYRFRVHGEPIQ

Thus, in one embodiment, the agent according to any aspect of the invention may comprise an amino acid sequence substantially as set out in SEQ ID No. 28, or a variant or fragment thereof.

The signal peptide has been included to ensure that the DN-SUNL peptide is transported to the endoplasmic reticulum and/or the nuclear envelope. The polypeptide sequence of the torsin-A signal peptide (SP) sequence used in the DN-SUNL is provided herein as SEQ ID No. 29 (previously referred to as SEQ ID No. 41 in patent application GB1701438.2), as follows:

[SEQ ID No. 29]
MKLGRAVLGLLLLAPSVVQAV

The GFP protein has been included to ensure that the DN-SUNL peptide can be visualised under UV light. The polypeptide sequence of the GFP protein used in the DN-SUNL is provided herein as SEQ ID No. 30 (previously referred to as SEQ ID No. 42 in patent application GB1701438.2), as follows:

[SEQ ID No. 30]
SKGEELFTGVVPILVELDGDVNGHKFSVSGEGEGDATYGKLTLKFICTTG

KLPVPWPTLVTTLTYGVQCFSRYPDHMKQHDFFKSAMPEGYVQERTIFFK

DDGNYKTRAEVKFEGDTLVNRIELKGIDFKEDGNILGHKLEYNYNSHNVY

IMADKQKNGIKVNFKIRHNIEDGSVQLADHYQQNTPIGDGPVLLPDNHYL

STQSALSKDPNEKRDHMVLLEFVTAAGITLGMDELYK

The polypeptide sequence of the murine C-terminal SUN1 luminal protein used in the DN-SUNL is provided herein as SEQ ID No. 31 (previously referred to as SEQ ID No. 43 in patent application GB1701438.2), as follows:

[SEQ ID No. 31]
VSLWGQGNFFSLLPVLNWTAMQPTQRVDDSKGMHRPGPLPPSPPPKVDHK

ASQWPQESDMGQKVASLSAQCHNHDERLAELTVLLQKLQIRVDQVDDGRE

GLSLWVKNVVGQHLQEMGTIEPPDAKTDFMTFHHDHEVRLSNLEDVLRKL

TEKSEAIQKELEETKLKAGSRDEEQPLLDRVQHLELELNLLKSQLSDWQH

LKTSCEQAGARIQETVQLMFSEDQQGGSLEWLLEKLSSRFVSKDELQVLL

HDLELKLLQNITHHITVTGQAPTSEAIVSAVNQAGISGITEAQAHIIVNN

ALKLYSQDKTGMVDFALESGGGSILSTRCSETYETKTALLSLFGVPLWYF

SQSPRVVIQPDIYPGNCWAFKGSQGYLVVRLSMKIYPTTFTMEHIPKTLS

PTGNISSAPKDFAVYGLETEYQEEGQPLGRFTYDQEGDSLQMFHTLERPD

QAFQIVELRVLSNWGHPEYTCLYRFRVHGEPIQ 2D and 3D Cell culture

WT and DN-SUNL HaCaT, NIH-3T3 and primary human dermal fibroblast (HDF; LifeTechnologies) cells were cultured at 37° C., 5% $CO_2$ in Dulbecco's Modified Eagles Medium, high glucose supplemented with 10% fetal calf serum, 2 mM penicillin, and 2 mM streptomycin (Sigma). For the cultivation of stable transfected DN-SUNL HaCaT cells, 0.5 mg/ml G418 disulphate (Sigma) was added to the media solution. 2D cell culture was performed on conventional poly-styrene flasks, 10 cm petri-dishes and 12/24 well dishes. For 3D culture, 12-well Alvetex® Strata inserts (Reinnervate) were employed. Materials were pre-treated with oxygen plasma for 5 min at 40 W using an Emitech K1050X Plasma Asher.

To seed the cells to Alvetex® Strata, 100 μl of WT or DN-SUNL HaCaT cell suspension containing 250,000 cells each was applied directly to the centre of each pre-treated scaffold. The scaffolds were then placed in their respective culture dishes and moved into a cell culture incubator for 20 min to allow cell attachment to the scaffold surface. Complete culture media was added. For the co-culture observations, 500,000 HDF cells at a T-75 confluence of 60% were placed onto plasma-treated scaffolds alongside complete culture medium and cultured in 12 well plates for 7 days. The scaffolds were transferred into 6 well plates containing 4 mL complete culture media and were cultured for a further 7 days. Either WT or DN HaCaT cells were then seeded. After the seeding of 250,000 keratinocytes (applies for both single or co-culture experiments) the cells were grown submerged in media for 4 days, before the cells were grown at the air-liquid interface for another 8 days.

Paraffin Embedding and Immunofluorescence Microscopy 3D cell cultures were rinsed once with cell culture grade phosphate-buffered saline (PBS) and carefully unclipped from the insert holder. Upon removal, scaffolds were washed a further two times in PBS for 5 min, submerged within 4% paraformaldehyde (PFA) in PBS, pH 7.4 and left at 4° C. overnight. After fixation, scaffolds were washed another two times in PBS for 5 minutes each. Washing was then followed by 15 min incubations in varying ethanol concentrations of 30%, 50%, 70%, 80%, 90%, 95% and 100% v/v at room temperature. Scaffolds were subsequently removed from their housing inserts, cut in half across their diameter using sterilised surgical scissors and incubated for 15 min in Histoclear (Fisher, 12358637) at 60° C. An equal volume of liquid paraffin wax (Fisher, 12624077) was added, and the scaffolds were incubated for 15 min at 60° C. The Histoclear/liquid paraffin solution was then replaced with fresh paraffin wax, and the scaffolds were incubated for 1 h at 60° C. Vertical embedding was then performed in which the scaffold sections were placed into embedding moulds (Cellpath Ltd, GAD-5302-02A) with the cut side facing down. These were then topped with a labelled embedding cassette (SLS, HIS0029), and filled with fresh paraffin wax.

The resulting wax blocks were sectioned using a Leica RM2125RT microtome with MB Dynasharp microtome blades (Fisher, 12056679). For all cell lines, sections were cut to a thickness of 10 μm for conventional haematoxylin and eosin (H&E) staining, with subsequent 7 μm sections for antibody staining. Sections were then floated on a 42° C. water bath, mounted onto Superfrost+microscope slides (Fisher, 10149870) and left to dry overnight on a 32° C. heated slide dryer. Sections were subsequently deparaffinised in Histoclear and hydrated through a series of 5 min incubations in 100%, 70% ethanol and PBS. Antigen retrieval was performed using microwave heating; samples were heated three times 5 min in citrate buffer, with cooling at RT for 30 see between each heat treatment. Sections were cooled, treated with permeabilisation/blocking solution (20% normal goat serum [Sigma] in 0.4% Triton X-100 PBS) for 45 min before processing for indirect immunostaining. 2D cell cultures were fixed in 4% paraformaldehyde/PBS for 15 min and permeabilized in 0.5% Triton X-100/PBS for 10 min before the samples were processed for indirect immunostaining. Focal adhesion sites were identified through vinculin staining, scaffolds were counterstained with NILE red (Sigma, nuclei were stained with 4,6-diamino-2-phenylindone (DAPI; Sigma) and F-actin with TRITC-Phalloidin (Sigma).

All indirect immunofluorescence samples were analysed by confocal laser-scanning microscopy using a TCS-SP5 (Leica).

Antibodies

Primary antibodies used were directed against the C-terminus of nesprin-1 (specII), the N-terminus of Nesprin-2 (Nes2NT) mAb K56-386 [Luke et al., 2008, J. Cell Sci. 121, 1887-1898] and mAb $K_2O$-478 [Zhen et al., 2001, J. Cell Sci. 115, 3207-3222], the C-terminus of Nesprin-2 (Nes2CT) pAb K1 [Libotte et al., 2005, Mol. Biol. Cell 16, 3411-3424], β-actin mAb AC-74 (Sigma), GFP mAb K3-184-2 [Schneider et al., 2011, Cell. Mol. Life Sci. 68:1593-1610], Suni (Padmakumar et al., 2005, J. Cell Sci. 118, 3419-3430), lamin A/C (Jol2), tubulin mAb WA3 (kind gift from Dr. U. Euteneuer), vinculin mAb V9131 (Sigma), E-Cadherin rtAb U3254(Sigma), keratinio rbAb 76318 (Abcam) and keratin14 mAb 7800 (Abcam). For indirect immunofluorescence studies, Alexa 488, Alexa 568, and Alexa 647 fluorescently conjugated secondary antibodies (Invitrogen) were utilized. Peroxidase-coupled secondary antibodies (Sigma) were adopted in Western blot analysis.

H&E Histochemistry

Paraffin wax was cleared from the superfrost microscopy 3D scaffold-containing slides by washing with Histoclear for 5 min at room temperature. Gradual sample rehydration was conducted through washes in 100% ethanol for 2 min, 95% and 70% ethanol for 1 min, and distilled water for a further 1 min. Nuclei were then stained via a 5 minute incubation in Mayer's haematoxylin (Sigma, H1532) (0.1% v/v haematoxylin, 0.02% v/v sodium iodate, 5% v/v aluminium potassium sulphate, 5% v/v chloral hydrate and 0.1% v/v citric acid in $dH_2O$), followed by a 1 min wash in distilled water and incubation in alkaline alcohol (3% ammonia in 70% ethanol) for 30 sec to stain nuclei. Samples were subsequently dehydrated by 30 sec incubations in 70% and 95% ethanol. Once dehydrated, cytoplasmic staining in 0.5% eosin (Sigma, E4009) in 95% ethanol for 1 min was carried out. The samples then underwent two 10 sec washes in 95% ethanol, followed by two washes in 100% ethanol, the first for 15 sec and second for 30 sec. Slides were then cleared via 2×3 min washes in Histoclear, prior to mounting with DPX mounting media (Fisher, 10050080) and covering with a 50×22 mm coverslip (Fisher, 12383138). Slides were left to dry at 4° C. overnight and then imaged using a Leica DM500 light microscope with attached ICC50 HD camera at lox and 20× magnifications utilising the LAS EZ software (Leica).

Western Blotting

Protein lysate preparation from 2D cultured dishes is covered in detail in Carthew and Karakesisoglou (2016; Methods Mol Biol. 2016; 1411: 221-32). To extract protein lysates from 3D cultured cells, scaffolds were washed three times in PBS, removed from their housing inserts and cut into small (~1 mm), square pieces with sterilised scissors. Scaffold sections were then incubated in 500 μl RIPA [50 mM Tris/HCl (pH 7.5), 150 mM NaCl, 1% Nonidet-P40, 0.5% sodium desoxycholate] buffer supplemented with 1% protease inhibitor cocktail (Sigma) for 15 min at 4° C., during which sonication every 3 min for 30 see was performed using an MSE soniprep 150 sonicator. The scaffold/cell suspension was centrifuged at 4° C. for 15 min at 12 000 × g to pellet the remaining cell/scaffold debris, with resulting supernatant extracted, combined with 120 μl of 5× concentrated Laemmli sample buffer and boiled at 99° C. for 4 min. Samples were then stored at −20° C. until use.

Selective Permeabilisation and Proteinase Digestions to Elucidate the SP-GFP and DN-SUNL Subcellular Distribution Transiently transfected HaCaT cells that were transiently transfected with the SP-GFP and DN-SUNL transgenes were washed twice with ice-cold PBS buffer once the cell culture plates reached 60-70% confluency. Cells were collected from the plates using a cell scraper, transferred to a centrifuge tube and subjected to a 5 min centrifugation at 1,000 g. The supernatants were carefully removed and the cell pellets were re-suspended in either ice-cold hypotonic buffer [10 mM HEPES (pH 7.5), 1.5 mM KCl, 1.5 mM MgCl2, and 0.5 mM dithiothreitol] or protease inhibitor-containing (Roche) RIPA lysis buffer [50 mM Tris/HCl (pH 7.5), 150 mM NaCl, 1% Nonidet-P40, 0.5% sodium desoxycholate]. The former cell homogenate's were supplemented with either 5 μg/ml digitonin or 1% Triton X-100, incubated on ice for 4 min before the addition of proteinase K (5 μg/ml). After a 30 min incubation on ice the proteinase K-mediated digestion was terminated using 10 μg/ml phenylsulfonyl fluoride (PMSF). The digested samples were subjected to a 20 min centrifugation at 12,000 g and the supernatants were supplemented with Laemmli sample buffer. The RIPA-containing cell homogenates were incubated on ice for 15 min, centrifuged at 12,000 g, and the supernatants were mixed with sample buffer. All cell extracts were passed at least 20 times through a 27-gauge needle, before the lysates were analysed by SDS-PAGE, and Western blotting.

Transmission Electron Microscopy 2D cultured cells were fixed though 30 min incubations in 2% glutaraldehyde diluted in NaHCa buffer, washed two times in NaHCa buffer and incubated for 15 min in a solution of 1% tannic acid and 0.075% saponin at RT. Cells were then rinsed two times in NaHCa buffer, followed by two further washes in 0.1 M cacodylate buffer and transferred to a 1.5 ml centrifuge tube. Cell suspensions were centrifuged at 1000 g for 4 min, with resulting pellet incubated for 1 h in a solution of 0.5% osmium tetroxide in 0.1 M cacodylate buffer. Pellets were further washed twice in 0.1 M cacodylate buffer, dehydrated through three 5 min washes in 50%, 70%, 95% and 100% ethanol solutions, and infiltrated two times with a 1:1 mixture of 100% alcohol and propylene oxide for 10 min. Cells were then incubated in a 1:1 mixture of propylene oxide and epoxy resin (EPON™ 828) at 60° C., twice in 100% epoxy resin at 60° C. for 30 min, and finally in fresh epoxy resin at 60° C. for 24-48 h to allow polymerisation. Ultra-thin sections were cut to 70 nm using a Leica EM UC6, and mounted onto Formvar coated copper grids. Grids were incubated in uranyl acetate for 10 min, rinsed twice in distilled water, and further incubated in lead citrate (0.4% lead citrate w/v, 0.5% sodium citrate in 0.1 N NaOH) for 10 mins. Subsequent image acquisition was performed using a Hitachi TEM-H7600 transmission electron microscope.

Atomic Force Microscopy

Cells were cultured to a confluence of 60% on 35 mm plastic petri dishes (TPP). 30 min before analysis, extensively PBS-washed cultures were placed into sterile filtered, $CO_2$ independent culture media (Fisher). Subsequent examination was conducted using a Nanowizard® 3 Bioscience atomic force microscope (JPK) using a (D)NP silicon nitride probe cantilever, expressing a spring constant of 0.06-0.7 N/m (Bruker, DNP-10) over a 15×15 μm grid. Cells were maintained at a constant temperature of 37° C. throughout image collection. Young's modulus values were generated using the Gwyddion image analysis software.

Statistical Analysis

Statistical analysis was performed using Student's t test; 300 cells were used for every data set unless otherwise stated. Results were shown as mean±SD. P values of <0.05 were considered significant. The mean±SEM cell stacking from the 3D cell culture experiments and all the 2D morphometrics data sets were measured using the processing software ImageJ (v1.49).

Example 1—Components of the LINC Complex

Figure 1:
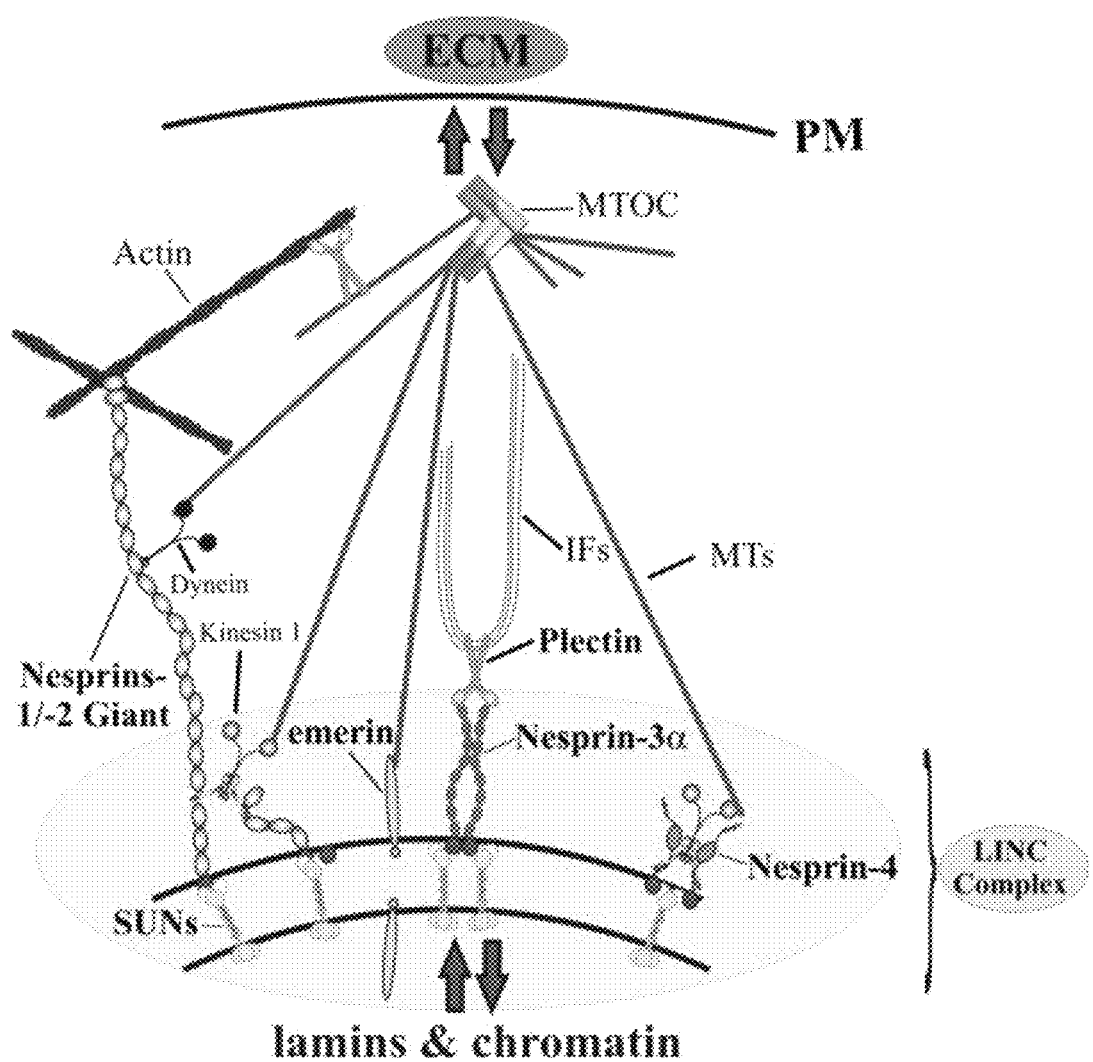
FIG. 1 is a schematic diagram, which shows that LINC complex is a conserved structure formed by Nesprin (i.e. nesprin-1, nesprin-2, nesprin-3 and nesprin-4) and SUN-domain proteins, which span the entire nuclear envelope and functionally link the nuclear interior (e.g. lamina, chromatin, telomeres, transcription factors) to the extracellular matrix (ECM) via associations to multiple cytoskeletal structures (e.g. microtubules [MTs], intermediate filaments [IFs], actin, dyneins, kinesins, Microtubule organising centre [MTOC]), cytolinker proteins (e.g. plectin) and plasma membrane [PM] receptors. High (termed giant) and low molecular weight Nesprin-1 and -2 isoforms are indicated. SUN-domain proteins are depicted as trimers.
Figure 2:
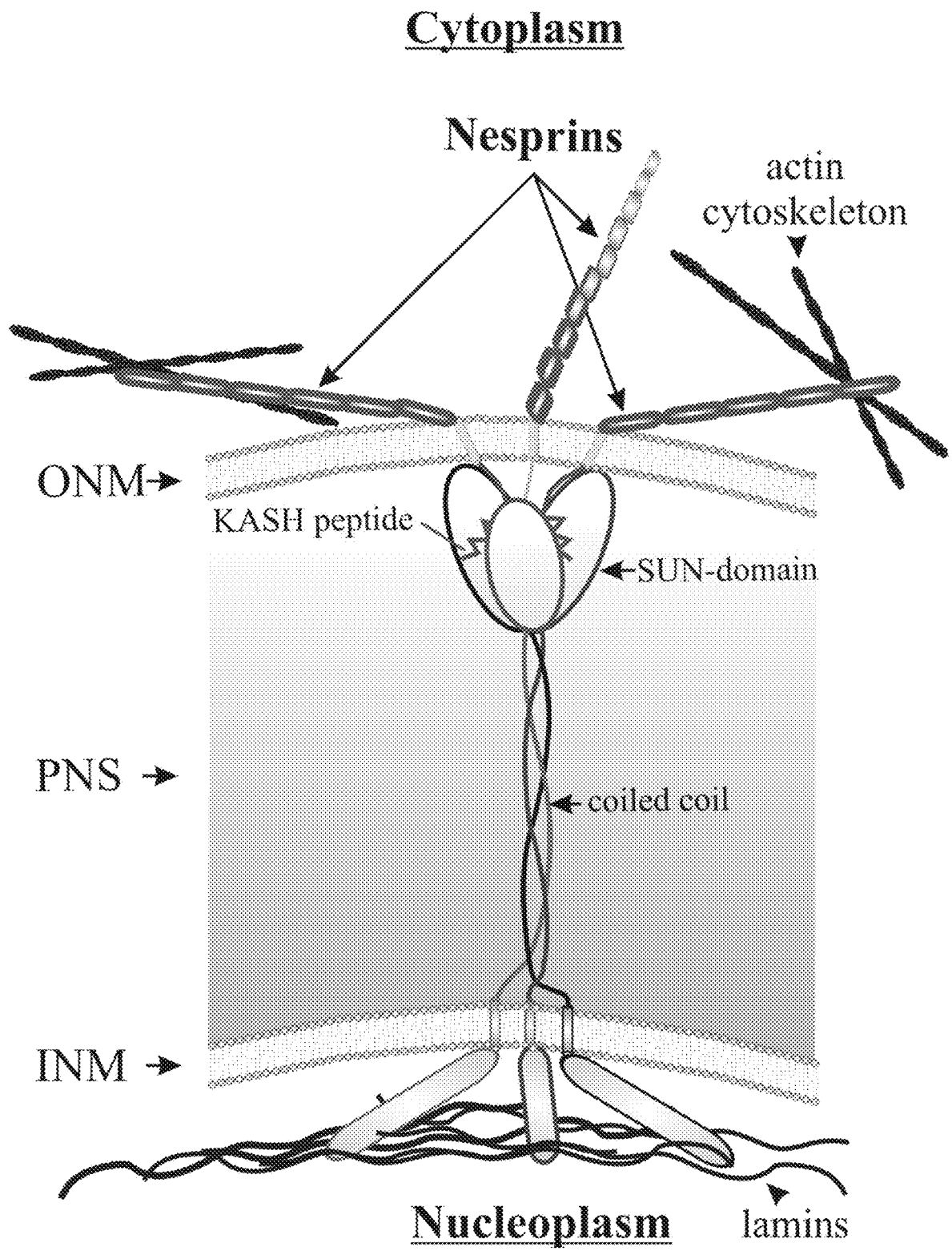
FIG. 2 is a schematic diagram of the LINC complex bridge across the nuclear envelope. The LINC complex bridge comprises SUN and KASH interactions within the perinuclear space alongside associated cytoskeletal and nucleoskeletal networks. ONM: outer nuclear membrane, INM: inner nuclear membrane, PNS: perinuclear space.

The LINC complex is widely recognised as the major nuclear envelope (NE) component able to provide the mechanical links between the nucleus and cytoskeletal network, comprising an outer nuclear membrane (ONM) KASH domain proteins and inner nuclear membrane (INM) SUN proteins (see FIGS. 1 and 2). The KASH domain projects into the NE lumen, where it interacts with SUN domains. This SUN-KASH interaction helps to anchor KASH proteins to the NE, preventing them from diffusing into the adjoining endoplasmic reticulum (ER). The ONM KASH proteins interact with a range of cytoskeletal components, and thus, physically tether the nucleus to the cytoplasmic compartment, whereas the SUN proteins physically interact with INM proteins networks, such as the nuclear lamina and chromatin components. This complex of proteins therefore establishes a physical bridge between the cytoskeletal and nucleoskeletal networks. The formation of this two-membrane adhesive assembly of proteins is capable of transmitting force across the NE, providing function in maintaining centrosome-nuclear interactions, nuclear architecture, signal transduction, DNA repair and chromosome migration. This therefore suggests that the LINC complex must be a dynamic protein network of highly ordered protein interactions, allowing the transmission of multiple signal transductions from a variety of cytoskeletal components to the nuclear interior.

Example 2—SUN₁ Luminal Domain Dominant Negative Construct (DN-SUNL)

Figure 3:
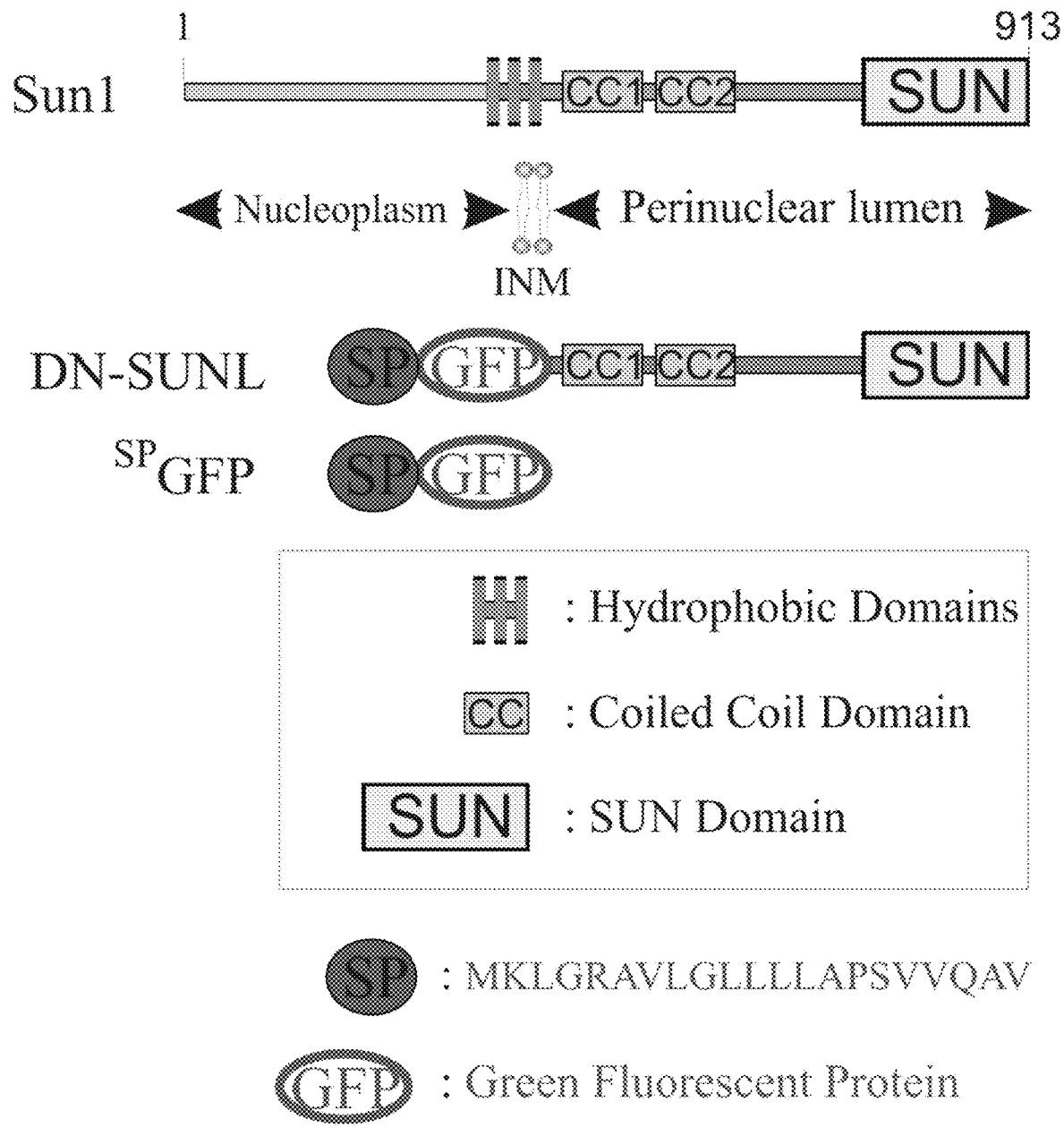
FIG. 3 is a schematic diagram of the DN-SUNL construct, which encodes a dominant negative SUN1 luminal domain in relation to the full-length Suni protein. Major Suni protein domains and topologies within the nuclear envelope are indicated. The truncated SUN1 protein (lacks the N-terminus, which is found in the nucleoplasm, and the three hydrophobic domains) is fused to the Torsin A signal peptide (SEQ ID NO:29) (SP; the amino acid sequence is given), GFP (green fluorescent protein) and expressed in the endoplasmic reticulum (ER) and nuclear envelope lumen (Schneider et al., 2011, Cell. Mol. Life Sci. 68:1593-1610) where it binds and saturates all KASH-protein binding sites (see FIG. 10 for more details). Due to these associations all endogenous full-length KASH-proteins are dislodged from the nuclear envelope (hence dominant negative). SP-GFP is the relevant control (Schneider et al., 2011, Cell. Mol. Life Sci. 68:1593-1610) that lacks the SUN1 N-terminal nucleoplasmic and C-terminal luminal sequences but harbours the signal peptide sequences.
Figure 4:
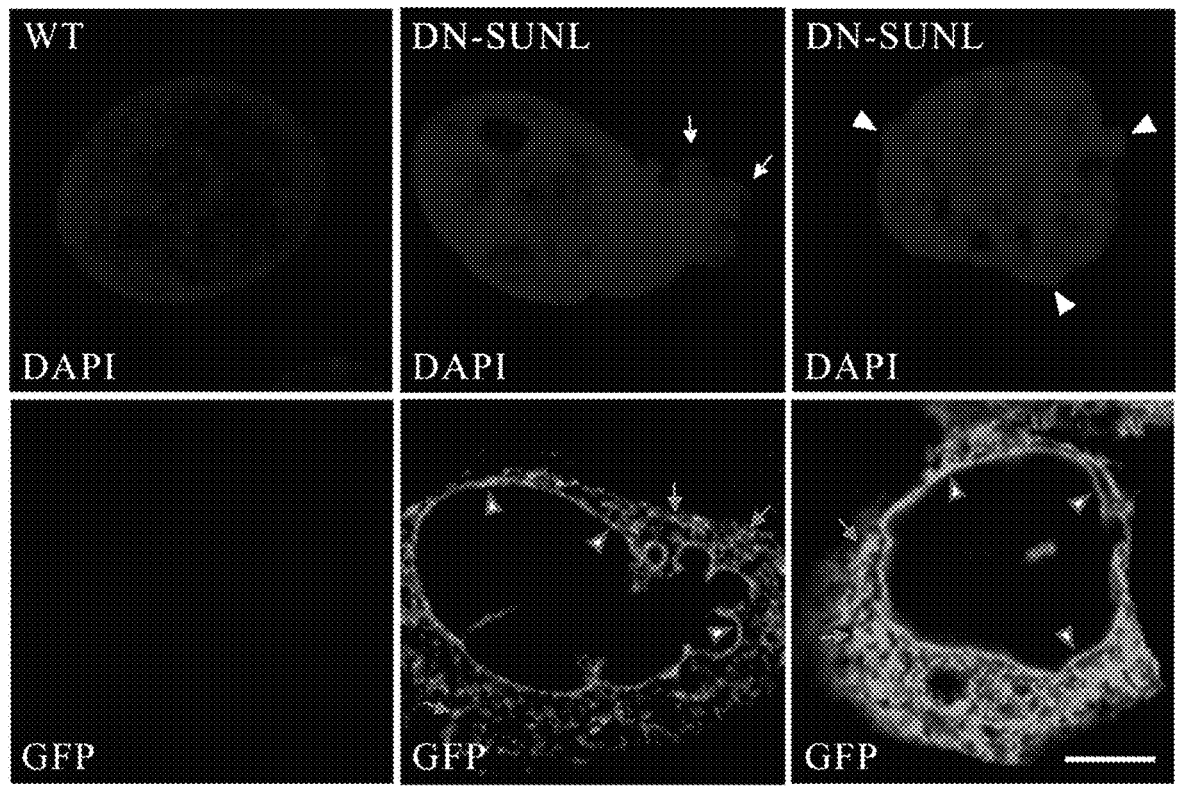
FIG. 4 is an indirect immunofluorescence analysis of wild type (WT) and DN-DUNL transiently transfected HaCaT cells that were counterstained with DAPI (blue) to stain nuclei. In panel (A) the DN-SUNL subcellular distribution (GFP channel) is highlighted. Note the distinct nuclear rim (red arrowheads) and reticular pattern of DN-SUN1 in the cytosol (blue arrows), which corresponds to the endoplasmic reticulum (ER) membranes. DN-SUNL expression affects nuclear shape (white arrows) and yields blebs at the nuclear surface (white arrowheads). Scale bar=10 m. (B) Statistical analysis (Student's t-test; P value <0.05 is indicated by *)
Figure 4:
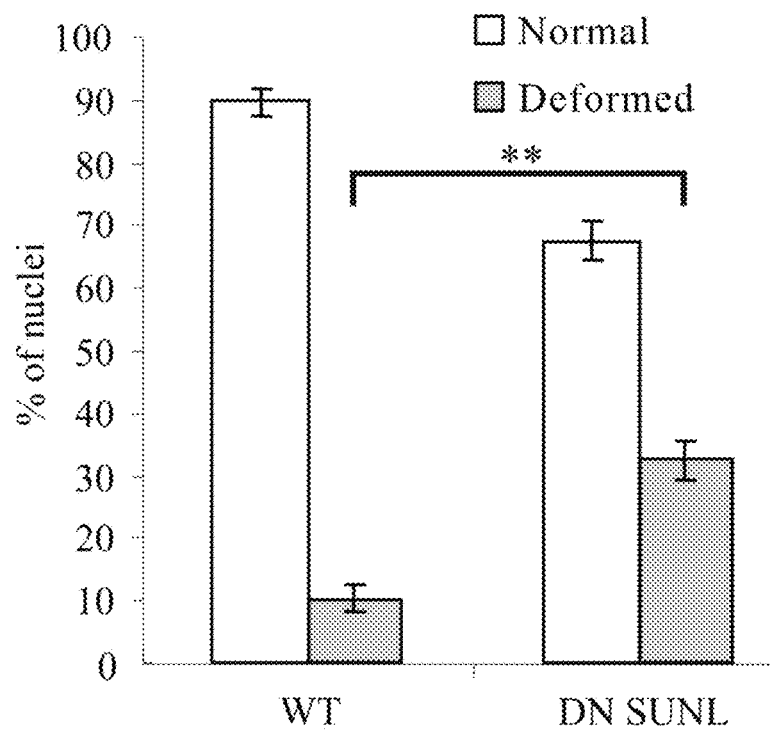

In order to study the role that the LINC complex protein, SUN1, plays in cellular structure and function, the inventors developed a construct (see FIG. 3) that encodes and overexpresses a fusion protein comprising a GFP-tagged luminal domain of SUN1 attached to an ER signal peptide (SP). The signal peptide was incorporated to ensure the fusion protein is overexpressed in the endoplasmic reticulum (ER) and the perinuclear space. To confirm that the fusion protein had translocated into the ER lumen and the perinuclear space, cell homogenates of HaCaT keratinocytes were subjected to proteinase K degradation in the presence of Triton X-100 or digitonin (see FIG. 12). In contrast to Triton X-100, which permeabilizes all biological membranes, low concentrations of digitonin leave the internal ER (endoplasmic reticulum) and NE (nuclear envelope) membranes unperturbed. Digitonin permeabilizes only cholesterol-rich membranes (i.e. plasma membrane). Similar to the ER and perinuclear space resident disulphide isomerase (PDI) protein, the $^{SP}$GFP and DN-SUNL molecules were susceptible to proteinase K degradation only when cell homogenates were permeabilized with Triton X-100 (see FIG. 12). FIGS. 4 and 5 show that the GFP-fusion DN-SUNL protein is expressed in the ER and the nuclear envelope.

Example 3—SUN1 Interacts with Nesprin-1 and Nesprin-2

Figure 7B:
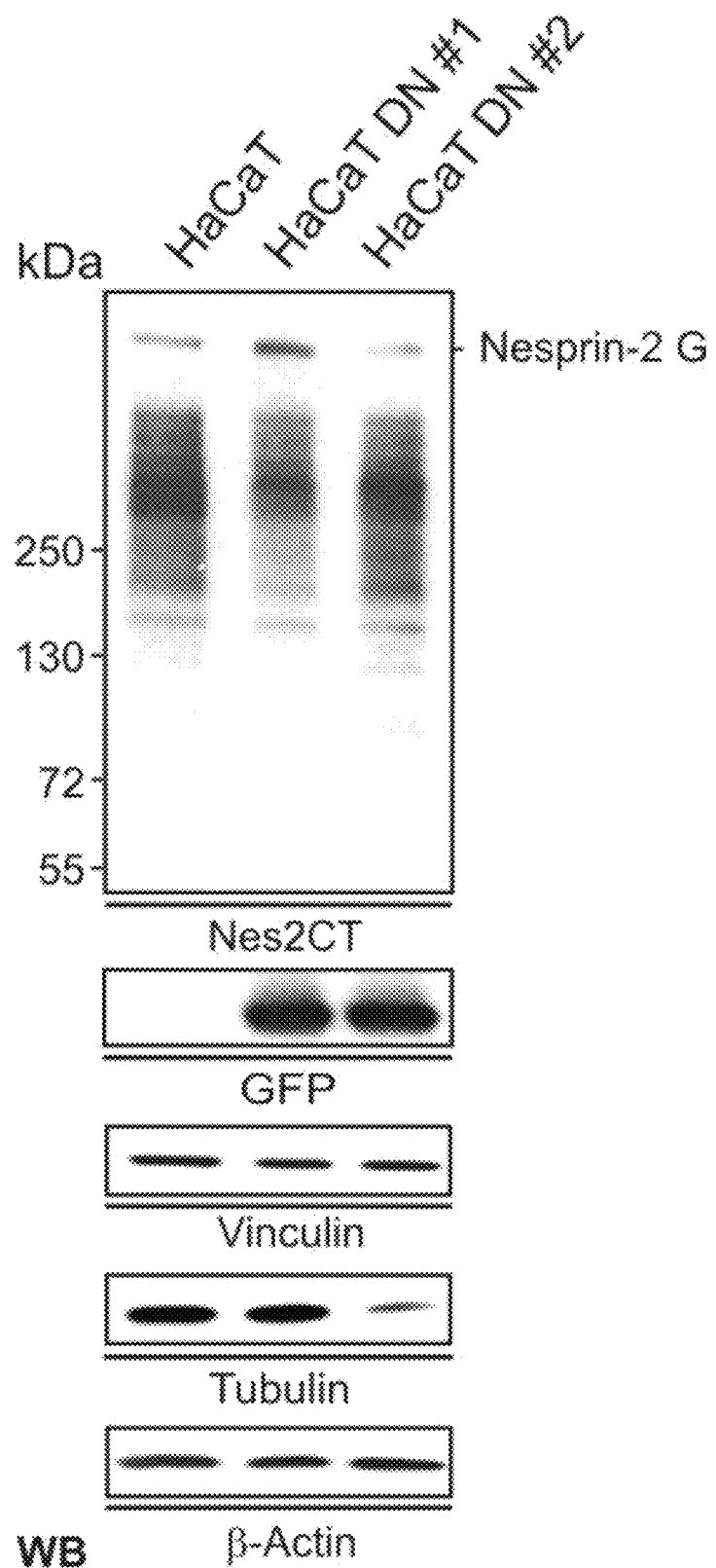

The inventors elucidated the involvement of luminal KASH/SUN protein interactions with Nesprin-1 and Nesprin-2, the cytoplasmic binding partners of SUN1. Transiently transfected control DN-SUNL HaCaT and fibroblasts were immunostained for Nesprins-1 and Nesprin-2, respectively. Their decision to use these particular cellular models was based on the prevalence of Nesprin-1 and Nesprin-2 C-terminal KASH-domain isoforms (i.e. nuclear envelope associated isoforms) in fibroblasts and keratinocytes. In sharp contrast to untransfected cells (see FIGS. 5A and 5B asterisks), the DN-SUNL expression (see green panels in FIGS. 5A and 5B, arrows) dislodged Nesprin-1 and Nesprin-2 from the NE (see red panels in FIGS. 5a and 5b, arrows). Importantly, the localisation of other key nuclear proteins including SUN1 (FIG. 5C) and the Nesprin-2, vinculin, tubulin, and actin expression levels remained unaffected by DN-SUNL expression (FIG. 7B). Furthermore, in contrast to DN-SUNL, SP-GFP (control) does not affect the localisation of endogenous Nesprin-2. This highlights, that the SUN1 C-terminal sequences exert the dominant negative effects on KASH-domain proteins and not the SP and GFP segments of DN-SUNL (FIG. 13), considering that both (SP-GFP and DN-SUNL) are expressed in the same membrane-bound compartments (i.e. ER and NE; FIG. 12).

Figure 6B:
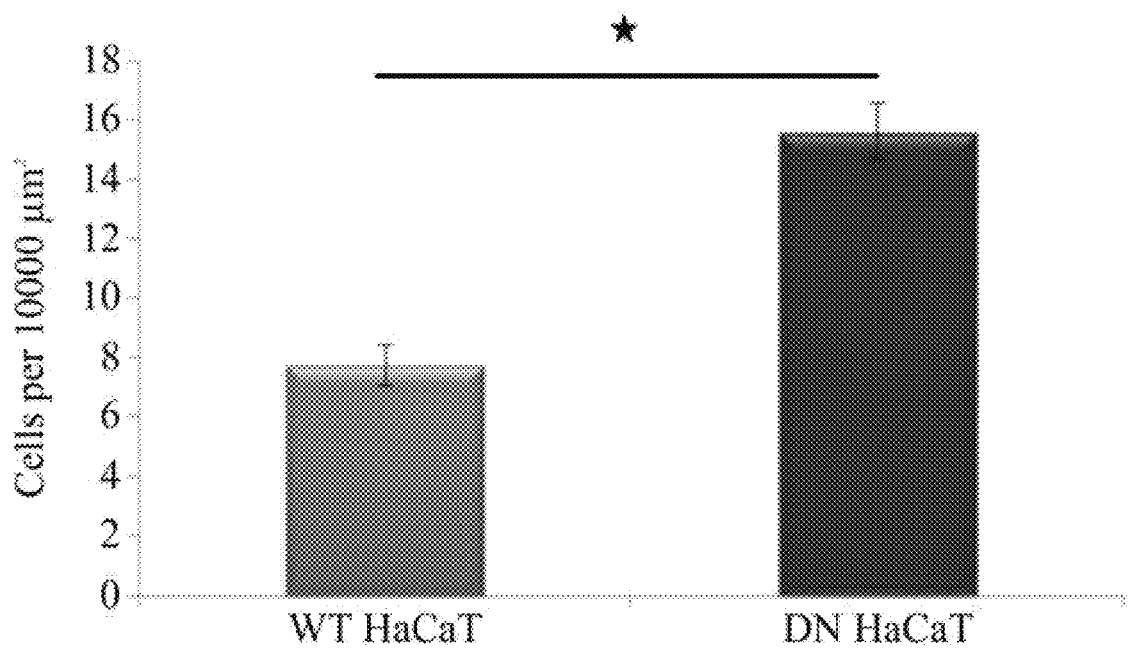
Figure 6C:
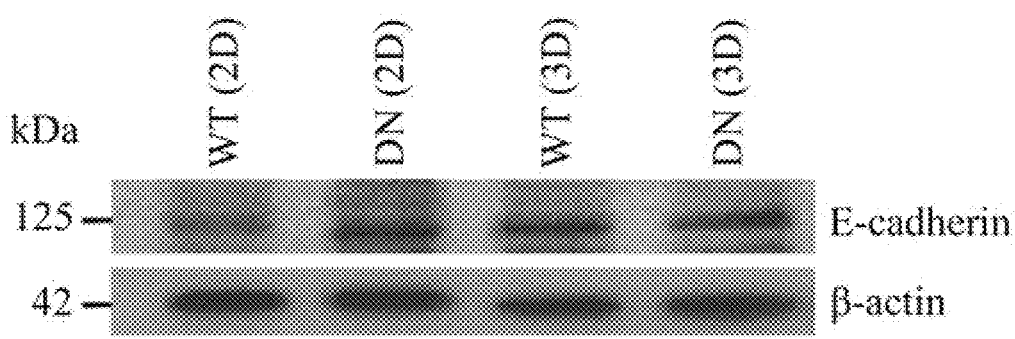

Example 4—LINC Disruption Affects Cell Shape, Cell-Cell Junction Protein Expression and Cellular Density A microscopic comparison (i.e. phase contrast images and fluorescence examination of TRITC-coupled phalloidin [phalloidin binds filamentous actin]) of WT and stable DN-SUN HaCaT clones (FIG. 6A) grown at 60% confluency under standard 2D conditions indicates drastic changes in the overall appearance of the mutants. While both WT and DN-SUNL form colonies the latter appear to contain more cells, which exhibit strong cortical F-actin staining and a smaller circumference. Statistical analysis indicates that DN-SUNL HaCaT cells display a significantly smaller cellular area of 262 µm² compared to a calculated cell area of 473 µm² for WT cells. This drastic difference in the DN-SUNL cell area is reflected also in the number of cells that occupy a 100×100 m area. On average 7.4 WT cells are found within a 10000 µm² colony area, while for DN-SUNL 15.8 cells were observed (FIG. 6B). The pronounced cellular crowding effect of DN-SUNL may be the outcome of higher E-cadherin expression, which hinds the presence of enhanced cell-cell contacts when the cells are grown on 2D surfaces (FIG. 6C). Interestingly, the DN-SUNL effects on the expression of E-cadherin appear to be attenuated upon 3D cell culture (FIG. 6C).

Example 5-LINC Complex Disruption Alters Cell-Substratum Adhesion

Considering that DN-SUNL expressing cells display a drastically smaller cellular area, the inventors elucidated whether the adhesion of the cells to the surface has been altered. Examination of vinculin indeed indicates alterations in the localisation of the protein within the cytoplasm in DN-SUNL mutant cells. In WT cells the majority of vinculin is localised at focal contacts, which can be seen as distinct large clusters at the periphery of the cells (denoted by arrows, FIG. 7A). Moreover, WT cells appear very flat, which is evident not only by the presence of focal contacts but also from the large area that is occupied by the cytoplasm. In sharp contrast, DN-SUNL cells exhibit vinculin staining, which is confined in the cytoplasm and lack distinct focal contacts at the periphery (FIG. 7B). Western blot analysis of equal amounts of WT, and DN-SUNL cell lysates (two clones were examined) indicates that the levels of vinculin are not affected in the mutants. In summary, the data show that the subcellular distribution of vinculin is affected but not its expression levels upon LINC complex disruption in HaCaT keratinocytes. Moreover, the data suggest that a reduced cell-substratum attachment and an enhanced cell-cell adhesion may account for the cell density and morphological phenotype of the mutants.

Example 6-LINC Complex Disruption Enhances the Stratification Properties of HaCaT Keratinocytes in 2D Cell Culture Conditions Upon exposure to the air-liquid interphase keratinocytes start to differentiate and form a multi-layered structure. Cellular division is restricted to the cells that are in immediate contact with the cell culture media, while differentiated cells significantly flatten and occupy the areas that are further away from the media surface. Irrespectively, of whether DN-SUN HaCaT cells are grown alone (single culture) or in the presence of fibroblasts (co-culture) in 3D their ability of forming multi-layered cell assemblies is profoundly enhanced when compared to WT cells. FIG. 8A indicates that DN-SUNL cells form more layers when compared to WT. In addition, FIG. 8A shows that the DN cell layers occupy the area above the scaffold and that the differentiation programme is executed properly considering the drastic cell shape changes that occur in the upper layers (note the significant cell flattening that occurs in the co-culture permutation). The ability of the DN cells to form pronounced structures above the scaffold is shown in FIG. 8B. As can be seen DN-cells (GFP-positive due to DN-SUNL expression) grow both into (GFP-panel) and above the scaffold (Nile red co-stained sample). Note the presence of GFP-positive structures above the Nile red stained 3D scaffold, which shows that cell stacking occurs above the scaffold (FIG. 8B) and is enhanced upon LINC disruption (FIG. 8C).

Example 7—LINC Complex Disruption Enhances Cell Stratification and Differentiation To elucidate whether the morphological alterations (pronounced cell/nuclear flattening) exhibited by DN-SUNL cells (FIG. 9A, small arrows) correspond to differentiated cells the epidermal models were counterstained with Keratin 10. As can be seen in FIG. 9B, the anti-Keratin 10 immunofluorescence indicates that keratin 10 is present in the outermost cell layers of the DN-SUNL epidermal equivalent. In summary, FIG. 9 shows that DN-SUNL cells (relative to WT cells) have enhanced stratification properties, a proper spatial expression of the K10 differentiation marker when grown at the air-liquid interface in 3D and a cell morphology that mimics the shapes of keratinocytes of skin (e.g. columnar shape for cells in the direct vicinity of the scaffold [FIG. 9A, asterisks], and a squamous appearance for differentiated cells [FIG. 9A, small arrows]).

Example 8—DN-SUNL Expression Disrupts the Linkage of the INM to the ONM

To demonstrate that DN-SUNL disrupts the physical linkage of the inner nuclear membrane to the outer nuclear membrane (FIG. 10A) we performed an EM analysis of the DN-SUNL cells relative to WT. EM images indicate that the lumen of the nuclear envelope (NE) is even and narrow in WT, while DN-SUNL cells exhibit dilations (FIG. 10B). Measurements of the NE lumen indicate a significant dilation in DN-SUN expressing cells (FIG. 10).

Example 9—LINC Disruption Yields Compact, Taller and Softer Cell Colonies

To examine the physical properties of WT and DN-SUNL cells the inventors performed an AFM analysis on living cells. The data in FIG. 1A verify that DN-SUNL colonies compared to WT are more compact and contain more cells (phase contrast). Moreover, Young's modulus measurements (FIG. 11A, middle panel) indicate that mutants are significantly softer irrespectively of the cellular regions that were assessed (Nuclear centre, nuclear rim and cytoplasm FIGS. 11B and 11C). Collectively, these data suggest that DN-SUNL cells exhibit softer nuclei and softer cytoplasms, suggesting that DN-SUNL expression yields softer cells, which is further substantiated by the pronounced cantilever indentation in the mutants (FIG. 11D). Finally, the height map in FIG. 11A (lower panel) shows that DN-SUNL cells are taller when compared to WT, which again underlines that LINC complex manipulation controls cell/colony architecture.

The invention claimed is:

1. A method of preparing skin tissue, the method comprising:
(i) contacting a skin cell with an agent that disrupts the linker of the nucleoskeleton and cytoskeleton (LINC) complex of the cell, wherein the agent comprises:
 a. a modified Sad1 and UNC-84 (SUN) protein that consists of a SUN domain; or
 b. an amino acid sequence of SEQ ID No: 27;
(ii) culturing the cell on a substrate comprising culture media to induce proliferation of the cell into a plurality of cells; and
(iii) removing a portion of culture media from the substrate such that the plurality of cells are disposed in an interface between culture media remaining on the substrate and air, to thereby induce differentiation of the cells into skin tissue, wherein the skin cell of step (i) is a keratinocyte.

2. The method according to claim 1, wherein the LINC complex comprises a SUN domain, wherein the SUN domain is encoded by a nucleotide sequence substantially as set out in SEQ ID No. 9, 11, 13, 15 and/or 17, or a variant or fragment thereof, or wherein the SUN domain comprises an amino acid nucleotide sequence substantially as set out in SEQ ID No. 10, 12, 14, 16 and/or 18, or a variant or fragment thereof.

3. The method according to claim 1, wherein the LINC complex comprises a SUN protein.

4. The method of claim 3, wherein the Nm SUN protein comprises a SUN domain.

5. The method according to claim 1, wherein step (ii) of the method comprises culturing the cell at 35 to 38° C. for at least 6, 12, 18, 24, 36, 48, 96 or 168 hours.

6. The method according to claim 1, wherein step (iii) of the method comprises culturing the cells at 35 to 38° C. for at least 6, 12, 18, 24, 36, 48, 96 or 168 hours.

7. The method according to claim 1, wherein the agent that disrupts the LINC complex is an agent that (i) reduces the concentration of a LINC complex protein compared to the concentration of the LINC complex protein in the absence of the agent, (ii) inhibits the binding of one LINC complex protein to another LINC complex protein, and/or (iii) promotes degradation of the LINC complex or one or more of the LINC complex proteins.

8. The method according to claim 1, wherein the agent that disrupts the LINC complex is an agent that inhibits binding of a Nesprin protein to a SUN protein.

9. The method of claim 8, wherein the agent inhibits binding of the Nesprin protein to the SUN protein by inhibiting binding of a KASH domain to a SUN domain.

10. The method according to claim 1, wherein the culture media and the cell are disposed on the surface of the substrate.

11. The method according to claim 10, wherein the substrate is an insert or a mesh that can be placed in a culture plate.

\* \* \* \* \*

SEQUENCE LISTING

```
<160> NUMBER OF SEQ ID NOS: 31

<210> SEQ ID NO 1
<211> LENGTH: 241
<212> TYPE: DNA
<213> ORGANISM: Homo sapiens

<400> SEQUENCE: 1
gtccacaaaa ggtggctccg attcctccct ttctgagcca gggccaggtc ggtccggccg      60
cggcttcctg ttcagagtcc tccgagcagc tcttcccctt cagcttctcc tgctcctcct     120
catcgggctt gcctgccttg taccaatgtc agaggaagac tacagctgtg ccctctccaa     180
caactttgcc cggtcattcc acccatgct cagatacacg aatggccctc ctccactctg     240
a                                                                      241

<210> SEQ ID NO 2
<211> LENGTH: 51
<212> TYPE: PRT
<213> ORGANISM: Homo sapiens

<400> SEQUENCE: 2

Ala Ala Leu Pro Leu Gln Leu Leu Leu Leu Leu Ile Gly Leu Ala
1               5                   10                  15

Cys Leu Val Pro Met Ser Glu Glu Asp Tyr Ser Cys Ala Leu Ser Asn
            20                  25                  30

Asn Phe Ala Arg Ser Phe His Pro Met Leu Arg Tyr Thr Asn Gly Pro
        35                  40                  45

Pro Pro Leu
    50
```

<210> SEQ ID NO 3
<211> LENGTH: 208
<212> TYPE: DNA
<213> ORGANISM: Homo sapiens

<400> SEQUENCE: 3

```
ggtccccggc agcacacggc cacagcgctc cttcctctca agggtggtcc gggcagccct      60
acccctgcag ctgctcctcc tgctgctgct gctcctggcc tgcctgctgc cctcctccga     120
agaagactac agctgcactc aggccaacaa ctttgcccgg tccttttacc ccatgctgag     180
gtacaccaat gggccacccc ccacatag                                        208
```

<210> SEQ ID NO 4
<211> LENGTH: 51
<212> TYPE: PRT
<213> ORGANISM: Homo sapiens

<400> SEQUENCE: 4

```
Ala Ala Leu Pro Leu Gln Leu Leu Leu Leu Leu Leu Leu Leu Leu Ala
1               5                   10                  15

Cys Leu Leu Pro Ser Ser Glu Glu Asp Tyr Ser Cys Thr Gln Ala Asn
            20                  25                  30

Asn Phe Ala Arg Ser Phe Tyr Pro Met Leu Arg Tyr Thr Asn Gly Pro
        35                  40                  45

Pro Pro Thr
    50
```

<210> SEQ ID NO 5
<211> LENGTH: 201
<212> TYPE: DNA
<213> ORGANISM: Homo sapiens

<400> SEQUENCE: 5

```
actcggcggt ggcgaggact gggctccctc ttccggaggg cgtgctgtgt ggcgctccca      60
ctgcagctgc ttctgctgct gttcctcctc ctgctgttcc tgctcccaat cagggaagag     120
gaccgcagct gcaccctggc caacaacttc gcccgctcct tcacgctcat gctgcgctac     180
aatggcccac cacccaccta a                                               201
```

<210> SEQ ID NO 6
<211> LENGTH: 50
<212> TYPE: PRT
<213> ORGANISM: Homo sapiens

<400> SEQUENCE: 6

```
Val Ala Leu Pro Leu Gln Leu Leu Leu Leu Phe Leu Leu Leu
1               5                   10                  15

Phe Leu Leu Pro Ile Arg Glu Glu Asp Arg Ser Cys Thr Leu Ala Asn
            20                  25                  30

Asn Phe Ala Arg Ser Phe Thr Leu Met Leu Arg Tyr Asn Gly Pro Pro
        35                  40                  45

Pro Thr
    50
```

<210> SEQ ID NO 7
<211> LENGTH: 184
<212> TYPE: DNA
<213> ORGANISM: Homo sapiens

<400> SEQUENCE: 7

```
ggcccccgat cctgcatcca ggcagcctct gaccttcctc cttatcctct tcctcctctt      60
cctcctcctg gtgggtgcca tgtttctcct gcccgcgtca ggaggcccct gctgctctca     120
tgcccgaata cccaggacac cctacctggt gctcagctat gtcaatggtc ttcccccagt     180
ctga                                                                  184
```

<210> SEQ ID NO 8
<211> LENGTH: 49
<212> TYPE: PRT
<213> ORGANISM: Homo sapiens

<400> SEQUENCE: 8

```
Phe Leu Leu Ile Leu Phe Leu Leu Phe Leu Leu Leu Val Gly Ala Met
1               5                   10                  15
Phe Leu Leu Pro Ala Ser Gly Gly Pro Cys Cys Ser His Ala Arg Ile
            20                  25                  30
Pro Arg Thr Pro Tyr Leu Val Leu Ser Tyr Val Asn Gly Leu Pro Pro
        35                  40                  45
Val
```

<210> SEQ ID NO 9
<211> LENGTH: 494
<212> TYPE: DNA
<213> ORGANISM: Homo sapiens

<400> SEQUENCE: 9

```
gtggcagcat cttgagtact cgctgttctg aaacttacga aaccaaaacg gcgctgatga      60
gtctgtttgg gatcccgctg tggtacttct cgcagtcccc gcgcgtggtc atccagcctg     120
acatttaccc cggtaactgc tgggcattta aaggctccca ggggtacctg gtggtgaggc     180
tctccatgat gatccaccca gccgccttca ctctggagca catccctaag acgctgtcgc     240
caacaggcaa catcagcagc gcccccaagg acttcgccgt ctatggatta gaaaatgagt     300
atcaggaaga agggcagctt ctgggacagt tcacgtatga tcaggatggg gagtcgctcc     360
agatgttcca ggccctgaaa agacccgacg acacagcttt ccaaatagtg gaacttcgga     420
ttttttctaa ctggggccat cctgagtata cctgtctgta tcggttcaga gttcatggcg     480
aacctgtcaa gtga                                                       494
```

<210> SEQ ID NO 10
<211> LENGTH: 163
<212> TYPE: PRT
<213> ORGANISM: Homo sapiens

<400> SEQUENCE: 10

```
Gly Ser Ile Leu Ser Thr Arg Cys Ser Glu Thr Tyr Glu Thr Lys Thr
1               5                   10                  15
Ala Leu Met Ser Leu Phe Gly Ile Pro Leu Trp Tyr Phe Ser Gln Ser
            20                  25                  30
Pro Arg Val Val Ile Gln Pro Asp Ile Tyr Pro Gly Asn Cys Trp Ala
        35                  40                  45
Phe Lys Gly Ser Gln Gly Tyr Leu Val Val Arg Leu Ser Met Met Ile
    50                  55                  60
His Pro Ala Ala Phe Thr Leu Glu His Ile Pro Lys Thr Leu Ser Pro
65                  70                  75                  80
Thr Gly Asn Ile Ser Ser Ala Pro Lys Asp Phe Ala Val Tyr Gly Leu
```

```
                         85                  90                  95
Glu Asn Glu Tyr Gln Glu Gly Gln Leu Leu Gly Gln Phe Thr Tyr
                100                 105                 110

Asp Gln Asp Gly Glu Ser Leu Gln Met Phe Gln Ala Leu Lys Arg Pro
                115                 120                 125

Asp Asp Thr Ala Phe Gln Ile Val Glu Leu Arg Ile Phe Ser Asn Trp
        130                 135                 140

Gly His Pro Glu Tyr Thr Cys Leu Tyr Arg Phe Arg Val His Gly Glu
145                 150                 155                 160

Pro Val Lys

<210> SEQ ID NO 11
<211> LENGTH: 490
<212> TYPE: DNA
<213> ORGANISM: Homo sapiens

<400> SEQUENCE: 11
gggccagcgt catcagcacc cgatgttctg agacctacga gaccaagacg gccctcctca    60
gcctcttcgg catccccctg tggtaccact cccagtcacc ccgagtcatc ctccagccag   120
atgtgcaccc aggcaactgc tgggccttcc aggggccaca aggcttcgcc gtggtccgcc   180
tctctgcccg catccgcccc acagccgtta ccttagagca tgtgcccaag gccttgtcac   240
ccaacagcac tatctccagt gcccccaagg acttcgccat ctttgggttt gacgaagacc   300
tgcagcagga ggggacactc cttggcaagt tcacttacga tcaggacggc gagcctattc   360
agacgtttca ctttcaggcc cctacgatgg ccacgtacca ggtggtggag ctgcggatcc   420
tgactaactg gggccacccc gagtacacct gcatctaccg cttcagagtg catggggagc   480
ccgcccacta                                                          490

<210> SEQ ID NO 12
<211> LENGTH: 162
<212> TYPE: PRT
<213> ORGANISM: Homo sapiens

<400> SEQUENCE: 12

Ala Ser Val Ile Ser Thr Arg Cys Ser Glu Thr Tyr Glu Thr Lys Thr
1               5                   10                  15

Ala Leu Leu Ser Leu Phe Gly Ile Pro Leu Trp Tyr His Ser Gln Ser
            20                  25                  30

Pro Arg Val Ile Leu Gln Pro Asp Val His Pro Gly Asn Cys Trp Ala
        35                  40                  45

Phe Gln Gly Pro Gln Gly Phe Ala Val Val Arg Leu Ser Ala Arg Ile
    50                  55                  60

Arg Pro Thr Ala Val Thr Leu Glu His Val Pro Lys Ala Leu Ser Pro
65                  70                  75                  80

Asn Ser Thr Ile Ser Ser Ala Pro Lys Asp Phe Ala Ile Phe Gly Phe
                85                  90                  95

Asp Glu Asp Leu Gln Gln Glu Gly Thr Leu Leu Gly Lys Phe Thr Tyr
                100                 105                 110

Asp Gln Asp Gly Glu Pro Ile Gln Thr Phe His Phe Gln Ala Pro Thr
            115                 120                 125

Met Ala Thr Tyr Gln Val Val Glu Leu Arg Ile Leu Thr Asn Trp Gly
        130                 135                 140

His Pro Glu Tyr Thr Cys Ile Tyr Arg Phe Arg Val His Gly Glu Pro
145                 150                 155                 160
```

Ala His

<210> SEQ ID NO 13
<211> LENGTH: 497
<212> TYPE: DNA
<213> ORGANISM: Homo sapiens

<400> SEQUENCE: 13

```
gagcctccat cattgaagct gggacctcag aaagttataa aataataaa gcaaaattgt      60
actggcatgg gataggtttc ctaaatcatg aaatgcctcc agatattatt cttcagccgg    120
atgtctaccc tggaaagtgc tgggcttttc caggttccca gggtcatacc ctaatcaagc    180
ttgctacaaa gatcatacca actgctgtta ccatggagca catctcagag aaggtgtctc    240
cgtcaggaaa catctccagt gcacccaagg aattttctgt ctatggcatc acaaaaaaat    300
gtgaaggaga agaaattttc ctaggtcagt ttatataaa caaacagga accaccgttc      360
aaacatttga actccagcat gcagtttctg aatatttatt atgtgtgaaa cttaatatct    420
ttagcaactg gggacacccg aagtatactt gtttatatcg attcagggtc catggcacac    480
caggcaagca catctag                                                   497
```

<210> SEQ ID NO 14
<211> LENGTH: 164
<212> TYPE: PRT
<213> ORGANISM: Homo sapiens

<400> SEQUENCE: 14

```
Ala Ser Ile Ile Glu Ala Gly Thr Ser Glu Ser Tyr Lys Asn Asn Lys
1               5                  10                  15

Ala Lys Leu Tyr Trp His Gly Ile Gly Phe Leu Asn His Glu Met Pro
            20                  25                  30

Pro Asp Ile Ile Leu Gln Pro Asp Val Tyr Pro Gly Lys Cys Trp Ala
        35                  40                  45

Phe Pro Gly Ser Gln Gly His Thr Leu Ile Lys Leu Ala Thr Lys Ile
    50                  55                  60

Ile Pro Thr Ala Val Thr Met Glu His Ile Ser Glu Lys Val Ser Pro
65                  70                  75                  80

Ser Gly Asn Ile Ser Ser Ala Pro Lys Glu Phe Ser Val Tyr Gly Ile
                85                  90                  95

Thr Lys Lys Cys Glu Gly Glu Glu Ile Phe Leu Gly Gln Phe Ile Tyr
            100                 105                 110

Asn Lys Thr Gly Thr Thr Val Gln Thr Phe Glu Leu Gln His Ala Val
        115                 120                 125

Ser Glu Tyr Leu Leu Cys Val Lys Leu Asn Ile Phe Ser Asn Trp Gly
    130                 135                 140

His Pro Lys Tyr Thr Cys Leu Tyr Arg Phe Arg Val His Gly Thr Pro
145                 150                 155                 160

Gly Lys His Ile
```

<210> SEQ ID NO 15
<211> LENGTH: 521
<212> TYPE: DNA
<213> ORGANISM: Homo sapiens

<400> SEQUENCE: 15

```
gagcctccat cgacctgcag aagacatccc acgattacgc agacaggaac actgcctact      60
```

```
tctggaatcg cttcagcttc tggaactacg cacggccgcc cacggttatc ctggagcccc    120
acgtgttccc tgggaattgc tgggcttttg aaggcgacca aggccaggtg gtgatccaac    180
tgccgggccg agtgcagctg agcgacatca ctctgcagca tccaccgccc agcgtggagc    240
acaccggagg agccaacagc gcccccccgcg atttcgcggt cttttggcctc caggtttatg    300 atgaaactga agtttccttg gggaaattca ccttcgatgt tgagaaatcg agattcaga    360 ctttccacct gcagaatgac cccccagctg ccttttcccaa ggtgaagatc cagattctaa    420
gcaactgggg ccaccccgt tcacgtgct tgtatcgagt ccgtgccac ggtgtgcgaa    480 cctcagaggg ggcagagggc agtgcacagg ggccccatta a    521
```

<210> SEQ ID NO 16
<211> LENGTH: 172
<212> TYPE: PRT
<213> ORGANISM: Homo sapiens

<400> SEQUENCE: 16

```
Ala Ser Ile Asp Leu Gln Lys Thr Ser His Asp Tyr Ala Asp Arg Asn
1               5                   10                  15

Thr Ala Tyr Phe Trp Asn Arg Phe Ser Phe Trp Asn Tyr Ala Arg Pro
            20                  25                  30

Pro Thr Val Ile Leu Glu Pro His Val Phe Pro Gly Asn Cys Trp Ala
        35                  40                  45

Phe Glu Gly Asp Gln Gly Gln Val Val Ile Gln Leu Pro Gly Arg Val
    50                  55                  60

Gln Leu Ser Asp Ile Thr Leu Gln His Pro Pro Pro Ser Val Glu His
65                  70                  75                  80

Thr Gly Gly Ala Asn Ser Ala Pro Arg Asp Phe Ala Val Phe Gly Leu
                85                  90                  95

Gln Val Tyr Asp Glu Thr Glu Val Ser Leu Gly Lys Phe Thr Phe Asp
            100                 105                 110

Val Glu Lys Ser Glu Ile Gln Thr Phe His Leu Gln Asn Asp Pro Pro
        115                 120                 125

Ala Ala Phe Pro Lys Val Lys Ile Gln Ile Leu Ser Asn Trp Gly His
    130                 135                 140

Pro Arg Phe Thr Cys Leu Tyr Arg Val Arg Ala His Gly Val Arg Thr
145                 150                 155                 160

Ser Glu Gly Ala Glu Gly Ser Ala Gln Gly Pro His
                165                 170
```

<210> SEQ ID NO 17
<211> LENGTH: 527
<212> TYPE: DNA
<213> ORGANISM: Homo sapiens

<400> SEQUENCE: 17

```
gggccagcat tgactttgag cacacgtcag tcacctataa ccatgagaag gcccactcct     60
actggaactg gatccagctg tggaactacg cacagccccc agacgtgatc cttgagccca    120
acgtgacacc tggcaattgc tgggcctttg agggtgaccg cggccaggtg accatccaat    180
tggctcagaa ggtttacctg tccaacctca cgctgcagca catccccaag accatctcat    240
tgtcaggcag cctggacacc gcccccaagg acttcgtcat ctatggcatg gagggctccc    300
ccaaggagga ggtgttcctg ggggcatttc agtttcagcc agaaaacatc atccagatgt    360
tcccactcca gaaccagccg gcccgggctt tcagtgcggt caaggtgaag atctcaagca    420
```

-continued

```
actgggggaa cccaggcttc acttgcctgt accgcgtgcg agtgcatggc tctgtggccc 480
cgcccagaga gcagcctcac cagaacccct accctaagag agattaa 527
```

<210> SEQ ID NO 18
<211> LENGTH: 174
<212> TYPE: PRT
<213> ORGANISM: Homo sapiens

<400> SEQUENCE: 18

```
Ala Ser Ile Asp Phe Glu His Thr Ser Val Thr Tyr Asn His Glu Lys
1 5 10 15

Ala His Ser Tyr Trp Asn Trp Ile Gln Leu Trp Asn Tyr Ala Gln Pro
20 25 30

Pro Asp Val Ile Leu Glu Pro Asn Val Thr Pro Gly Asn Cys Trp Ala
35 40 45

Phe Glu Gly Asp Arg Gly Gln Val Thr Ile Gln Leu Ala Gln Lys Val
50 55 60

Tyr Leu Ser Asn Leu Thr Leu Gln His Ile Pro Lys Thr Ile Ser Leu
65 70 75 80

Ser Gly Ser Leu Asp Thr Ala Pro Lys Asp Phe Val Ile Tyr Gly Met
85 90 95

Glu Gly Ser Pro Lys Glu Glu Val Phe Leu Gly Ala Phe Gln Phe Gln
100 105 110

Pro Glu Asn Ile Ile Gln Met Phe Pro Leu Gln Asn Gln Pro Ala Arg
115 120 125

Ala Phe Ser Ala Val Lys Val Lys Ile Ser Ser Asn Trp Gly Asn Pro
130 135 140

Gly Phe Thr Cys Leu Tyr Arg Val Arg Val His Gly Ser Val Ala Pro
145 150 155 160

Pro Arg Glu Gln Pro His Gln Asn Pro Tyr Pro Lys Arg Asp
165 170
```

<210> SEQ ID NO 19
<211> LENGTH: 1995
<212> TYPE: DNA
<213> ORGANISM: Homo sapiens

<400> SEQUENCE: 19

```
atggagaccc cgtcccagcg gcgcgccacc cgcagcgggg cgcaggccag ctccactccg 60
ctgtcgccca cccgcatcac ccggctgcag gagaaggagg acctgcagga gctcaatgat 120
cgcttggcgg tctacatcga ccgtgtgcgc tcgctggaaa cggagaacgc agggctgcgc 180
cttcgcatca ccgagtctga agaggtggtc agccgcgagg tgtccggcat caaggccgcc 240
tacgaggccg agctcgggga tgcccgcaag acccttgact cagtagccaa ggagcgcgcc 300
cgcctgcagc tggagctgag caaagtgcgt gaggagttta aggagctgaa agcgcgcaat 360
accaagaagg agggtgacct gatagctgct caggctcggc tgaaggacct ggaggctctg 420
ctgaactcca aggaggccgc actgagcact gctctcagtg agaagcgcac gctggagggc 480
gagctgcatg atctgcgggg ccaggtggcc aagcttgagg cagccctagg tgaggccaag 540
aagcaacttc aggatgagat gctgcggcgg gtggatgctg agaacaggct gcagaccatg 600
aaggaggaac tggacttcca gaagaacatc tacagtgagg agctgcgtga gaccaagcgc 660
```

```
cgtcatgaga cccgactggt ggagattgac aatgggaagc agcgtgagtt tgagagccgg 720
ctggcggatg cgctgcagga actgcgggcc cagcatgagg accaggtgga gcagtataag 780
```

```
aaggagctgg agaagactta ttctgccaag ctggacaatg ccaggcagtc tgctgagagg    840
aacagcaacc tggtgggggc tgcccacgag gagctgcagc agtcgcgcat ccgcatcgac    900
agcctctctg cccagctcag ccagctccag aagcagctgg cagccaagga ggcgaagctt    960
cgagacctgg aggactcact ggcccgtgag cgggacacca gccggcggct gctggcggaa   1020
aaggagcggg agatggccga gatgcgggca aggatgcagc agcagctgga cgagtaccag   1080
gagcttctgg acatcaagct ggccctggac atggagatcc acgcctaccg caagctcttg   1140
gagggcgagg aggagaggct acgcctgtcc cccagcccta cctcgcagcg cagccgtggc   1200
cgtgcttcct ctcactcatc ccagacacag ggtgggggca cgtcaccaa aaagcgcaaa    1260 ctggagtcca ctgagagccg cagcagcttc tcacagcacg cacgcactag cgggcgcgtg   1320
gccgtggagg aggtggatga ggagggcaag tttgtccggc tgcgcaacaa gtccaatgag   1380
gaccagtcca tgggcaattg cagatcaag cgccagaatg gagatgatcc cttgctgact    1440
taccggttcc caccaaagtt caccctgaag gctgggcagg tggtgacgat ctgggctgca   1500
ggagctgggg ccacccacag cccccctacc gacctggtgt ggaaggcaca gaacacctgg   1560
ggctgcggga acagcctgcg tacggctctc atcaactcca ctggggaaga agtggccatg   1620
cgcaagctgt gcgctcagt gactgtggtt gaggacgacg aggatgagga tggagatgac   1680
ctgctccatc accaccacgg ctcccactgc agcagctcgg gggaccccgc tgagtacaac   1740
ctgcgctcgc gcaccgtgct gtgcgggacc tgcgggcagc tgccgacaa ggcatctgcc    1800 agcggctcag gagcccaggt gggcggaccc atctcctctg gctcttctgc ctccagtgtc   1860
acggtcactc gcagctaccg cagtgtgggg ggcagtgggg gtggcagctt cggggacaat   1920
ctggtcaccc gctcctacct cctgggcaac tccagccccc gaacccagag cccccagaac   1980
tgcagcatca tgtaa                                                    1995
```

```
<210> SEQ ID NO 20
<211> LENGTH: 664
<212> TYPE: PRT
<213> ORGANISM: Homo sapiens

<400> SEQUENCE: 20

Met Glu Thr Pro Ser Gln Arg Arg Ala Thr Arg Ser Gly Ala Gln Ala
1               5                   10                  15

Ser Ser Thr Pro Leu Ser Pro Thr Arg Ile Thr Arg Leu Gln Glu Lys
            20                  25                  30

Glu Asp Leu Gln Glu Leu Asn Asp Arg Leu Ala Val Tyr Ile Asp Arg
        35                  40                  45

Val Arg Ser Leu Glu Thr Glu Asn Ala Gly Leu Arg Leu Arg Ile Thr
    50                  55                  60

Glu Ser Glu Glu Val Val Ser Arg Glu Val Ser Gly Ile Lys Ala Ala
65                  70                  75                  80

Tyr Glu Ala Glu Leu Gly Asp Ala Arg Lys Thr Leu Asp Ser Val Ala
                85                  90                  95

Lys Glu Arg Ala Arg Leu Gln Leu Glu Leu Ser Lys Val Arg Glu Glu
            100                 105                 110

Phe Lys Glu Leu Lys Ala Arg Asn Thr Lys Lys Glu Gly Asp Leu Ile
        115                 120                 125

Ala Ala Gln Ala Arg Leu Lys Asp Leu Glu Ala Leu Leu Asn Ser Lys
    130                 135                 140

Glu Ala Ala Leu Ser Thr Ala Leu Ser Glu Lys Arg Thr Leu Glu Gly
145                 150                 155                 160
```

```
Glu Leu His Asp Leu Arg Gly Gln Val Ala Lys Leu Glu Ala Ala Leu
                165                 170                 175
Gly Glu Ala Lys Lys Gln Leu Gln Asp Glu Met Leu Arg Arg Val Asp
            180                 185                 190
Ala Glu Asn Arg Leu Gln Thr Met Lys Glu Glu Leu Asp Phe Gln Lys
        195                 200                 205
Asn Ile Tyr Ser Glu Glu Leu Arg Glu Thr Lys Arg Arg His Glu Thr
    210                 215                 220
Arg Leu Val Glu Ile Asp Asn Gly Lys Gln Arg Glu Phe Glu Ser Arg
225                 230                 235                 240
Leu Ala Asp Ala Leu Gln Glu Leu Arg Ala Gln His Glu Asp Gln Val
                245                 250                 255
Glu Gln Tyr Lys Lys Glu Leu Glu Lys Thr Tyr Ser Ala Lys Leu Asp
            260                 265                 270
Asn Ala Arg Gln Ser Ala Glu Arg Asn Ser Asn Leu Val Gly Ala Ala
        275                 280                 285
His Glu Glu Leu Gln Gln Ser Arg Ile Arg Ile Asp Ser Leu Ser Ala
    290                 295                 300
Gln Leu Ser Gln Leu Gln Lys Gln Leu Ala Ala Lys Glu Ala Lys Leu
305                 310                 315                 320
Arg Asp Leu Glu Asp Ser Leu Ala Arg Glu Arg Asp Thr Ser Arg Arg
                325                 330                 335
Leu Leu Ala Glu Lys Glu Arg Glu Met Ala Glu Met Arg Ala Arg Met
            340                 345                 350
Gln Gln Gln Leu Asp Glu Tyr Gln Glu Leu Leu Asp Ile Lys Leu Ala
        355                 360                 365
Leu Asp Met Glu Ile His Ala Tyr Arg Lys Leu Leu Glu Gly Glu Glu
    370                 375                 380
Glu Arg Leu Arg Leu Ser Pro Ser Pro Thr Ser Gln Arg Ser Arg Gly
385                 390                 395                 400
Arg Ala Ser Ser His Ser Ser Gln Thr Gln Gly Gly Gly Ser Val Thr
                405                 410                 415
Lys Lys Arg Lys Leu Glu Ser Thr Glu Ser Arg Ser Ser Phe Ser Gln
            420                 425                 430
His Ala Arg Thr Ser Gly Arg Val Ala Val Glu Glu Val Asp Glu Glu
        435                 440                 445
Gly Lys Phe Val Arg Leu Arg Asn Lys Ser Asn Glu Asp Gln Ser Met
    450                 455                 460
Gly Asn Trp Gln Ile Lys Arg Gln Asn Gly Asp Asp Pro Leu Leu Thr
465                 470                 475                 480
Tyr Arg Phe Pro Pro Lys Phe Thr Leu Lys Ala Gly Gln Val Val Thr
                485                 490                 495
Ile Trp Ala Ala Gly Ala Gly Ala Thr His Ser Pro Thr Asp Leu
            500                 505                 510
Val Trp Lys Ala Gln Asn Thr Trp Gly Cys Gly Asn Ser Leu Arg Thr
        515                 520                 525
Ala Leu Ile Asn Ser Thr Gly Glu Glu Val Ala Met Arg Lys Leu Val
    530                 535                 540
Arg Ser Val Thr Val Val Glu Asp Asp Glu Asp Glu Asp Gly Asp Asp
545                 550                 555                 560
Leu Leu His His His His Gly Ser His Cys Ser Ser Ser Gly Asp Pro
                565                 570                 575
```

-continued

```
Ala Glu Tyr Asn Leu Arg Ser Arg Thr Val Leu Cys Gly Thr Cys Gly
            580                 585                 590

Gln Pro Ala Asp Lys Ala Ser Ala Ser Gly Ser Gly Ala Gln Val Gly
        595                 600                 605

Gly Pro Ile Ser Ser Gly Ser Ser Ala Ser Ser Val Thr Val Thr Arg
    610                 615                 620

Ser Tyr Arg Ser Val Gly Gly Ser Gly Gly Gly Ser Phe Gly Asp Asn
625                 630                 635                 640

Leu Val Thr Arg Ser Tyr Leu Leu Gly Asn Ser Ser Pro Arg Thr Gln
                645                 650                 655

Ser Pro Gln Asn Cys Ser Ile Met
        660
```

```
<210> SEQ ID NO 21
<211> LENGTH: 1719
<212> TYPE: DNA
<213> ORGANISM: Homo sapiens

<400> SEQUENCE: 21
```

| | |
|---|---|
| atggagaccc cgtcccagcg gcgcgccacc cgcagcgggg cgcaggccag ctccactccg | 60 |
| ctgtcgccca cccgcatcac ccggctgcag gagaaggagg acctgcagga gctcaatgat | 120 |
| cgcttggcgg tctacatcga ccgtgtgcgc tcgctggaaa cggagaacgc agggctgcgc | 180 |
| cttcgcatca ccgagtctga agaggtggtc agccgcgagg tgtccggcat caaggccgcc | 240 |
| tacgaggccg agctcgggga tgcccgcaag acccttgact cagtagccaa ggagcgcgcc | 300 |
| cgcctgcagc tggagctgag caaagtgcgt gaggagttta aggagctgaa agcgcgcaat | 360 |
| accaagaagg agggtgacct gatagctgct caggctcggc tgaaggacct ggaggctctg | 420 |
| ctgaactcca aggaggccgc actgagcact gctctcagtg agaagcgcac gctggagggc | 480 |
| gagctgcatg atctgcgggg ccaggtggcc aagcttgagg cagccctagg tgaggccaag | 540 |
| aagcaacttc aggatgagat gctgcggcgg gtggatgctg agaacaggct gcagaccatg | 600 |
| aaggaggaac tggacttcca agaacatc tacagtgagg agctgcgtga ccaagcgc | 660 |
| cgtcatgaga cccgactggt ggagattgac aatgggaagc agcgtgagtt tgagagccgg | 720 |
| ctggcggatg cgctgcagga actgcgggcc cagcatgagg accaggtgga gcagtataag | 780 |
| aaggagctgg agaagactta ttctgccaag ctggacaatg ccaggcagtc tgctgagagg | 840 |
| aacagcaacc tggtgggggc tgcccacgag gagctgcagc agtcgcgcat ccgcatcgac | 900 |
| agcctctctg cccagctcag ccagctccag aagcagctgg cagccaagga ggcgaagctt | 960 |
| cgagacctgg aggactcact ggcccgtgag cgggacacca gccggcggct gctggcggaa | 1020 |
| aaggagcggg agatggccga gatgcgggca aggatgcagc agcagctgga cgagtaccag | 1080 |
| gagcttctgg acatcaagct ggccctggac atggagatcc acgcctaccg caagctcttg | 1140 |
| gagggcgagg aggagaggct acgcctgtcc cccagcccta cctcgcagcg cagccgtggc | 1200 |
| cgtgcttcct ctcactcatc ccagacacag ggtgggggca cgtcaccaa aaagcgcaaa | 1260 |
| ctggagtcca ctgagagccg cagcagcttc tcacagcacg cacgcactag cggcgcgtg | 1320 |
| gccgtggagg aggtggatga ggagggcaag tttgtccggc tgcgcaacaa gtccaatgag | 1380 |
| gaccagtcca tgggcaattg gcagatcaag cgccagaatg gagatgatcc cttgctgact | 1440 |
| taccggttcc caccaaagtt caccctgaag gctgggcagg tggtgacgat ctgggctgca | 1500 |
| ggagctgggg ccacccacag cccccctacc gacctggtgt ggaaggcaca gaacacctgg | 1560 |
| ggctgcggga acagcctgcg tacggctctc atcaactcca ctggggaaga agtggccatg | 1620 |

-continued

```
cgcaagctgg tgcgctcagt gactgtggtt gaggacgacg aggatgagga tggagatgac    1680
ctgctccatc accaccacgt gagtggtagc cgccgctga                            1719
```

<210> SEQ ID NO 22
<211> LENGTH: 572
<212> TYPE: PRT
<213> ORGANISM: Homo sapiens

<400> SEQUENCE: 22

```
Met Glu Thr Pro Ser Gln Arg Arg Ala Thr Arg Ser Gly Ala Gln Ala
1               5                   10                  15

Ser Ser Thr Pro Leu Ser Pro Thr Arg Ile Thr Arg Leu Gln Glu Lys
            20                  25                  30

Glu Asp Leu Gln Glu Leu Asn Asp Arg Leu Ala Val Tyr Ile Asp Arg
        35                  40                  45

Val Arg Ser Leu Glu Thr Glu Asn Ala Gly Leu Arg Leu Arg Ile Thr
    50                  55                  60

Glu Ser Glu Glu Val Val Ser Arg Glu Val Ser Gly Ile Lys Ala Ala
65                  70                  75                  80

Tyr Glu Ala Glu Leu Gly Asp Ala Arg Lys Thr Leu Asp Ser Val Ala
                85                  90                  95

Lys Glu Arg Ala Arg Leu Gln Leu Glu Leu Ser Lys Val Arg Glu Glu
            100                 105                 110

Phe Lys Glu Leu Lys Ala Arg Asn Thr Lys Lys Glu Gly Asp Leu Ile
        115                 120                 125

Ala Ala Gln Ala Arg Leu Lys Asp Leu Glu Ala Leu Leu Asn Ser Lys
    130                 135                 140

Glu Ala Ala Leu Ser Thr Ala Leu Ser Glu Lys Arg Thr Leu Glu Gly
145                 150                 155                 160

Glu Leu His Asp Leu Arg Gly Gln Val Ala Lys Leu Glu Ala Ala Leu
                165                 170                 175

Gly Glu Ala Lys Lys Gln Leu Gln Asp Glu Met Leu Arg Arg Val Asp
            180                 185                 190

Ala Glu Asn Arg Leu Gln Thr Met Lys Glu Glu Leu Asp Phe Gln Lys
        195                 200                 205

Asn Ile Tyr Ser Glu Glu Leu Arg Glu Thr Lys Arg Arg His Glu Thr
    210                 215                 220

Arg Leu Val Glu Ile Asp Asn Gly Lys Gln Arg Glu Phe Glu Ser Arg
225                 230                 235                 240

Leu Ala Asp Ala Leu Gln Glu Leu Arg Ala Gln His Glu Asp Gln Val
                245                 250                 255

Glu Gln Tyr Lys Lys Glu Leu Glu Lys Thr Tyr Ser Ala Lys Leu Asp
            260                 265                 270

Asn Ala Arg Gln Ser Ala Glu Arg Asn Ser Asn Leu Val Gly Ala Ala
        275                 280                 285

His Glu Glu Leu Gln Gln Ser Arg Ile Arg Ile Asp Ser Leu Ser Ala
    290                 295                 300

Gln Leu Ser Gln Leu Gln Lys Gln Leu Ala Ala Lys Glu Ala Lys Leu
305                 310                 315                 320

Arg Asp Leu Glu Asp Ser Leu Ala Arg Glu Arg Asp Thr Ser Arg Arg
                325                 330                 335

Leu Leu Ala Glu Lys Glu Arg Glu Met Ala Glu Met Arg Ala Arg Met
            340                 345                 350
```

-continued

```
Gln Gln Gln Leu Asp Glu Tyr Gln Glu Leu Leu Asp Ile Lys Leu Ala
            355                 360                 365

Leu Asp Met Glu Ile His Ala Tyr Arg Lys Leu Leu Glu Gly Glu Glu
        370                 375                 380

Glu Arg Leu Arg Leu Ser Pro Ser Pro Thr Ser Gln Arg Ser Arg Gly
385                 390                 395                 400

Arg Ala Ser Ser His Ser Ser Gln Thr Gln Gly Gly Ser Val Thr
                405                 410                 415

Lys Lys Arg Lys Leu Glu Ser Thr Glu Ser Arg Ser Ser Phe Ser Gln
            420                 425                 430

His Ala Arg Thr Ser Gly Arg Val Ala Val Glu Glu Val Asp Glu Glu
        435                 440                 445

Gly Lys Phe Val Arg Leu Arg Asn Lys Ser Asn Glu Asp Gln Ser Met
    450                 455                 460

Gly Asn Trp Gln Ile Lys Arg Gln Asn Gly Asp Asp Pro Leu Leu Thr
465                 470                 475                 480

Tyr Arg Phe Pro Pro Lys Phe Thr Leu Lys Ala Gly Gln Val Val Thr
                485                 490                 495

Ile Trp Ala Ala Gly Ala Gly Ala Thr His Ser Pro Pro Thr Asp Leu
            500                 505                 510

Val Trp Lys Ala Gln Asn Thr Trp Gly Cys Gly Asn Ser Leu Arg Thr
        515                 520                 525

Ala Leu Ile Asn Ser Thr Gly Glu Glu Val Ala Met Arg Lys Leu Val
    530                 535                 540

Arg Ser Val Thr Val Val Glu Asp Asp Glu Asp Glu Asp Gly Asp Asp
545                 550                 555                 560

Leu Leu His His His His Val Ser Gly Ser Arg Arg
                565                 570
```

<210> SEQ ID NO 23
<211> LENGTH: 1761
<212> TYPE: DNA
<213> ORGANISM: Homo sapiens

<400> SEQUENCE: 23

| | | |
|---|---|---|
| atggcgactg cgacccccgt gccgccgcgg atgggcagcc gcgctggcgg ccccaccacg | 60 |
| ccgctgagcc ccacgcgcct gtcgcggctc caggagaagg aggagctgcg cgagctcaat | 120 |
| gaccggctgg cggtgtacat cgacaaggtg cgcagcctgg agacggagaa cagcgcgctg | 180 |
| cagctgcagg tgacggagcg cgaggaggtg cgcggccgtg agctcaccgg cctcaaggcg | 240 |
| ctctacgaga ccgagctggc cgacgcgcga cgcgcgctcg acgacacggc ccgcgagcgc | 300 |
| gccaagctgc agatcgagct gggcaagtgc aaggcggaac acgaccagct gctcctcaac | 360 |
| tatgctaaga aggaatctga tcttaatggc gcccagatca agcttcgaga atatgaagca | 420 |
| gcactgaatt cgaaagatgc agctcttgct actgcacttg gtgacaaaaa aagtttagag | 480 |
| ggagatttgg aggatctgaa ggatcagatt gcccagttgg aagcctcctt agctgcagcc | 540 |
| aaaaaacagt tagcagatga aactttactt aaagtagatt tggagaatcg ttgtcagagc | 600 |
| cttactgagg acttggagtt tcgcaaaagc atgtatgaag aggagattaa cgagaccaga | 660 |
| aggaagcatg aaacgcgctt ggtagaggtg gattctgggc gtcaaattga gtatgagtac | 720 |
| aagctggcgc aagcccttca tgagatgaga gagcaacatg atgcccaagt gaggctgtat | 780 |
| aaggaggagc tggagcagac ttaccatgcc aaacttgaga tgccagact gtcatcagag | 840 |
| atgaatactt ctactgtcaa cagtgccagg gaagaactga tggaaagccg catgagaatt | 900 |

```
gagagccttt catcccagct ttctaatcta cagaaagagt ctagagcatg tttggaaagg    960
attcaagaat tagaggactt gcttgctaaa gaaaaagaca actctcgtcg catgctgaca   1020
gacaaagaga gagagatggc ggaaataagg gatcaaatgc agcaacagct gaatgactat   1080
gaacagcttc ttgatgtaaa gttagccctg gacatggaaa tcagtgctta caggaaactc   1140
ttagaaggcg aagaagagag gttgaagctg tctccaagcc cttcttcccg tgtgacagta   1200
tcccgagcat cctcaagtcg tagtgtacgt acaactagag gaaagcggaa gagggttgat   1260
gtggaagaat cagaggcgag tagtagtgtt agcatctctc attccgcctc agccactgga   1320
aatgtttgca tcgaagaaat tgatgttgat gggaaattta ccgcttgaa gaacacttct    1380
gaacaggatc aaccaatggg aggctgggag atgatcagaa aaattggaga cacatcagtc   1440
agttataaat atacctcaag atatgtgctg aaggcaggcc agactgttac aatttgggct   1500
gcaaacgctg gtgtcacagc cagcccccca actgacctca tctggaagaa ccagaactcg   1560
tgggcactg gcgaagatgt gaaggttata ttgaaaaatt ctcagggaga ggaggttgct    1620
caaagaagta cagtctttaa aacaaccata cctgaagaag aggaggagga ggaagaagca   1680
gctggagtgg ttgttgagga agaactttc caccagcagg gaaccccaag agcatccaat    1740
agaagctgtg caattatgta a                                             1761
```

<210> SEQ ID NO 24
<211> LENGTH: 586
<212> TYPE: PRT
<213> ORGANISM: Homo sapiens
<400> SEQUENCE: 24

```
Met Ala Thr Ala Thr Pro Val Pro Pro Arg Met Gly Ser Arg Ala Gly
 1               5                   10                  15
Gly Pro Thr Thr Pro Leu Ser Pro Thr Arg Leu Ser Arg Leu Gln Glu
             20                  25                  30
Lys Glu Glu Leu Arg Glu Leu Asn Asp Arg Leu Ala Val Tyr Ile Asp
         35                  40                  45
Lys Val Arg Ser Leu Glu Thr Glu Asn Ser Ala Leu Gln Leu Gln Val
     50                  55                  60
Thr Glu Arg Glu Glu Val Arg Gly Arg Glu Leu Thr Gly Leu Lys Ala
 65                  70                  75                  80
Leu Tyr Glu Thr Glu Leu Ala Asp Ala Arg Arg Ala Leu Asp Asp Thr
                 85                  90                  95
Ala Arg Glu Arg Ala Lys Leu Gln Ile Glu Leu Gly Lys Cys Lys Ala
            100                 105                 110
Glu His Asp Gln Leu Leu Leu Asn Tyr Ala Lys Lys Glu Ser Asp Leu
        115                 120                 125
Asn Gly Ala Gln Ile Lys Leu Arg Glu Tyr Glu Ala Ala Leu Asn Ser
    130                 135                 140
Lys Asp Ala Ala Leu Ala Thr Ala Leu Gly Asp Lys Lys Ser Leu Glu
145                 150                 155                 160
Gly Asp Leu Glu Asp Leu Lys Asp Gln Ile Ala Gln Leu Glu Ala Ser
                165                 170                 175
Leu Ala Ala Ala Lys Lys Gln Leu Ala Asp Glu Thr Leu Leu Lys Val
            180                 185                 190
Asp Leu Glu Asn Arg Cys Gln Ser Leu Thr Glu Asp Leu Glu Phe Arg
        195                 200                 205
Lys Ser Met Tyr Glu Glu Glu Ile Asn Glu Thr Arg Arg Lys His Glu
```

```
            210                 215                 220
Thr Arg Leu Val Glu Val Asp Ser Gly Arg Gln Ile Glu Tyr Glu Tyr
225                 230                 235                 240

Lys Leu Ala Gln Ala Leu His Glu Met Arg Glu Gln His Asp Ala Gln
                245                 250                 255

Val Arg Leu Tyr Lys Glu Leu Glu Gln Thr Tyr His Ala Lys Leu
                260                 265                 270

Glu Asn Ala Arg Leu Ser Ser Glu Met Asn Thr Ser Thr Val Asn Ser
                275                 280                 285

Ala Arg Glu Glu Leu Met Glu Ser Arg Met Arg Ile Glu Ser Leu Ser
290                 295                 300

Ser Gln Leu Ser Asn Leu Gln Lys Glu Ser Arg Ala Cys Leu Glu Arg
305                 310                 315                 320

Ile Gln Glu Leu Glu Asp Leu Leu Ala Lys Lys Asp Asn Ser Arg
                325                 330                 335

Arg Met Leu Thr Asp Lys Glu Arg Glu Met Ala Glu Ile Arg Asp Gln
                340                 345                 350

Met Gln Gln Gln Leu Asn Asp Tyr Glu Gln Leu Leu Asp Val Lys Leu
                355                 360                 365

Ala Leu Asp Met Glu Ile Ser Ala Tyr Arg Lys Leu Leu Glu Gly Glu
                370                 375                 380

Glu Glu Arg Leu Lys Leu Ser Pro Ser Pro Ser Ser Arg Val Thr Val
385                 390                 395                 400

Ser Arg Ala Ser Ser Ser Arg Ser Val Arg Thr Thr Arg Gly Lys Arg
                405                 410                 415

Lys Arg Val Asp Val Glu Glu Ser Glu Ala Ser Ser Ser Val Ser Ile
                420                 425                 430

Ser His Ser Ala Ser Ala Thr Gly Asn Val Cys Ile Glu Glu Ile Asp
                435                 440                 445

Val Asp Gly Lys Phe Ile Arg Leu Lys Asn Thr Ser Glu Gln Asp Gln
                450                 455                 460

Pro Met Gly Gly Trp Glu Met Ile Arg Lys Ile Gly Asp Thr Ser Val
465                 470                 475                 480

Ser Tyr Lys Tyr Thr Ser Arg Tyr Val Leu Lys Ala Gly Gln Thr Val
                485                 490                 495

Thr Ile Trp Ala Ala Asn Ala Gly Val Thr Ala Ser Pro Pro Thr Asp
                500                 505                 510

Leu Ile Trp Lys Asn Gln Asn Ser Trp Gly Thr Gly Glu Asp Val Lys
                515                 520                 525

Val Ile Leu Lys Asn Ser Gln Gly Glu Glu Val Ala Gln Arg Ser Thr
530                 535                 540

Val Phe Lys Thr Thr Ile Pro Glu Glu Glu Glu Glu Glu Glu Glu Ala
545                 550                 555                 560

Ala Gly Val Val Val Glu Glu Glu Leu Phe His Gln Gln Gly Thr Pro
                565                 570                 575

Arg Ala Ser Asn Arg Ser Cys Ala Ile Met
                580                 585

<210> SEQ ID NO 25
<211> LENGTH: 1863
<212> TYPE: DNA
<213> ORGANISM: Homo sapiens

<400> SEQUENCE: 25
```

```
atgagcccgc cgagcccggg ccgccgtcgg gagcagcgca ggccgcgagc cgccgccacc      60
atggccacgc cgctgcccgg ccgcgcgggc gggcccgcca cgccgctgtc gcccacgcgc     120
ctgtcgcggc tgcaggagaa ggaggagctg cgcgagctca cgaccgcct ggcgcactac      180
atcgaccgcg tccgcgcgct ggagctggag aacgaccggc tcctgctcaa gatctcagag     240
aaggaggagg tgaccacgcg cgaggtgagt ggcatcaagg cgctgtacga gtcggagctg     300
gccgatgccc ggagagtcct ggatgagacg gctcgagagc gtgcccggct gcagatagag     360
attgggaagc tgagggcaga gttggacgag gtcaacaaga gcgccaagaa gagggagggc     420
gagcttacgg tggcccaggg ccgtgtgaag gacctggagt ccctgttcca ccggagcgag     480
gtggagctgg cagctgccct cagcgacaag cgcggcctgg agagtgacgt ggctgagctg     540
cgggcccagc tggccaaggc cgaggacggt catgcagtgg ccaaaaagca gctggagaag     600
gagacgctga tgcgtgtgga cctggagaac cgctgccaga gctgcagga ggagctggac      660
ttccggaaga gtgtgttcga ggaggaggtg cgggagacgc ggcggcggca cgagcggcgc     720
ctggtggagg tggacagcag ccggcagcag gagtacgact tcaagatggc acaggcgctg     780
gaggagctgc ggagccagca cgacgagcaa gtgcggctct acaagctgga gctggagcag     840
acctaccagg ccaagctgga cagcgccaag ctgagctctg accagaacga caaggcggcc     900
agtgcggctc gcgaggagct gaaggaggcc cgcatgcgcc tggagtccct cagctaccag     960
ctctccggcc tccagaagca ggccagtgcc gctgaagatc gcattcggga gctggaggag    1020
gccatggccg gggagcggga caagttccgg aagatgctgg acgccaagga gcaggagatg    1080
acggagatgc gggacgtgat gcagcagcag ctggccgagt accaggagct gctggacgtg    1140
aagctggccc tggacatgga gatcaacgcc taccggaagc tcctggaggg cgaggaggag    1200
aggctgaagc tgtcccccag cccatcctcg cgcgtcaccg tctcacgagc cacctcgagc    1260
agcagcggca gcttgtccgc caccgggcgc ctgggccgca gtaagcggaa gcggctggag    1320
gtggaggagc ccttgggcag cggcccaagc gtcctgggca cgggcacggg tggcagcggt    1380
ggcttccacc tggcccagca ggcctcggcc tcgggtagcg tcagcatcga ggagatcgac    1440
ctggagggca gtttgtgca gctcaagaac aactcggaca aggatcagtc tctggggaac     1500
tggagaatca agaggcaggt cttggagggg gaggagatcg cctacaagtt cacgcccaag    1560
tacatcctgc gcgccggcca gatggtcacg gtgtgggcag ctggtgcggg ggtggcccac    1620
agcccccct cgacgctggt gtggaagggc cagagcagct ggggcacggg cgagagcttc     1680
cgcaccgtcc tggttaacgc ggatggcgag gaagtggcca tgaggactgt gaagaagtcc    1740
tcggtgatgc gtgagaatga aatggggag gaagaggagg aggaagccga gtttggcgag    1800
gaggatcttt tccaccaaca gggggacccg aggaccacct caagaggctg ctacgtgatg    1860
tga                                                                  1863
```

<210> SEQ ID NO 26
<211> LENGTH: 620
<212> TYPE: PRT
<213> ORGANISM: Homo sapiens

<400> SEQUENCE: 26

```
Met Ser Pro Pro Ser Pro Gly Arg Arg Arg Glu Gln Arg Pro Arg
1               5                   10                  15

Ala Ala Ala Thr Met Ala Thr Pro Leu Pro Gly Arg Ala Gly Gly Pro
                20                  25                  30

Ala Thr Pro Leu Ser Pro Thr Arg Leu Ser Arg Leu Gln Glu Lys Glu
```

```
            35                  40                  45
Glu Leu Arg Glu Leu Asn Asp Arg Leu Ala His Tyr Ile Asp Arg Val
 50                  55                  60
Arg Ala Leu Glu Leu Glu Asn Asp Arg Leu Leu Lys Ile Ser Glu
 65                  70                  75                  80
Lys Glu Glu Val Thr Thr Arg Glu Val Ser Gly Ile Lys Ala Leu Tyr
                     85                  90                  95
Glu Ser Glu Leu Ala Asp Ala Arg Arg Val Leu Asp Glu Thr Ala Arg
                    100                 105                 110
Glu Arg Ala Arg Leu Gln Ile Glu Ile Gly Lys Leu Arg Ala Glu Leu
                    115                 120                 125
Asp Glu Val Asn Lys Ser Ala Lys Lys Arg Glu Gly Glu Leu Thr Val
                    130                 135                 140
Ala Gln Gly Arg Val Lys Asp Leu Glu Ser Leu Phe His Arg Ser Glu
145                 150                 155                 160
Val Glu Leu Ala Ala Ala Leu Ser Asp Lys Arg Gly Leu Glu Ser Asp
                    165                 170                 175
Val Ala Glu Leu Arg Ala Gln Leu Ala Lys Ala Glu Asp Gly His Ala
                    180                 185                 190
Val Ala Lys Lys Gln Leu Glu Lys Glu Thr Leu Met Arg Val Asp Leu
                    195                 200                 205
Glu Asn Arg Cys Gln Ser Leu Gln Glu Glu Leu Asp Phe Arg Lys Ser
                    210                 215                 220
Val Phe Glu Glu Glu Val Arg Glu Thr Arg Arg Arg His Glu Arg Arg
225                 230                 235                 240
Leu Val Glu Val Asp Ser Ser Arg Gln Gln Glu Tyr Asp Phe Lys Met
                    245                 250                 255
Ala Gln Ala Leu Glu Glu Leu Arg Ser Gln His Asp Glu Gln Val Arg
                    260                 265                 270
Leu Tyr Lys Leu Glu Leu Glu Gln Thr Tyr Gln Ala Lys Leu Asp Ser
                    275                 280                 285
Ala Lys Leu Ser Ser Asp Gln Asn Asp Lys Ala Ala Ser Ala Ala Arg
                    290                 295                 300
Glu Glu Leu Lys Glu Ala Arg Met Arg Leu Glu Ser Leu Ser Tyr Gln
305                 310                 315                 320
Leu Ser Gly Leu Gln Lys Gln Ala Ser Ala Glu Asp Arg Ile Arg
                    325                 330                 335
Glu Leu Glu Glu Ala Met Ala Gly Glu Arg Asp Lys Phe Arg Lys Met
                    340                 345                 350
Leu Asp Ala Lys Glu Gln Glu Met Thr Glu Met Arg Asp Val Met Gln
                    355                 360                 365
Gln Gln Leu Ala Glu Tyr Gln Glu Leu Leu Asp Val Lys Leu Ala Leu
                    370                 375                 380
Asp Met Glu Ile Asn Ala Tyr Arg Lys Leu Leu Glu Gly Glu Glu Glu
385                 390                 395                 400
Arg Leu Lys Leu Ser Pro Ser Pro Ser Ser Arg Val Thr Val Ser Arg
                    405                 410                 415
Ala Thr Ser Ser Ser Ser Gly Ser Leu Ser Ala Thr Gly Arg Leu Gly
                    420                 425                 430
Arg Ser Lys Arg Lys Arg Leu Glu Val Glu Glu Pro Leu Gly Ser Gly
                    435                 440                 445
Pro Ser Val Leu Gly Thr Gly Thr Gly Ser Gly Gly Phe His Leu
450                 455                 460
```

```
Ala Gln Gln Ala Ser Ala Ser Gly Ser Val Ser Ile Glu Glu Ile Asp
465                 470                 475                 480

Leu Glu Gly Lys Phe Val Gln Leu Lys Asn Asn Ser Asp Lys Asp Gln
                485                 490                 495

Ser Leu Gly Asn Trp Arg Ile Lys Arg Gln Val Leu Glu Gly Glu Glu
            500                 505                 510

Ile Ala Tyr Lys Phe Thr Pro Lys Tyr Ile Leu Arg Ala Gly Gln Met
        515                 520                 525

Val Thr Val Trp Ala Ala Gly Ala Val Ala His Ser Pro Pro Ser
530                 535                 540

Thr Leu Val Trp Lys Gly Gln Ser Ser Trp Thr Gly Glu Ser Phe
545                 550                 555                 560

Arg Thr Val Leu Val Asn Ala Asp Gly Glu Glu Val Ala Met Arg Thr
                565                 570                 575

Val Lys Lys Ser Ser Val Met Arg Glu Asn Glu Asn Gly Glu Glu Glu
            580                 585                 590

Glu Glu Glu Ala Glu Phe Gly Glu Glu Asp Leu Phe His Gln Gln Gly
        595                 600                 605

Asp Pro Arg Thr Thr Ser Arg Gly Cys Tyr Val Met
610                 615                 620

<210> SEQ ID NO 27
<211> LENGTH: 483
<212> TYPE: PRT
<213> ORGANISM: Homo sapiens

<400> SEQUENCE: 27

Val Ser Leu Trp Gly Gln Gly Asn Phe Phe Ser Leu Leu Pro Val Leu
1               5                   10                  15

Asn Trp Thr Ala Met Gln Pro Thr Gln Arg Val Asp Asp Ser Lys Gly
            20                  25                  30

Met His Arg Pro Gly Pro Leu Pro Ser Pro Pro Pro Lys Val Asp
        35                  40                  45

His Lys Ala Ser Gln Trp Pro Gln Glu Ser Asp Met Gly Gln Lys Val
50                  55                  60

Ala Ser Leu Ser Ala Gln Cys His Asn His Asp Glu Arg Leu Ala Glu
65                  70                  75                  80

Leu Thr Val Leu Leu Gln Lys Leu Gln Ile Arg Val Asp Gln Val Asp
                85                  90                  95

Asp Gly Arg Glu Gly Leu Ser Leu Trp Val Lys Asn Val Gly Gln
            100                 105                 110

His Leu Gln Glu Met Gly Thr Ile Glu Pro Pro Asp Ala Lys Thr Asp
        115                 120                 125

Phe Met Thr Phe His His Asp His Glu Val Arg Leu Ser Asn Leu Glu
130                 135                 140

Asp Val Leu Arg Lys Leu Thr Glu Lys Ser Glu Ala Ile Gln Lys Glu
145                 150                 155                 160

Leu Glu Glu Thr Lys Leu Lys Ala Gly Ser Arg Asp Glu Glu Gln Pro
                165                 170                 175

Leu Leu Asp Arg Val Gln His Leu Glu Leu Glu Leu Asn Leu Leu Lys
            180                 185                 190

Ser Gln Leu Ser Asp Trp Gln His Leu Lys Thr Ser Cys Glu Gln Ala
        195                 200                 205

Gly Ala Arg Ile Gln Glu Thr Val Gln Leu Met Phe Ser Glu Asp Gln
```

```
                210                 215                 220
Gln Gly Gly Ser Leu Glu Trp Leu Leu Glu Lys Leu Ser Arg Phe
225                 230                 235                 240

Val Ser Lys Asp Glu Leu Gln Val Leu Leu His Asp Leu Glu Leu Lys
                245                 250                 255

Leu Leu Gln Asn Ile Thr His His Ile Thr Val Thr Gly Gln Ala Pro
                260                 265                 270

Thr Ser Glu Ala Ile Val Ser Ala Val Asn Gln Ala Gly Ile Ser Gly
            275                 280                 285

Ile Thr Glu Ala Gln Ala His Ile Ile Val Asn Asn Ala Leu Lys Leu
        290                 295                 300

Tyr Ser Gln Asp Lys Thr Gly Met Val Asp Phe Ala Leu Glu Ser Gly
305                 310                 315                 320

Gly Gly Ser Ile Leu Ser Thr Arg Cys Ser Glu Thr Tyr Glu Thr Lys
                325                 330                 335

Thr Ala Leu Leu Ser Leu Phe Gly Val Pro Leu Trp Tyr Phe Ser Gln
                340                 345                 350

Ser Pro Arg Val Val Ile Gln Pro Asp Ile Tyr Pro Gly Asn Cys Trp
                355                 360                 365

Ala Phe Lys Gly Ser Gln Gly Tyr Leu Val Val Arg Leu Ser Met Lys
370                 375                 380

Ile Tyr Pro Thr Thr Phe Thr Met Glu His Ile Pro Lys Thr Leu Ser
385                 390                 395                 400

Pro Thr Gly Asn Ile Ser Ser Ala Pro Lys Asp Phe Ala Val Tyr Gly
                405                 410                 415

Leu Glu Thr Glu Tyr Gln Glu Glu Gly Gln Pro Leu Gly Arg Phe Thr
                420                 425                 430

Tyr Asp Gln Glu Gly Asp Ser Leu Gln Met Phe His Thr Leu Glu Arg
                435                 440                 445

Pro Asp Gln Ala Phe Gln Ile Val Glu Leu Arg Val Leu Ser Asn Trp
                450                 455                 460

Gly His Pro Glu Tyr Thr Cys Leu Tyr Arg Phe Arg Val His Gly Glu
465                 470                 475                 480

Pro Ile Gln

<210> SEQ ID NO 28
<211> LENGTH: 746
<212> TYPE: PRT
<213> ORGANISM: Homo sapiens

<400> SEQUENCE: 28

Met Lys Leu Gly Arg Ala Val Leu Gly Leu Leu Leu Leu Ala Pro Ser
1               5                   10                  15

Val Val Gln Ala Val Ala Ser Val Ser Lys Gly Glu Glu Leu Phe Thr
                20                  25                  30

Gly Val Val Pro Ile Leu Val Glu Leu Asp Gly Asp Val Asn Gly His
            35                  40                  45

Lys Phe Ser Val Ser Gly Glu Gly Glu Gly Asp Ala Thr Tyr Gly Lys
        50                  55                  60

Leu Thr Leu Lys Phe Ile Cys Thr Thr Gly Lys Leu Pro Val Pro Trp
65                  70                  75                  80

Pro Thr Leu Val Thr Thr Leu Thr Tyr Gly Val Gln Cys Phe Ser Arg
                85                  90                  95

Tyr Pro Asp His Met Lys Gln His Asp Phe Phe Lys Ser Ala Met Pro
```

-continued

```
                100                 105                 110
Glu Gly Tyr Val Gln Glu Arg Thr Ile Phe Phe Lys Asp Asp Gly Asn
            115                 120                 125

Tyr Lys Thr Arg Ala Glu Val Lys Phe Glu Gly Asp Thr Leu Val Asn
            130                 135                 140

Arg Ile Glu Leu Lys Gly Ile Asp Phe Lys Glu Asp Gly Asn Ile Leu
145                 150                 155                 160

Gly His Lys Leu Glu Tyr Asn Tyr Asn Ser His Asn Val Tyr Ile Met
            165                 170                 175

Ala Asp Lys Gln Lys Asn Gly Ile Lys Val Asn Phe Lys Ile Arg His
            180                 185                 190

Asn Ile Glu Asp Gly Ser Val Gln Leu Ala Asp His Tyr Gln Gln Asn
            195                 200                 205

Thr Pro Ile Gly Asp Gly Pro Val Leu Leu Pro Asp Asn His Tyr Leu
            210                 215                 220

Ser Thr Gln Ser Ala Leu Ser Lys Asp Pro Asn Glu Lys Arg Asp His
225                 230                 235                 240

Met Val Leu Leu Glu Phe Val Thr Ala Ala Gly Ile Thr Leu Gly Met
            245                 250                 255

Asp Glu Leu Tyr Lys Glu Phe Val Ser Leu Trp Gly Gln Gly Asn Phe
            260                 265                 270

Phe Ser Leu Leu Pro Val Leu Asn Trp Thr Ala Met Gln Pro Thr Gln
            275                 280                 285

Arg Val Asp Asp Ser Lys Gly Met His Arg Pro Gly Pro Leu Pro Pro
            290                 295                 300

Ser Pro Pro Lys Val Asp His Lys Ala Ser Gln Trp Pro Gln Glu
305                 310                 315                 320

Ser Asp Met Gly Gln Lys Val Ala Ser Leu Ser Ala Gln Cys His Asn
            325                 330                 335

His Asp Glu Arg Leu Ala Glu Leu Thr Val Leu Leu Gln Lys Leu Gln
            340                 345                 350

Ile Arg Val Asp Gln Val Asp Asp Gly Arg Glu Gly Leu Ser Leu Trp
            355                 360                 365

Val Lys Asn Val Val Gly Gln His Leu Gln Glu Met Gly Thr Ile Glu
            370                 375                 380

Pro Pro Asp Ala Lys Thr Asp Phe Met Thr Phe His His Asp His Glu
385                 390                 395                 400

Val Arg Leu Ser Asn Leu Glu Asp Val Leu Arg Lys Leu Thr Glu Lys
            405                 410                 415

Ser Glu Ala Ile Gln Lys Glu Leu Glu Thr Lys Leu Lys Ala Gly
            420                 425                 430

Ser Arg Asp Glu Glu Gln Pro Leu Leu Asp Arg Val Gln His Leu Glu
            435                 440                 445

Leu Glu Leu Asn Leu Leu Lys Ser Gln Leu Ser Asp Trp Gln His Leu
            450                 455                 460

Lys Thr Ser Cys Glu Gln Ala Gly Ala Arg Ile Gln Glu Thr Val Gln
465                 470                 475                 480

Leu Met Phe Ser Glu Asp Gln Gln Gly Gly Ser Leu Glu Trp Leu Leu
            485                 490                 495

Glu Lys Leu Ser Ser Arg Phe Val Ser Lys Asp Glu Leu Gln Val Leu
            500                 505                 510

Leu His Asp Leu Glu Leu Lys Leu Leu Gln Asn Ile Thr His His Ile
            515                 520                 525
```

```
Thr Val Thr Gly Gln Ala Pro Thr Ser Glu Ala Ile Val Ser Ala Val
    530                 535                 540

Asn Gln Ala Gly Ile Ser Gly Ile Thr Glu Ala Gln Ala His Ile Ile
545                 550                 555                 560

Val Asn Asn Ala Leu Lys Leu Tyr Ser Gln Asp Lys Thr Gly Met Val
            565                 570                 575

Asp Phe Ala Leu Glu Ser Gly Gly Ser Ile Leu Ser Thr Arg Cys
            580                 585                 590

Ser Glu Thr Tyr Glu Thr Lys Thr Ala Leu Leu Ser Leu Phe Gly Val
            595                 600                 605

Pro Leu Trp Tyr Phe Ser Gln Ser Pro Arg Val Val Ile Gln Pro Asp
            610                 615                 620

Ile Tyr Pro Gly Asn Cys Trp Ala Phe Lys Gly Ser Gln Gly Tyr Leu
625                 630                 635                 640

Val Val Arg Leu Ser Met Lys Ile Tyr Pro Thr Thr Phe Thr Met Glu
            645                 650                 655

His Ile Pro Lys Thr Leu Ser Pro Thr Gly Asn Ile Ser Ser Ala Pro
            660                 665                 670

Lys Asp Phe Ala Val Tyr Gly Leu Glu Thr Glu Tyr Gln Glu Glu Gly
            675                 680                 685

Gln Pro Leu Gly Arg Phe Thr Tyr Asp Gln Glu Gly Asp Ser Leu Gln
        690                 695                 700

Met Phe His Thr Leu Glu Arg Pro Asp Gln Ala Phe Gln Ile Val Glu
705                 710                 715                 720

Leu Arg Val Leu Ser Asn Trp Gly His Pro Glu Tyr Thr Cys Leu Tyr
            725                 730                 735

Arg Phe Arg Val His Gly Glu Pro Ile Gln
            740                 745

<210> SEQ ID NO 29
<211> LENGTH: 21
<212> TYPE: PRT
<213> ORGANISM: Homo sapiens

<400> SEQUENCE: 29

Met Lys Leu Gly Arg Ala Val Leu Gly Leu Leu Leu Leu Ala Pro Ser
1               5                   10                  15

Val Val Gln Ala Val
            20

<210> SEQ ID NO 30
<211> LENGTH: 237
<212> TYPE: PRT
<213> ORGANISM: Homo sapiens

<400> SEQUENCE: 30

Ser Lys Gly Glu Glu Leu Phe Thr Gly Val Val Pro Ile Leu Val Glu
1               5                   10                  15

Leu Asp Gly Asp Val Asn Gly His Lys Phe Ser Val Ser Gly Glu Gly
            20                  25                  30

Glu Gly Asp Ala Thr Tyr Gly Lys Leu Thr Leu Lys Phe Ile Cys Thr
        35                  40                  45

Thr Gly Lys Leu Pro Val Pro Trp Pro Thr Leu Val Thr Thr Leu Thr
    50                  55                  60

Tyr Gly Val Gln Cys Phe Ser Arg Tyr Pro Asp His Met Lys Gln His
65                  70                  75                  80
```

```
Asp Phe Phe Lys Ser Ala Met Pro Glu Gly Tyr Val Gln Glu Arg Thr
                85                  90                  95

Ile Phe Phe Lys Asp Asp Gly Asn Tyr Lys Thr Arg Ala Glu Val Lys
                100                 105                 110

Phe Glu Gly Asp Thr Leu Val Asn Arg Ile Glu Leu Lys Gly Ile Asp
                115                 120                 125

Phe Lys Glu Asp Gly Asn Ile Leu Gly His Lys Leu Glu Tyr Asn Tyr
            130                 135                 140

Asn Ser His Asn Val Tyr Ile Met Ala Asp Lys Gln Lys Asn Gly Ile
145                 150                 155                 160

Lys Val Asn Phe Lys Ile Arg His Asn Ile Glu Asp Gly Ser Val Gln
                165                 170                 175

Leu Ala Asp His Tyr Gln Gln Asn Thr Pro Ile Gly Asp Gly Pro Val
                180                 185                 190

Leu Leu Pro Asp Asn His Tyr Leu Ser Thr Gln Ser Ala Leu Ser Lys
                195                 200                 205

Asp Pro Asn Glu Lys Arg Asp His Met Val Leu Leu Glu Phe Val Thr
            210                 215                 220

Ala Ala Gly Ile Thr Leu Gly Met Asp Glu Leu Tyr Lys
225                 230                 235

<210> SEQ ID NO 31
<211> LENGTH: 483
<212> TYPE: PRT
<213> ORGANISM: Homo sapiens

<400> SEQUENCE: 31

Val Ser Leu Trp Gly Gln Gly Asn Phe Phe Ser Leu Leu Pro Val Leu
1               5                   10                  15

Asn Trp Thr Ala Met Gln Pro Thr Gln Arg Val Asp Asp Ser Lys Gly
                20                  25                  30

Met His Arg Pro Gly Pro Leu Pro Ser Pro Pro Lys Val Asp
                35                  40                  45

His Lys Ala Ser Gln Trp Pro Gln Glu Ser Asp Met Gly Gln Lys Val
            50                  55                  60

Ala Ser Leu Ser Ala Gln Cys His Asn His Asp Glu Arg Leu Ala Glu
65                  70                  75                  80

Leu Thr Val Leu Leu Gln Lys Leu Gln Ile Arg Val Asp Gln Val Asp
                85                  90                  95

Asp Gly Arg Glu Gly Leu Ser Leu Trp Val Lys Asn Val Val Gly Gln
                100                 105                 110

His Leu Gln Glu Met Gly Thr Ile Glu Pro Pro Asp Ala Lys Thr Asp
                115                 120                 125

Phe Met Thr Phe His His Asp His Glu Val Arg Leu Ser Asn Leu Glu
            130                 135                 140

Asp Val Leu Arg Lys Leu Thr Glu Lys Ser Glu Ala Ile Gln Lys Glu
145                 150                 155                 160

Leu Glu Glu Thr Lys Leu Lys Ala Gly Ser Arg Asp Glu Glu Gln Pro
                165                 170                 175

Leu Leu Asp Arg Val Gln His Leu Glu Leu Glu Leu Asn Leu Leu Lys
                180                 185                 190

Ser Gln Leu Ser Asp Trp Gln His Leu Lys Thr Ser Cys Glu Gln Ala
                195                 200                 205

Gly Ala Arg Ile Gln Glu Thr Val Gln Leu Met Phe Ser Glu Asp Gln
```

```
                    210                 215                 220
Gln Gly Gly Ser Leu Glu Trp Leu Leu Glu Lys Leu Ser Arg Phe
225                 230                 235                 240

Val Ser Lys Asp Glu Leu Gln Val Leu Leu His Asp Leu Glu Leu Lys
                245                 250                 255

Leu Leu Gln Asn Ile Thr His His Ile Thr Val Thr Gly Gln Ala Pro
                260                 265                 270

Thr Ser Glu Ala Ile Val Ser Ala Val Asn Gln Ala Gly Ile Ser Gly
            275                 280                 285

Ile Thr Glu Ala Gln Ala His Ile Ile Val Asn Asn Ala Leu Lys Leu
        290                 295                 300

Tyr Ser Gln Asp Lys Thr Gly Met Val Asp Phe Ala Leu Glu Ser Gly
305                 310                 315                 320

Gly Gly Ser Ile Leu Ser Thr Arg Cys Ser Glu Thr Tyr Glu Thr Lys
                325                 330                 335

Thr Ala Leu Leu Ser Leu Phe Gly Val Pro Leu Trp Tyr Phe Ser Gln
                340                 345                 350

Ser Pro Arg Val Val Ile Gln Pro Asp Ile Tyr Pro Gly Asn Cys Trp
                355                 360                 365

Ala Phe Lys Gly Ser Gln Gly Tyr Leu Val Val Arg Leu Ser Met Lys
        370                 375                 380

Ile Tyr Pro Thr Thr Phe Thr Met Glu His Ile Pro Lys Thr Leu Ser
385                 390                 395                 400

Pro Thr Gly Asn Ile Ser Ser Ala Pro Lys Asp Phe Ala Val Tyr Gly
                405                 410                 415

Leu Glu Thr Glu Tyr Gln Glu Glu Gly Gln Pro Leu Gly Arg Phe Thr
                420                 425                 430

Tyr Asp Gln Glu Gly Asp Ser Leu Gln Met Phe His Thr Leu Glu Arg
                435                 440                 445

Pro Asp Gln Ala Phe Gln Ile Val Glu Leu Arg Val Leu Ser Asn Trp
            450                 455                 460

Gly His Pro Glu Tyr Thr Cys Leu Tyr Arg Phe Arg Val His Gly Glu
465                 470                 475                 480

Pro Ile Gln
```